(12) United States Patent
Reasoner et al.

(10) Patent No.: US 8,740,866 B2
(45) Date of Patent: Jun. 3, 2014

(54) MEDICAL/SURGICAL WASTE COLLECTION AND DISPOSAL SYSTEM INCLUDING A ROVER AND A DOCKER, THE DOCKER HAVING FEATURES FACILITATING THE ALIGNMENT OF THE DOCKER WITH THE ROVER

(75) Inventors: Stephen J. Reasoner, Kalamazoo, MI (US); Chamara Gamhewage, Kalamazoo, MI (US); Joseph P. Hepp, III, Lutherville, MD (US)

(73) Assignee: Stryker Corporation, Kalamazoo, MI (US)

( * ) Notice: Subject to any disclaimer, the term of this patent is extended or adjusted under 35 U.S.C. 154(b) by 518 days.

(21) Appl. No.: 12/609,041

(22) Filed: Oct. 30, 2009

(65) Prior Publication Data

US 2010/0049152 A1 Feb. 25, 2010

Related U.S. Application Data

(62) Division of application No. 11/610,071, filed on Dec. 13, 2006, now Pat. No. 7,621,898.

(60) Provisional application No. 60/750,862, filed on Dec. 14, 2005.

(51) Int. Cl.
*A61M 1/00* (2006.01)

(52) U.S. Cl.
USPC .............. 604/319; 604/27; 604/35; 604/48; 604/65; 604/118; 604/119; 604/317; 604/318; 604/322; 604/326; 137/205; 141/35; 141/59; 141/65; 141/95; 141/198; 119/14.46

(58) Field of Classification Search
USPC .................................. 604/317, 318, 319, 322
See application file for complete search history.

(56) References Cited

U.S. PATENT DOCUMENTS

| 3,612,089 A | 10/1971 | Beguiristain |
| 4,014,329 A | 3/1977 | Welch et al. |

(Continued)

FOREIGN PATENT DOCUMENTS

| EP | 0 184 629 A2 | 6/1986 |
| EP | 0882440 | 12/1998 |

(Continued)

OTHER PUBLICATIONS

International Search Report May 31, 2007; International Application No. PCT/US2006/047531, filed Dec. 13, 2006 and Written Opinion.

(Continued)

*Primary Examiner* — Tatyana Zalukaeva
*Assistant Examiner* — Ilya Treyger

(57) ABSTRACT

A waste collection and disposal system for use in health care facilities is provided. The system includes a mobile waste collection unit for moving between use areas in the health care facility to collect waste material generated during medical procedures including body fluids, body tissues, saline, etc. The waste collection unit includes stacked upper and lower waste containers for receiving the waste material. During use, the upper waste container can be emptied into the lower waste container for temporary storage. In addition, different vacuum levels can be provided in the waste containers during complex procedures. Once a user desires to empty the waste collection unit, the waste collection unit is wheeled to a docking station. At the docking station, the waste material is off-loaded to a waste drain and the waste collection unit is cleaned and rinsed for further use.

24 Claims, 58 Drawing Sheets

(56) References Cited

U.S. PATENT DOCUMENTS

| | | |
|---|---|---|
| 4,475,904 A | 10/1984 | Wang |
| 4,744,785 A | 5/1988 | Rosenthal et al. |
| 4,863,446 A | 9/1989 | Parker |
| 5,112,019 A | 5/1992 | Metzler et al. |
| 5,195,961 A | 3/1993 | Takahashi et al. |
| 5,242,434 A | 9/1993 | Terry |
| 5,242,474 A | 9/1993 | Herbst et al. |
| 5,312,377 A | 5/1994 | Dalton |
| 5,613,966 A | 3/1997 | Makower et al. |
| 5,624,417 A | 4/1997 | Cook et al. |
| 5,736,098 A | 4/1998 | Kerwin et al. |
| 5,885,240 A | 3/1999 | Bradbury et al. |
| 5,968,032 A | 10/1999 | Sleister |
| 5,997,733 A | 12/1999 | Wilbur et al. |
| 6,024,720 A | 2/2000 | Chandler et al. |
| 6,027,490 A | 2/2000 | Radford et al. |
| 6,056,731 A | 5/2000 | Koetke et al. |
| 6,180,000 B1 | 1/2001 | Wilbur et al. |
| 6,222,283 B1 | 4/2001 | Regla |
| 6,244,311 B1 | 6/2001 | Hand et al. |
| 6,273,296 B1 | 8/2001 | Brown |
| 6,391,102 B1 | 5/2002 | Bodden et al. |
| 6,400,141 B1 | 6/2002 | Apel et al. |
| 6,770,061 B2 | 8/2004 | Wildman |
| 6,893,425 B2 | 5/2005 | Dunn et al. |
| 2003/0164600 A1 | 9/2003 | Dunn |
| 2003/0213733 A1 | 11/2003 | Beckham et al. |
| 2004/0016691 A1 | 1/2004 | Smit et al. |
| 2004/0079418 A1 | 4/2004 | Weis et al. |
| 2004/0102743 A1 | 5/2004 | Walker |
| 2004/0138632 A1 | 7/2004 | Bemis et al. |
| 2004/0143227 A1 | 7/2004 | Rollin et al. |
| 2004/0163884 A1 | 8/2004 | Austin et al. |
| 2004/0261525 A1 | 12/2004 | Chen |
| 2005/0127212 A1 | 6/2005 | Kassanits |
| 2005/0171495 A1 | 8/2005 | Austin et al. |
| 2005/0173638 A1 | 8/2005 | Powell |
| 2005/0183780 A1 | 8/2005 | Michaels et al. |
| 2005/0187529 A1 | 8/2005 | Reasoner et al. |
| 2005/0189288 A1 | 9/2005 | Hershberger et al. |
| 2005/0209585 A1 | 9/2005 | Nord et al. |

FOREIGN PATENT DOCUMENTS

| | | | |
|---|---|---|---|
| EP | 1 166 805 A2 | | 1/2002 |
| EP | 2359878 A3 | | 3/2012 |
| EP | 2359879 A3 | | 3/2012 |
| EP | 2364736 A3 | | 3/2012 |
| JP | 2003-325658 A | | 11/2003 |
| WO | 9626750 | | 9/1996 |
| WO | 9900154 | | 1/1999 |
| WO | WO 99/00154 | * | 1/1999 |
| WO | 2005079947 | | 9/2005 |
| WO | 2007/103842 A2 | | 9/2007 |

OTHER PUBLICATIONS

USPTO Office Action for U.S. Appl. No. 11/554,616; Sep. 2008.
USPTO Office Action for U.S. Appl. No. 11/554,616; Feb. 2009.
ISA Search Report and Written Opinion for PCT/US2006/061791; Jun. 2008.
Stryker Instruments, Neptune Waste Management System, Instructions for Use, Neptune Gold Rover, REF 700-2, Neptune Docking Station, REF 700-6, dated Sep. 2005, 19 pages.
EPO Search Report, App. No. 11 002 752.1, Feb. 27, 2012.
EPO Search Report, App. No. 11 002 753.9 Feb. 27, 2012.
EPO Search Report, App. No. 11 002 751.3 Feb. 27, 2012.

* cited by examiner

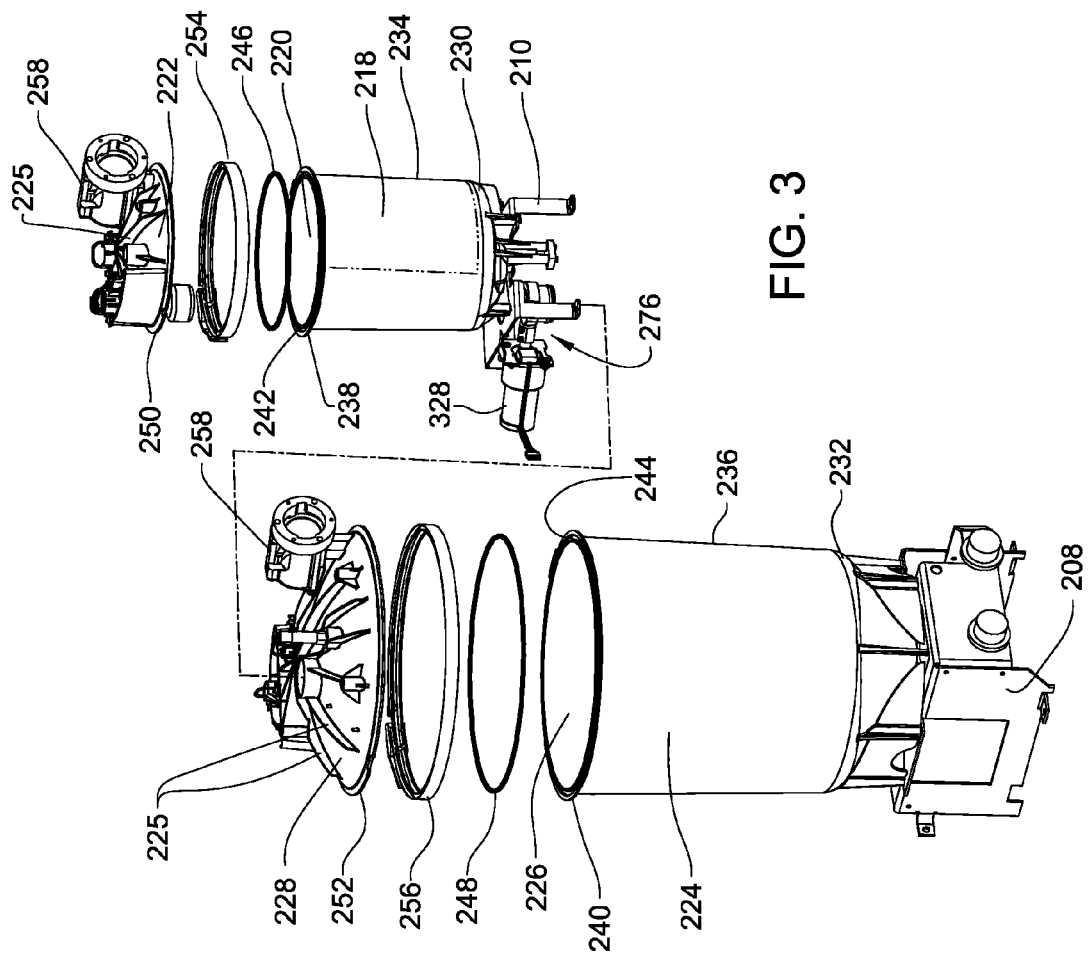

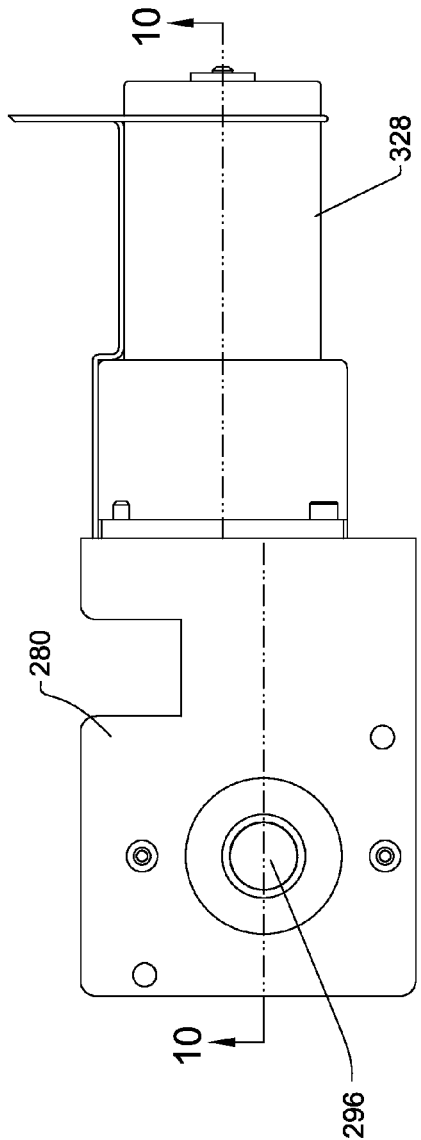
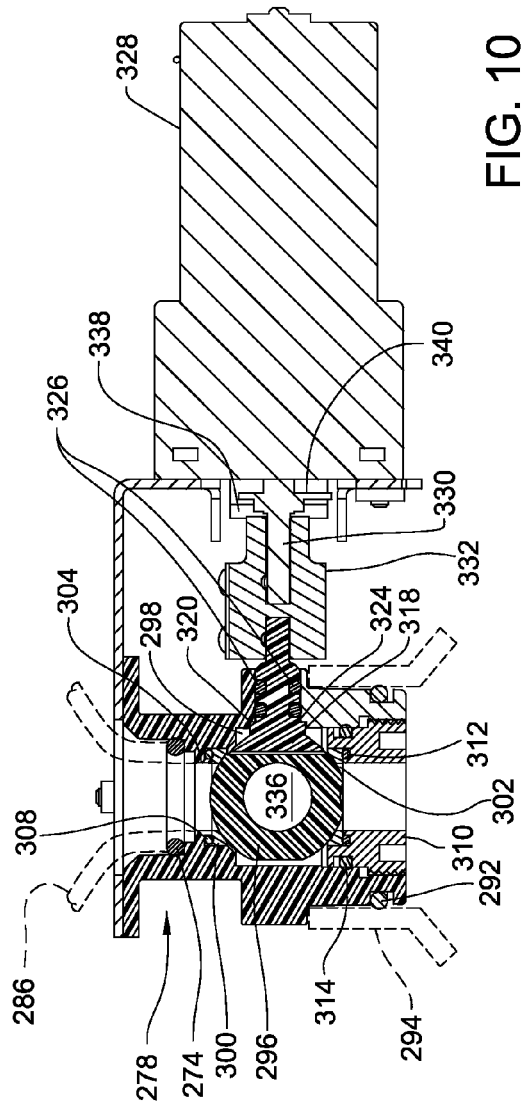
FIG. 9
FIG. 10

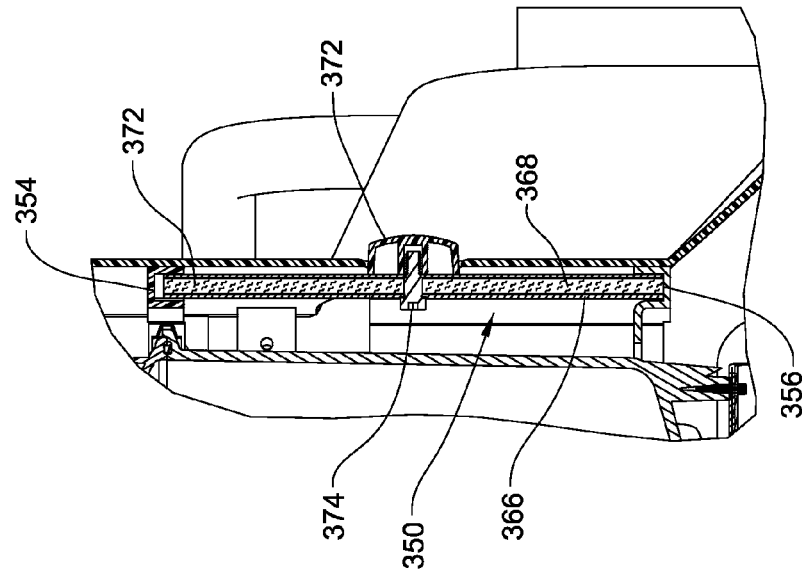
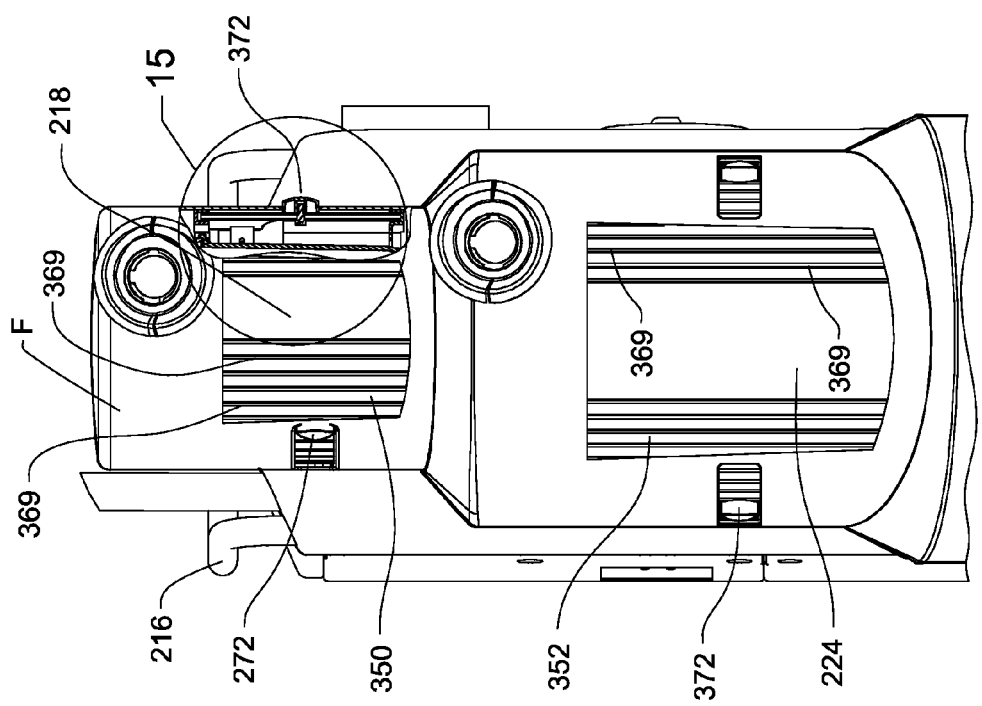

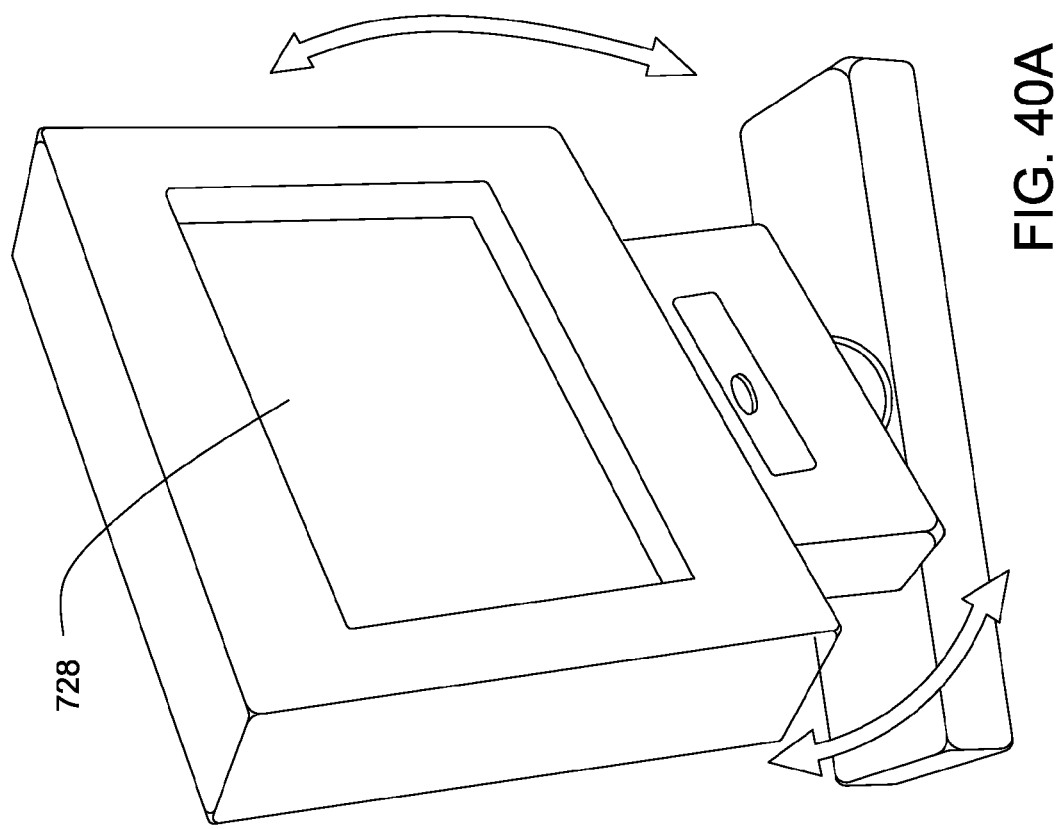

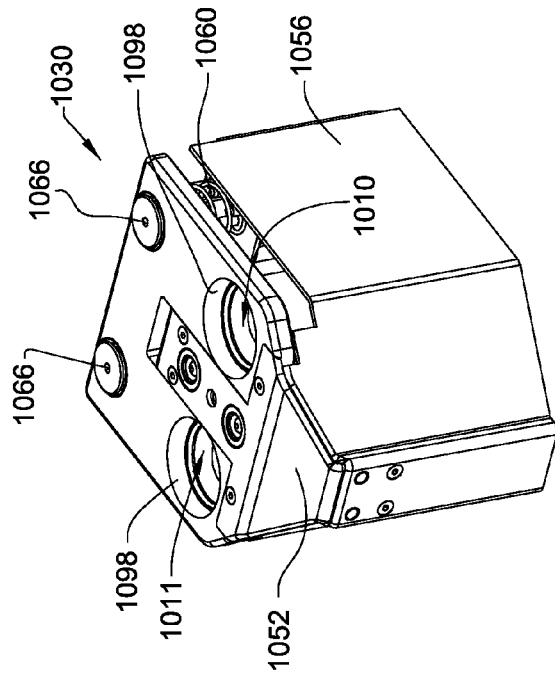
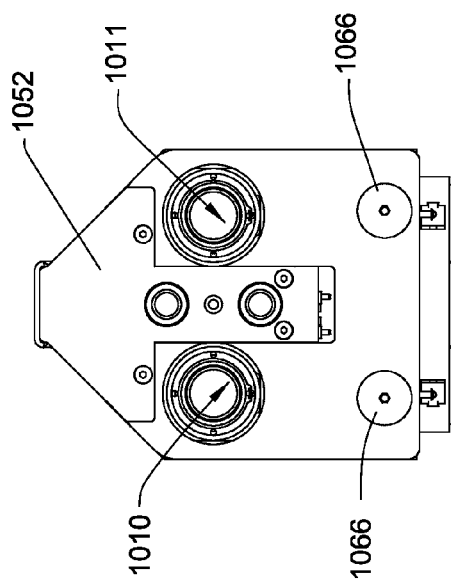
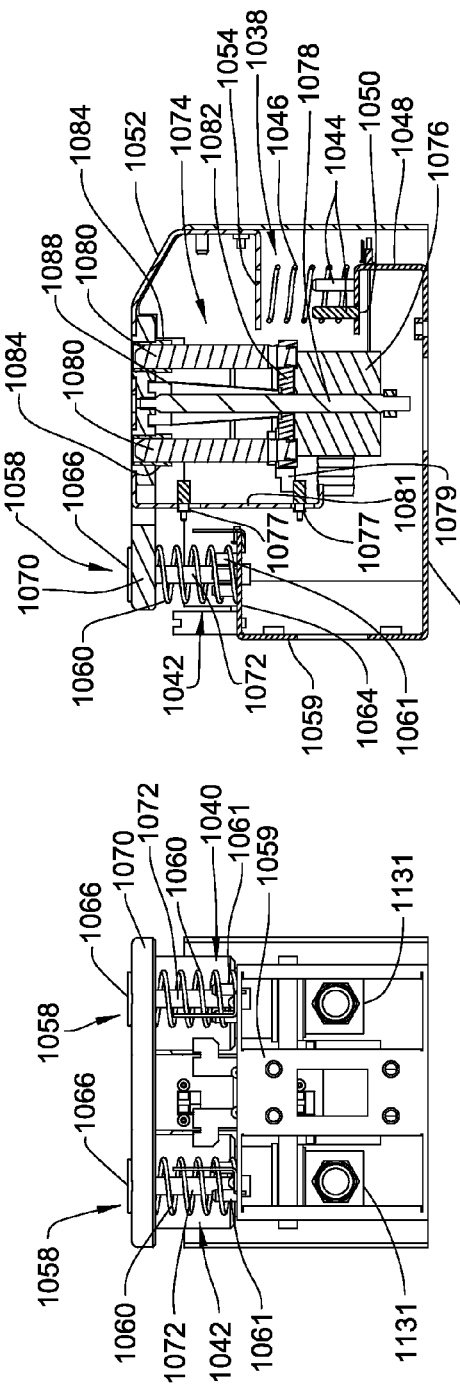

MEDICAL/SURGICAL WASTE COLLECTION AND DISPOSAL SYSTEM INCLUDING A ROVER AND A DOCKER, THE DOCKER HAVING FEATURES FACILITATING THE ALIGNMENT OF THE DOCKER WITH THE ROVER

CROSS-REFERENCE TO RELATED APPLICATIONS

This application is a divisional of U.S. application Ser. No. 11/610,071, filed Dec. 13, 2006, which claims the benefit of U.S. provisional patent application No. 60/750,862, filed on Dec. 14, 2005, the advantages and disclosure of both are hereby incorporated by reference.

FIELD OF THE INVENTION

The present invention relates to a waste collection and disposal system for collecting and disposing of waste materials, such as bodily fluids, generated during medical procedures carried out in a health care facility, e.g., a hospital. More specifically, the present invention relates to a waste collection unit for collecting the waste material and a docking station for disposing of the waste material from the waste collection unit and cleaning the waste collection unit for further use.

BACKGROUND OF THE INVENTION

Waste collection and disposal systems are well known for use in health care facilities to collect waste material generated during medical procedures. Examples of such systems can be found in U.S. Pat. No. 4,863,446 to Parker and U.S. Pat. No. 5,997,733 to Wilbur et al. In these types of systems, the waste material is collected in a waste container connected to a vacuum source. A portable cart supports the waste container for moving throughout the health care facility. One or more suction lines extend from the waste container and are positioned near the site from which the waste material is to be collected. When the vacuum source is operating, the waste material is drawn through the suction lines into the waste container. The waste material is typically collected until the waste container is filled to a predetermined level. Once the waste container is full, or if an empty waste container is required prior to being full, the waste collection unit is wheeled to a docking station to be emptied and cleaned. The waste collection unit docks to the docking station to begin emptying. Once emptied, the waste container is cleaned by a cleaning system with disinfectant and rinsed.

While providing suitable waste collection and disposal, these prior art systems could be improved. For instance, these prior art systems employ a single waste container for collecting the waste material. As a result, if there is a particular need for the waste container to be emptied prior to use, the waste collection unit must be wheeled down to the docking station to off-load any collected waste material before resuming operation. If a series of medical procedures are performed in which it is necessary to empty the waste container before each procedure, the user could find it annoying to have to continuously wheel the waste collection unit back and forth between a use area, such as an operating room, and the docking station, which is typically situated outside of the operating room in a hallway near a waste drain. Therefore, there is a need in the art for a system that is capable of use in multiple medical procedures requiring an empty waste container without the need to dock the waste collection unit to the docking station.

Moreover, it is common for medical personnel to, during a procedure, glance at the unit's container to obtain a quick visual estimate of the amount of material removed during the procedure. Many known waste collection units have containers capable of storing 15 liters or more of extracted material. Thus, these containers are relatively large in size. Accordingly, a quick glance at one of these containers to estimate the quantity of removed material produces only a rough estimate of removed material. In theory, one could improve the estimate by substituting a smaller sized container. Glancing at this size of container would provide a more precise estimate of removed material. However, a disadvantage of providing a waste collection unit with a small container, for example one capable of storing 10 or less liters of waste would mean that the container would become filled more quickly. This would then result in the interruption of the procedure in order to empty the waste collection unit. Having to delay the procedure to perform this task runs counter to one of the goals of modern surgery; that the time to perform the procedure should be as fast as possible in order to minimize the time the patient is held under anesthesia.

In certain instances, it may become necessary to use a plurality of suction lines to draw waste materials from a plurality of sites during a medical procedure. Currently, the prior art systems allow for utilizing multiple suction lines, but only a single vacuum source is available such that each suction line essentially operates under the same vacuum pressure. As medical procedures become more advanced and faster-paced to improve patient outcomes, there is an increasing need to provide different vacuum levels in the suction lines during the same medical procedure.

The waste collection units of the prior art currently employ a float to prevent the waste material from entering the vacuum source once the waste material reaches a predetermined threshold level in the waste container. However, these units are also susceptible to water droplets that may enter the vacuum source inadvertently before the waste material rises to the predetermined threshold level in the waste container. Therefore, there is a need for an assembly that not only prevents the waste material from entering the vacuum source, but also prevents other potentially harmful materials from entering the vacuum source, such as water droplets that may foul the downstream vacuum source.

The vacuum source and cleaning system of the prior art waste collection unit are connected to the waste container through various waste and/or water lines supported on the portable cart. Often, these lines are hoses connected to barbed nozzles on conventional connectors that are threaded into caps of the waste containers. Once the hoses are connected to the barbed nozzles, they are difficult to remove for servicing. Therefore, there is a need for quick-releasing connectors on these lines to simplify servicing of the waste collection unit.

The known waste collection units also have electro-mechanical systems that provide indications of the volume of waste stored in their containers. Often this system includes some type of float member the position of which is sensed. Based on the height of the float member in the container, this volume measuring system outputs data indicating the volume of waste in the container. The known prior art volume measuring systems do not take into account variations in volume due to temperature or variations in volume due to the manufacturing of each container. Therefore, there is a need for a sensing device which can share components to lower cost and which takes into account temperature and manufacturing variations of the containers.

Smoke evacuation systems of the prior art utilize a blower to draw in air and smoke from a surgical area. Unfortunately, these blowers, when operating, tend to be noisy, and thus distracting to medical personnel performing the medical procedures. Therefore, there is a need for a smoke evacuation system that reduces noise yet maintains performance standards for removing smoke.

Prior art waste collection systems have typically included an IV pole for supporting one or more IV bags. The IV pole is supported by a mobile waste collection unit, such that it is movable with the waste collection unit. Unfortunately, the height of such IV poles often prohibits medical personnel of a smaller stature from reaching the top of the IV pole to hang the IV bags. Furthermore, the IV poles are prone to damage from doorways and other structures when the waste collection unit is moved. Therefore, there is a need for an IV pole that is retractable such that smaller stature medical personnel can operate them and damage to the IV pole is minimized.

In one example of a prior art system, the waste collection unit includes a first pair of couplings that lead to the waste container and the cleaning system. The first pair of couplings is disposed on a front of the waste collection unit. The docking station includes a cabinet that houses a second pair of couplings for mating with the complimentary first pair of couplings on the waste collection unit. These couplings mate to drain the waste material from the waste containers during docking and to provide cleaner to the waste collection unit. When docking, the waste collection unit engages the docking station to open a set of doors that otherwise conceal the second pair of couplings. When the doors are opened, the second pair of couplings advances from inside the cabinet to outside the cabinet to engage the first pair of couplings of the waste collection unit. When off-loading the waste material, the first pair of couplings can become dirtied with waste material, and since they are externally disposed on the front of the waste collection unit, can be unsightly. Therefore, there is a need for improved docking between the waste collection unit and the docking station to reduce any visually unappealing conditions.

The cleaning systems of the prior art waste collection units include a sprinkler that operates similarly to a rotating lawn sprinkler with moving parts that are subject to breaking. It is desirable to reduce the number of moving parts in the sprinkler. It is also desirable to provide a sprinkler that is capable of simultaneously directing a stream of cleaner to each of the parts of the waste containers that need to be cleaned.

SUMMARY OF THE INVENTION

The present invention provides a waste collection unit for collecting waste material during a series of medical procedures. The waste collection unit includes first and second waste containers. The first waste container has a maximum storage volume. The second waste container has a maximum storage volume larger than the maximum storage volume of the first waste container. The first waste container is adapted for connection to one suction line to collect the waste material in the first waste container during a medical procedure. The second waste container is adapted for connection to another suction line to collect the waste material in the second waste container during the medical procedure. A vacuum source is in selective communication with the waste containers to provide a vacuum in the waste containers and draw the waste material into the waste containers through the suction lines during the medical procedure. A transfer valve is disposed between the waste containers. In the open position, the transfer valve allows the waste material in the first waste container to flow into the second waste container. This feature of the waste collection unit of this invention reduces the number or trips that a user has to make between use areas in which the waste material is being collected (such as an operating room) and the docking station, which is typically located outside of the use area.

A method of collecting the waste material during the series of medical procedures is also provided. The method includes transporting the portable waste collection unit to a first use area and connecting at least one suction line to the portable waste collection unit. A vacuum source is operated to provide a vacuum in the first waste container and draw the waste material into the first waste container through the at least one suction line. The first waste container is at least partially filled with waste material during a first of the medical procedures. The waste material is then transferred from the first waste container to the second waste container without moving the waste collection unit out of the first use area. The first waste container is then at least partially filled again with waste material during a second of the medical procedures without emptying the waste material transferred from the second waste container.

The present invention also provides a first vacuum regulator in fluid communication with the vacuum source for regulating a vacuum level in the first waste container and a second vacuum regulator in fluid communication with the vacuum source for regulating a vacuum level in the second waste container. A control system is in communication with the first and second vacuum regulators. The control system is adapted to simultaneously control the first and second vacuum regulators to control the vacuum levels in the first and second waste containers independently of one another such that the vacuum levels are capable of being different. This is accomplished using a single vacuum source.

By providing independently controlled vacuum levels in the waste containers, the waste collection unit can be employed in those instances in which it is necessary to use a plurality of suction lines of varying suction to draw waste materials from a plurality of sites during a single medical procedure. As medical procedures continue to advance, there may be an increasing need to provide different suction levels in the suction lines during the same medical procedure. In addition, the first and second vacuum regulators of the present invention are designed to provide independently controlled vacuum levels in the waste containers from a single vacuum source. This eliminates the need for separate vacuum pumps to draw different vacuum levels in the waste containers.

A filter and float assembly is also provided in one or more of the waste containers to prevent water droplets and waste material from entering the vacuum source and potentially fouling the vacuum source. The waste container defines a collection chamber, a filter compartment, and a vacuum port opening into the filter compartment. The vacuum source is in communication with the vacuum port of the waste container to provide a vacuum in the waste container to draw the waste material into the waste container through the suction line(s). The filter and float assembly is disposed in the filter compartment adjacent to the vacuum port. The filter and float assembly comprises a filter element disposed between the vacuum port and the collection chamber for removing moisture from fluid entering into the vacuum port from the collection chamber. The filter and float assembly also includes a retaining member to secure the filter element in position. The retaining member defines a sleeve. A float is slidably supported in the sleeve to prevent the waste material collected in the waste container from entering into the vacuum port when a level of the waste material exceeds a predetermined threshold.

In another aspect of the present invention, a connector is used to connect a vacuum line to a cap of the first waste container. The connector is coupled to the vacuum line and is seated in a corresponding receptacle in the cap. A first retainer is rotatably supported by the cap for rotating between a locked position to retain the first connector in the first receptacle and an unlocked position to release the first connector from the first receptacle. By utilizing this quick-release, the waste collection unit can be quickly and easily serviced. Otherwise, if conventional connectors were used, it may take several minutes to release the connectors from the cap to service the vacuum circuit or other systems of the waste collection unit.

The present invention also provides a fluid measuring system for estimating the volume of waste material collected in upper and lower waste containers. The fluid measuring system comprises a sensor rod extending through the waste containers. A transceiver is electrically connected to the sensor rod to propagate an interrogation pulse along the sensor rod and receive return pulses. A lower reference element is disposed adjacent to a bottom of the lower waste container and adjacent to the sensor rod to cause a lower reference return pulse in response to receiving the interrogation pulse. A lower float element is disposed within the lower waste container and adjacent to the sensor rod to float near a surface of a liquid contained within the lower waste container and to cause a lower float return pulse in response to receiving the interrogation pulse. An upper reference element is disposed adjacent to a bottom of the upper waste container and adjacent to the sensor rod to cause an upper reference return pulse in response to receiving the interrogation pulse. An upper float element is disposed within the upper waste container and adjacent to the sensor rod to float near a surface of a liquid contained within the upper waste container and to cause an upper float return pulse in response to receiving the interrogation pulse.

A method of estimating the volume of a substance in one or more of the waste containers is also provided. The method includes propagating the interrogation pulse from the transceiver along the sensor rod at an interrogation time in response to an interrogation command. A float return pulse is received at the transceiver at a float return time. A reference return pulse is received at the transceiver at a reference return time. The float return time and the reference return time are communicated to a controller. The controller then calculates the volume of the substance in the waste container based on the float return time and the reference return time.

In another aspect of the present invention, the waste collection unit includes a portable cart to carry a waste container and a reservoir is supported by the portable cart and in fluid communication with the waste container. The reservoir stores a liquid that is dispensed to the waste container in order to raise a float element in the waste container prior to waste material being collected in the waste container.

A smoke evacuation system is provided for removing smoke during the medical procedures. The system comprises a smoke conduit including an inlet and an outlet. A blower is in fluid communication with the smoke conduit for drawing a fluid into the inlet and exhausting the fluid out of the outlet. A blower motor operatively connects to the blower. A blower control circuit is electrically connected to the blower motor to provide electrical power to the blower motor and control a speed of the blower. A smoke sensor is in fluid communication with the smoke conduit to sense an amount of smoke traveling through the smoke conduit. A controller is electrically connected to the smoke sensor and the blower control circuit to adjust the speed of the blower based on the amount of smoke traveling through the smoke conduit.

A method for controlling the speed of the blower motor in the smoke evacuation system is also provided. The method includes providing electrical power at a first level to the blower motor such that the blower operates at a first speed. The method further includes receiving a smoke sensor signal representing an amount of smoke sensed in the smoke conduit. The electrical power to the blower motor is increased to a second level such that the blower operates at a second speed faster than the first speed in response to the amount of smoke being greater than a predetermined limit.

With this type of smoke evacuation system and associated method, smoke removal can be automatically carried out without requiring any interaction by a user. The user simply indicates that smoke removal is desired and the controller operates the blower motor at the appropriate level based on the amount of smoke detected.

An intravenous (IV) bag support pole assembly is provided on a portable cart for supporting at least one IV bag. The assembly includes an IV bag support pole having a proximal end and a distal end. The pole includes a plurality of segments telescopingly interfaced together. At least one IV bag hook is coupled to the distal end of the pole for supporting the IV bag. A direct current (DC) motor has a rotatably shaft operatively connected to one of the segments for telescopically actuating the pole between a fully extended position and a fully retracted position. The rotatable shaft is operable by an electrical portion. A motor control circuit is electrically connected to the electrical portion for selectively providing motor power to the DC motor. A slowdown circuit is electrically connected to the electrical portion of the DC motor for periodically stopping rotation of the rotatable shaft when the motor power is unavailable, thus slowing retraction of the pole. When the pole assembly is mounted to the waste collection unit, this slowdown circuit provides that advantage of automatically retracting the pole when power is disconnected from the waste collection unit.

A docking station is also provided for disposing of the waste material collected by the waste collection unit and for cleaning the waste containers. The waste collection unit is outfitted with a carrier for holding a first plurality of couplings that are in communication with the waste containers and with a cleaning system on the waste collection unit. The docking station is fixed at a location in a health care facility. The docking station includes a cabinet. A head extends from the cabinet. The head includes a second plurality of couplings for mating with the first plurality of couplings. A mating interface carries the second plurality of couplings and moves the second plurality of couplings upwardly, relative to gravity, to make the connection to the first plurality of couplings. The head includes a floating frame carrying the mating interface for engagement by the carrier such that the floating frame aligns the second plurality of couplings with the first plurality of couplings when engaged by the carrier to facilitate mating of the couplings. By moving the second plurality of couplings upwardly, the waste collection unit can be wheeled over top of the head such that the connection of the couplings is largely hidden from view. Furthermore, by providing the floating frame, alignment of the couplings is made possible prior to moving the second plurality of couplings upwardly.

A method of docking a first plurality of couplings of the waste collection unit to a second plurality of couplings of the docking station is also provided. The method includes transporting the waste collection unit from a use area to the docking station. The carrier of the waste collection unit then engages the head of the docking station to slide the carrier directly over top of the head of the docking station. The second plurality of couplings of the docking station is then lifted upwardly while concealing the first and second plurality of couplings from view. The first and second plurality of couplings then mate together to provide fluid communication between the waste collection unit and the docking station for purposes of draining the waste material from the waste collection unit and/or cleaning the waste collection unit.

A cleaning system is provided for cleaning one or more of the waste containers on the waste collection unit. The cleaning system is supported by the portable cart and includes a sprinkler mounted in caps of each of the waste containers. The sprinkler is fixed to the cap and stationary relative to the cap. The sprinkler has a head with a plurality of asymmetric jet ports configured to direct a stream of cleaner to each of the cap, the wall of the waste container, the bottom of the waste container, the sensor rod, and float element.

A power coupler is also provided for transferring electric power from the docking station to the waste collection unit. The power coupler includes a first winding supported by the docking station and electrically connectable to a fixed power source. The power coupler further includes a second winding supported by the waste collection unit and inductively coupleable to the first winding when the waste collection unit is docked to the docking station. The power coupler provides for operation of the waste collection unit without requiring an on-board battery on the waste collection. By coupling power from a fixed power source to the waste collection unit, time and costs can be saved.

BRIEF DESCRIPTION OF THE SEVERAL VIEWS OF THE DRAWINGS

Advantages of the present invention will be readily appreciated as the same becomes better understood by reference to the following detailed description when considered in connection with the accompanying drawings wherein:

FIG. 3 is an exploded perspective view of the upper and lower waste containers;

FIG. 9 is a top view of the transfer valve and valve motor;

FIG. 10 is a cross-sectional view of the transfer valve and valve motor;

FIG. 14 is a partial cross-sectional view of the waste collection unit illustrating the pocket doors;

FIG. 15 is a close-up view of the upper pocket door shown in the cross-sectional view of FIG. 14;

FIG. 40A is a perspective view of a display that is able to rotate and tilt relative on the waste collection unit;

FIG. 52 is a front perspective view of the head of the docking station;

FIG. 53 is a top view of the head of the docking station;

FIG. 54 is a rear view of the head of the docking station;

FIG. 55 is a cross-sectional view of the head of the docking station;

DETAILED DESCRIPTION OF THE INVENTION

I. Overview

Referring to the Figures, wherein like numerals indicate like or corresponding parts throughout the several views, a waste collection and disposal system for collecting and disposing of waste materials is shown generally at 100. The system 100 collects and disposes of waste material generated during medical procedures (e.g., surgical procedures) performed in a health care facility such as a hospital. The waste material may include bodily fluids, body tissues, irrigation liquids, and/or other materials that may be generated during various medical procedures. Often times, medical procedures require large amounts of saline and/or other irrigation liquids for irrigating an anatomical site. As a result, the system 100 is capable of handling large amounts of waste material.

Figure 1:
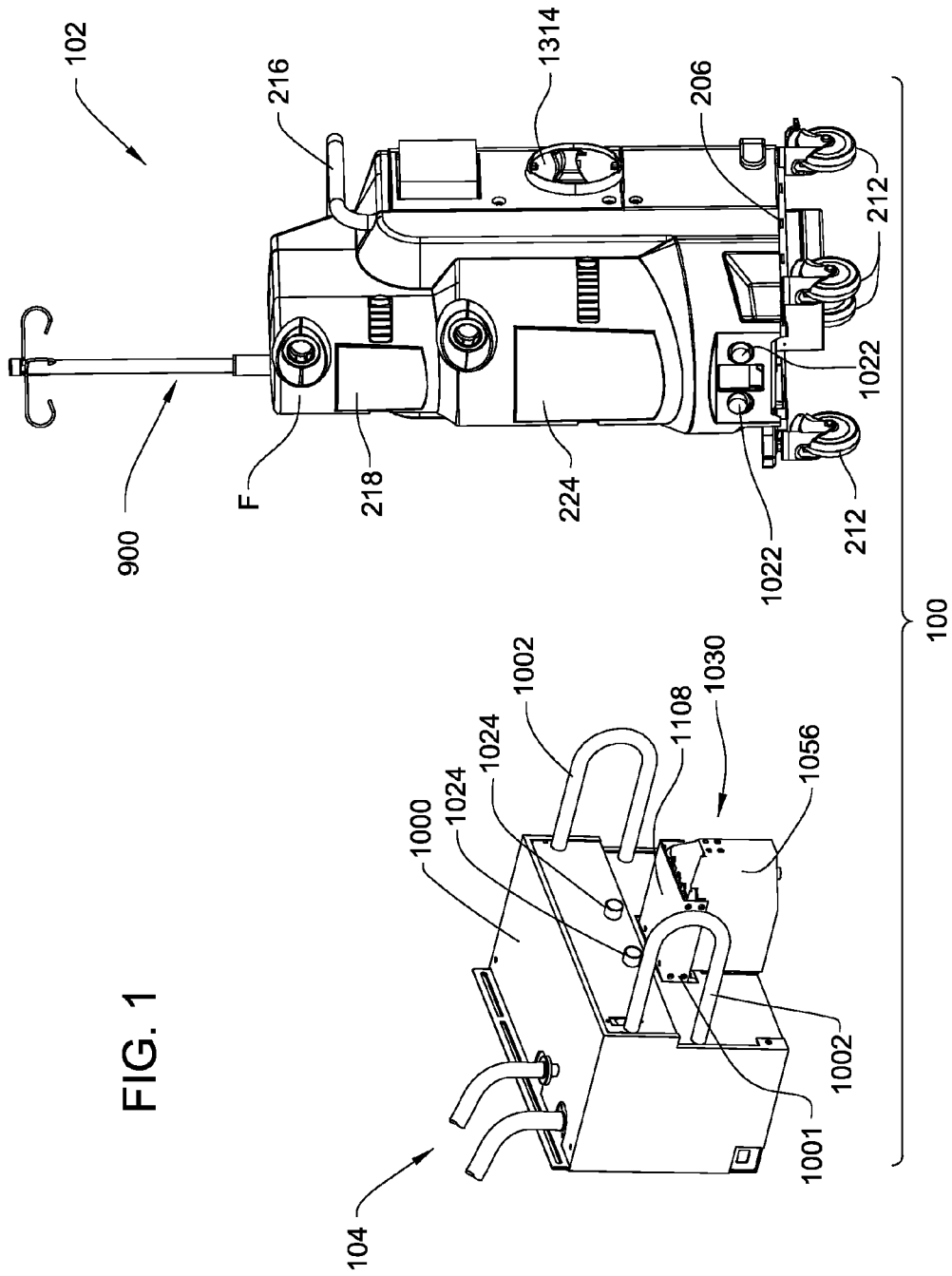
FIG. 1 is a perspective view of a waste collection and disposal system of the present invention illustrating a waste collection unit and a docking station of the system.

Referring to FIG. 1, the system 100 comprises a mobile waste collection unit 102 and a fixed docking station 104. The waste collection unit 102 collects the waste material generated during the medical procedures. For convenience, the waste collection unit 102 may also be referred to as a rover 102. Docking station 104 functions as the unit through which waste collected by the waste collection unit 102 is discharged for treatment. For convenience, the docking station 104 may also be referred to as a docker 104. The docking station 104 also functions to clean the waste collection unit 102, as explained further below. During use, the waste collection unit 102 collects the waste material and stores the waste material on-board until such a time as a user is ready to off-load the waste material and dispose of the waste material. In the embodiments shown, the waste collection unit 102 is capable of storing waste material from a series of different medical procedures during the course of a day or across several days, without requiring off-loading of the waste material. Once the waste material either fills the waste collection unit 102, or the user is ready to dispose of the waste material, the waste collection unit 102 is wheeled to the docking station 104 by the user. At the docking station 104, the waste material is emptied from the waste collection unit 102 to a waste drain D or treatment area, and the waste collection unit 102 is cleaned for further use.

The system 100 includes various features for simplifying use by health care personnel including doctors, nurses, and other users of the system 100, and for improving patient outcomes from the various medical procedures. Some of the features were designed to increase the on-board waste material storage of these types of systems and to increase the number of uses prior to requiring disposal of the waste material. Other features were designed to reduce the overall time needed by users to collect and dispose of the waste material, to improve volumetric estimations of the waste material collected, and to create cleaner and more inconspicuous docking between the waste collection unit 102 and the docking station 104. Still other features were designed to simplify smoke removal, to reduce the noise typically experienced when operating such systems, and to improve the odors that often accompany such systems. All of these features are described in detail below.

II. Stacked Waste Containers

Figure 2:
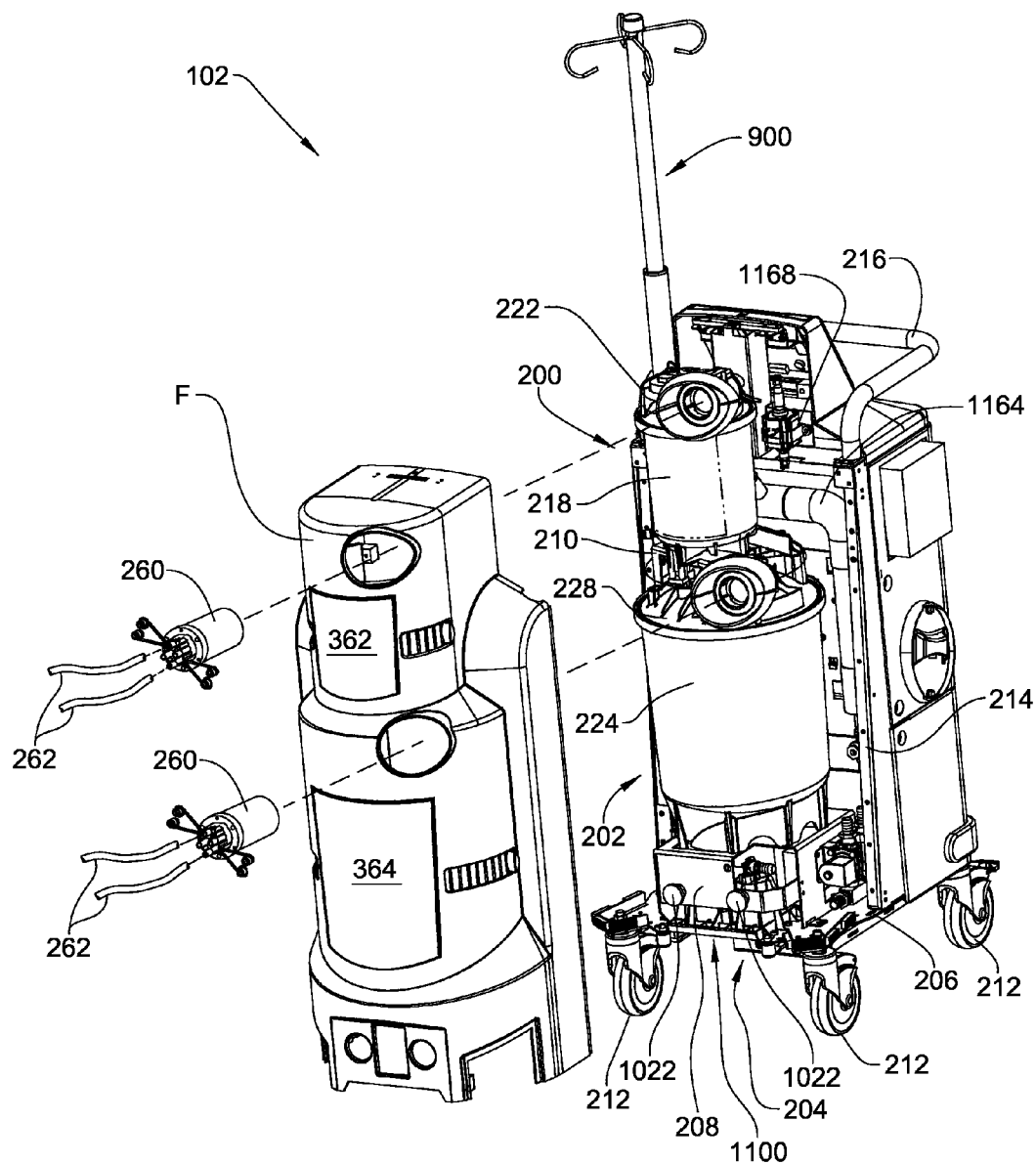
FIG. 2 is perspective view of the waste collection unit with a front cover removed to reveal upper and lower waste containers.

Referring to FIG. 2, the waste collection unit 102 utilizes upper 200 and lower 202 waste containers to collect and temporarily store the waste material during use. A cart 204 supports the waste containers 200, 202. More specifically, the waste containers 200, 202 are stacked one above the other on the cart 204. The cart 204 includes a cart base 206 with a lower frame 208 having a generally box shape. The lower frame 208 supports the lower waste container 202. The lower frame 208 is mounted to a top of the cart base 206. An upper frame 210 supports the upper waste container 200. The upper frame 210 mounts to the lower waste container 202.

A plurality of wheels 212 are mounted to a bottom of the cart base 206 to provide mobility to the cart 204. A vertical chassis 214 is fixed to the cart base 206 and extends upwardly from the cart base 206. A handle 216 is mounted to the vertical chassis 214 to facilitate movement of the waste collection unit 102 between use areas, and between the use areas and the docking station 104. Thus, users can move the cart 204 around the health care facility to collect waste material generated during medical procedures performed in different locations throughout the health care facility. A front cover F, removed to show the waste containers 200, 202 in FIG. 2, mounts to the cart base 206 and the vertical chassis 214 to conceal internal components of the waste collection unit 102. The front cover F is preferably formed of a plastic material. Transparent windows 362, 364 (see FIG. 2) are present in openings in the front cover F to allow viewing of the canisters 218, 224 and their contents.

Referring to FIGS. 2 and 3, the upper waste container 200 comprises an upper canister 218 that is slightly frusto-conical in shape, but appears generally cylindrical. The upper canister 218 defines an upper waste chamber 220 for holding waste material. An upper cap 222 covers the upper canister 218 to close the upper waste chamber 220. The lower waste container 202 comprises a lower canister 224 that is also slightly frusto-conical in shape. The lower canister 224 defines a lower waste chamber 226 for holding waste material. A lower cap 228 covers the lower canister 224 to close the lower waste chamber 226. The canisters 218, 224 may assume any shape that is suitable for containing the waste material. The caps 222, 228 are preferably formed of a polymeric material such as plastic and have external and internal surfaces. Structural support members 225 are formed on the external surfaces of the caps 222, 228 to provide further rigidity to the caps 222, 228 and prevent collapse. Conversely, the opposing internal surfaces of the caps 222, 228 are free of any structural support members 225 to provide a smooth, uninterrupted internal surface for easier cleaning.

The upper canister 218 is preferably smaller in diameter and storage volume than the lower canister 224 to provide a relatively better estimation of the volume of waste material collected in the upper canister 218 as compared to the lower canister 224. Preferably, the upper canister 218 has a maximum storage volume of from about 0.5 liters to about 10 liters, more preferably from about 2 liters to about 7 liters, and most preferably from about 2 liters to about 6 liters. In the embodiment shown, the maximum storage volume of the upper canister 218 is 4 liters. Preferably, the lower canister 224 has a maximum storage volume of from about 10 liters to about 50 liters, more preferably from about 15 liters to about 30 liters, and most preferably from about 18 liters to about 25 liters. In the embodiment shown, the maximum storage volume of the lower canister 224 is about 20 liters. The maximum storage volume is the amount of waste material that can be stored in each of the canisters 218, 224 before an electronic or mechanical shutoff prevents further filling of the canisters 218, 224. In alternative embodiments, the canisters 218, 224 may be placed side-by-side on the cart 204 and the canisters 218, 224 may both be large or both be small, or additional canisters (not shown) could be employed.

The upper canister 218 is disposed above the lower canister 224 on the cart 204 with respect to gravity such that the waste material collected in the upper canister 218 can be emptied into the lower canister 224 via gravity. Given the relatively small maximum storage volume of the upper canister 218, the waste material collected in the upper canister 218 can be emptied several times into the lower canister 224 without filling the lower canister 224 beyond its maximum storage volume. In some embodiments, the maximum storage volume of the lower canister 224 is greater than twice the maximum storage volume of the upper canister 218 such that the waste material collected in the upper canister 218 can be emptied at least twice into the lower canister 224 before the lower canister 224 is filled to its maximum storage volume.

Referring specifically to FIG. 3, each of the canisters 218, 224 may be formed of glass or suitable plastic materials. Each of the canisters 218, 224 includes a bottom 230, 232, respectively. An outer wall 234, 236, respectively, extends upwardly from the bottom 230, 232 to secure the waste material in the canisters 218, 224 during use. Each of the outer walls 234, 236 extends upwardly from the bottom 230, 232 to an open end. An annular rim 238, 240, respectively, extends circumferentially around each of the outer walls 234, 236 at the open ends. The rims 238, 240 define grooves 242, 244. An elastomeric seal 246, 248 is disposed in each of the grooves 242, 244 to seal the caps 222, 228 to the canisters 218, 224. More specifically, each of the caps 222, 228 is generally dome-shaped with a peripheral lip 250, 252, respectively, that engages the rim 238, 240 of the canisters 218, 224 with the elastomeric seal 246, 248 trapped therebetween. A V-clamp 254, 256, respectively, secures the caps 222, 228 to the canisters 218, 224 by clamping the peripheral lips 250, 252 to the rims 238, 240.

Referring again to FIGS. 2 and 3, manifold receivers 258 are mounted to each of the caps 222, 228. The manifold receivers 258 are adapted to receive disposable manifolds 260 (see FIG. 2), which direct waste material from one or more sites in proximity to a patient, through suction lines 262, into the canisters 218, 224. Thus, the manifold receivers 258 act as one type of connecting member of the waste containers 200, 202 for connecting the suction lines 262 to the waste containers 200, 202. Two suction lines 262 are shown attached to each of the disposable manifolds 260 in FIG. 2. Of course, only one suction line 262 could be used, or additional suction lines 262 could be employed to capture waste material from the sites. The distal end of each suction line 262, the end closest to a patient is connected to a suction applicator. It is appreciated that the suction applicator is the actual surgical handpiece applied to the surgical site in order to draw waste away from the site. Some suction applicators are built into other tools, such as shavers that perform another procedure in addition to serving as the suction handpiece. The exact structure of the suction applicator is not relevant to the construction of this invention.

The disposable manifolds 260 preferably include a filter (not shown) to filter the waste material received from the suction lines 262 prior to the waste material entering the canisters 218, 224. The disposable manifolds 260 and associated filters, and their attachment to the manifold receivers 258 mounted to the caps 222, 228 are described in detail in co-pending U.S. patent application Ser. No. 11/554,616 to Murray et al., entitled, REMOVABLE INLET MANIFOLD FOR A MEDICAL/SURGICAL WASTE COLLECTION SYSTEM, THE MANIFOLD INCLUDING A DRIVER FOR ACTUATING A VALVE INTEGRAL WITH THE WASTE COLLECTION SYSTEM, filed Oct. 31, 2006, U.S. Pat. Pub. No. 2007/0135778, which is hereby incorporated by reference The manifold and receiver disclosed in this document are understood to be exemplary, not limiting with regard to the assemblies that are used to connect the suction lines 262 to the canisters 218, 224.

Figure 5:
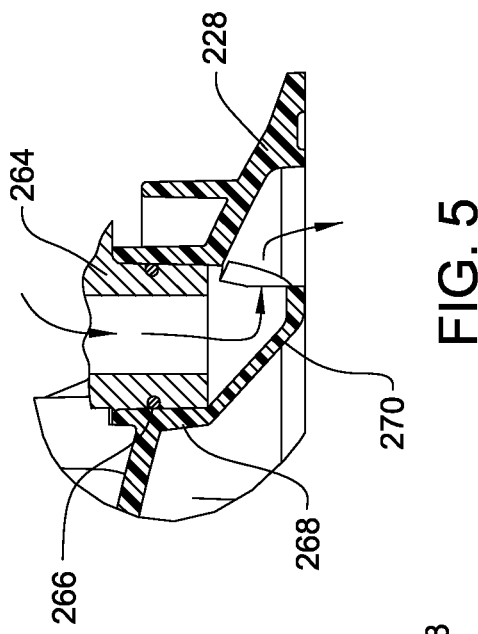
FIG. 5 is a cross-sectional view of the flow diverter.
Figure 4:
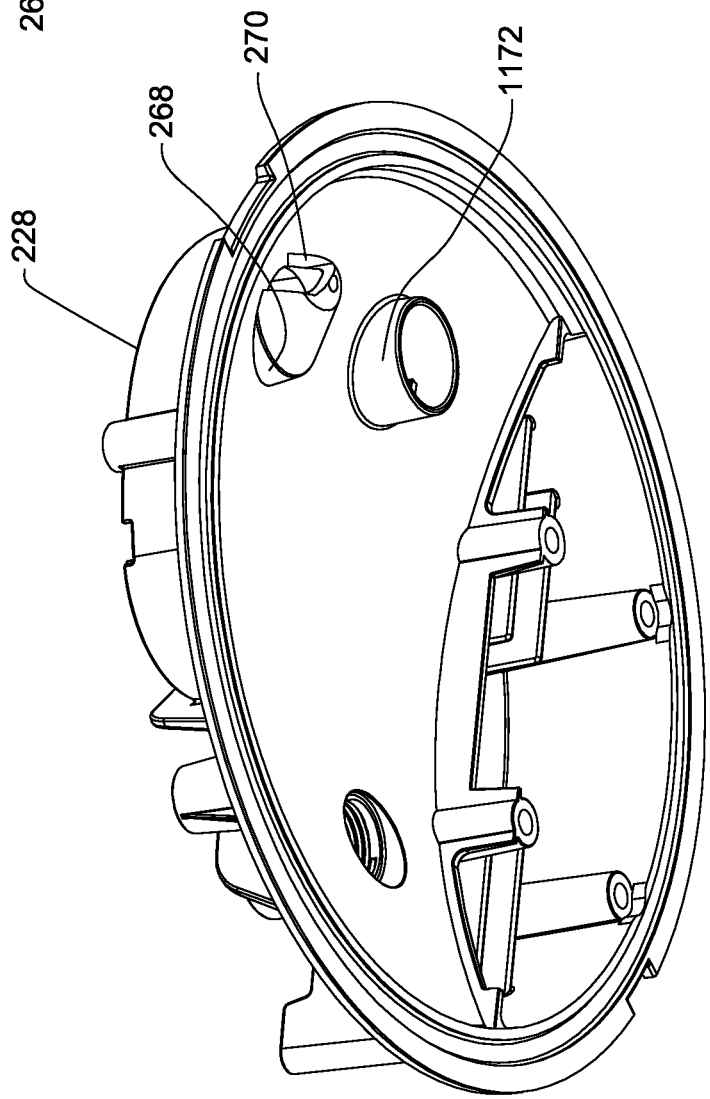
FIG. 4 is a bottom perspective view of the lower cap of the lower waste container without any components attached thereto to illustrate a flow diverter.

Referring to FIGS. 4 and 5, the lower cap 228 is shown without any of the components normally mounted thereto. Each of the manifold receivers 258 includes a boss 264 with associated o-ring 266, as shown in FIG. 4. This is also shown in application Ser. No. 11/554,616, hereby incorporated by reference. The boss 264 fits into a waste port 268 defined in the lower cap 228. A flow diverter 270 is integrally formed at a bottom of the waste port 268 to direct the flow of waste material away from a center axis of the lower canister 224 toward the outer wall 236 of the lower canister 224. The flow diversion resulting from the flow diverter 270 reduces the amount of disturbance of the liquid surface inside the lower waste container 202. This feature assists in improving the accuracy of volumetric measurement, as described further below, by reducing turbulence in the liquid surface. It should be appreciated that although only the lower cap 228 is shown, the upper cap 228 includes the same feature for accommodating a manifold receiver 258.

Figure 6:
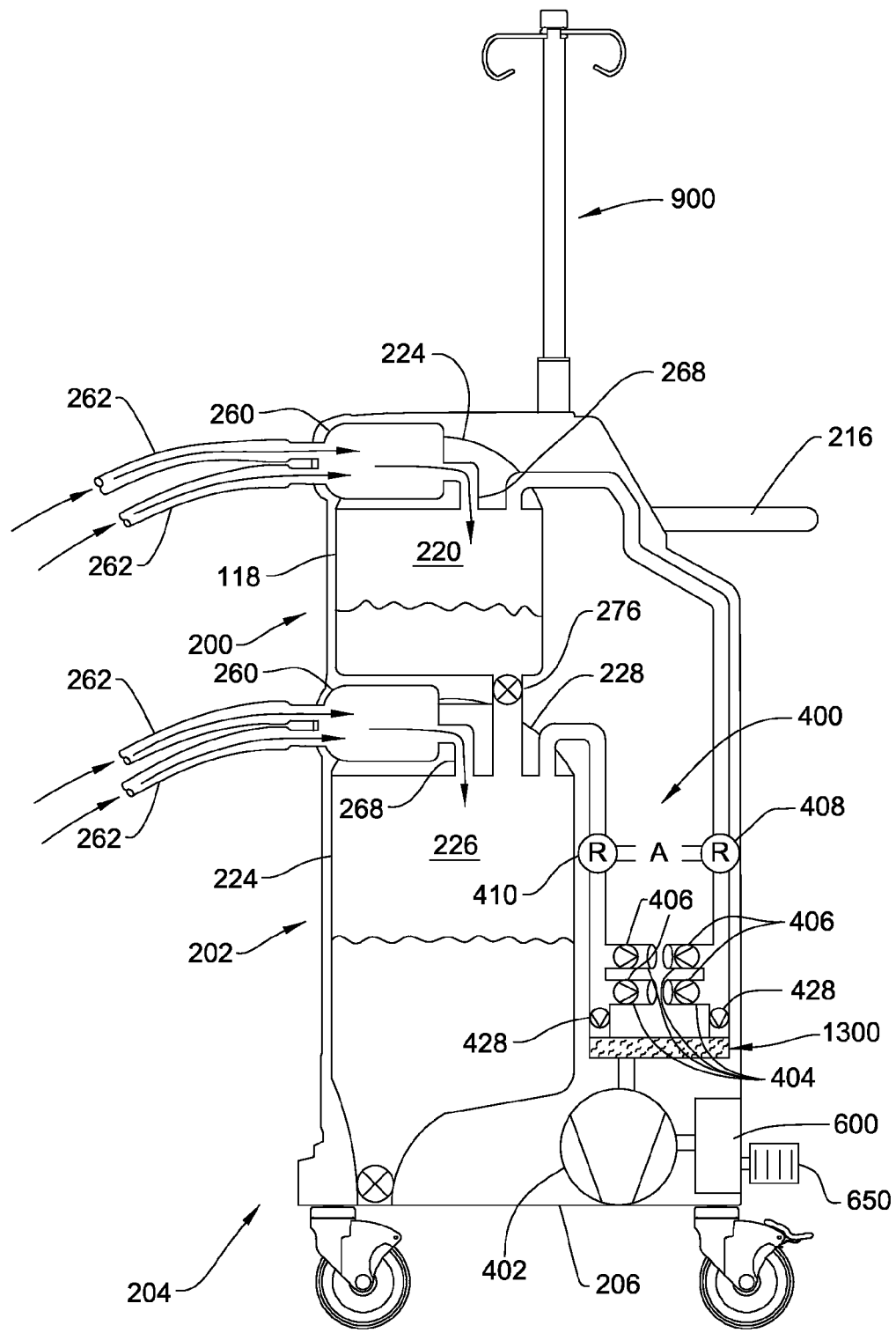
FIG. 6 is a schematic view of the waste collection unit illustrating the upper and lower waste containers and further illustrating the flow of waste material into the upper and lower waste containers and a vacuum circuit for drawing the waste material into the upper and lower waste containers.

Referring to FIG. 6, a schematic representation of waste material being collected by the waste collection unit 102 is shown. A vacuum is pulled in each of the waste containers 200, 202 with a vacuum circuit 400, described further below, to draw the waste material into the waste containers 200, 202 from the sites in proximity to the patient. With the vacuum present, waste material is drawn through the suction lines 262, disposable manifolds 260, and finally through the waste ports 268 defined in the caps 222, 228 to enter the canisters 218, 224. Users can select to simultaneously collect waste material in both waste containers 200, 202 or one at a time.

Figure 7:
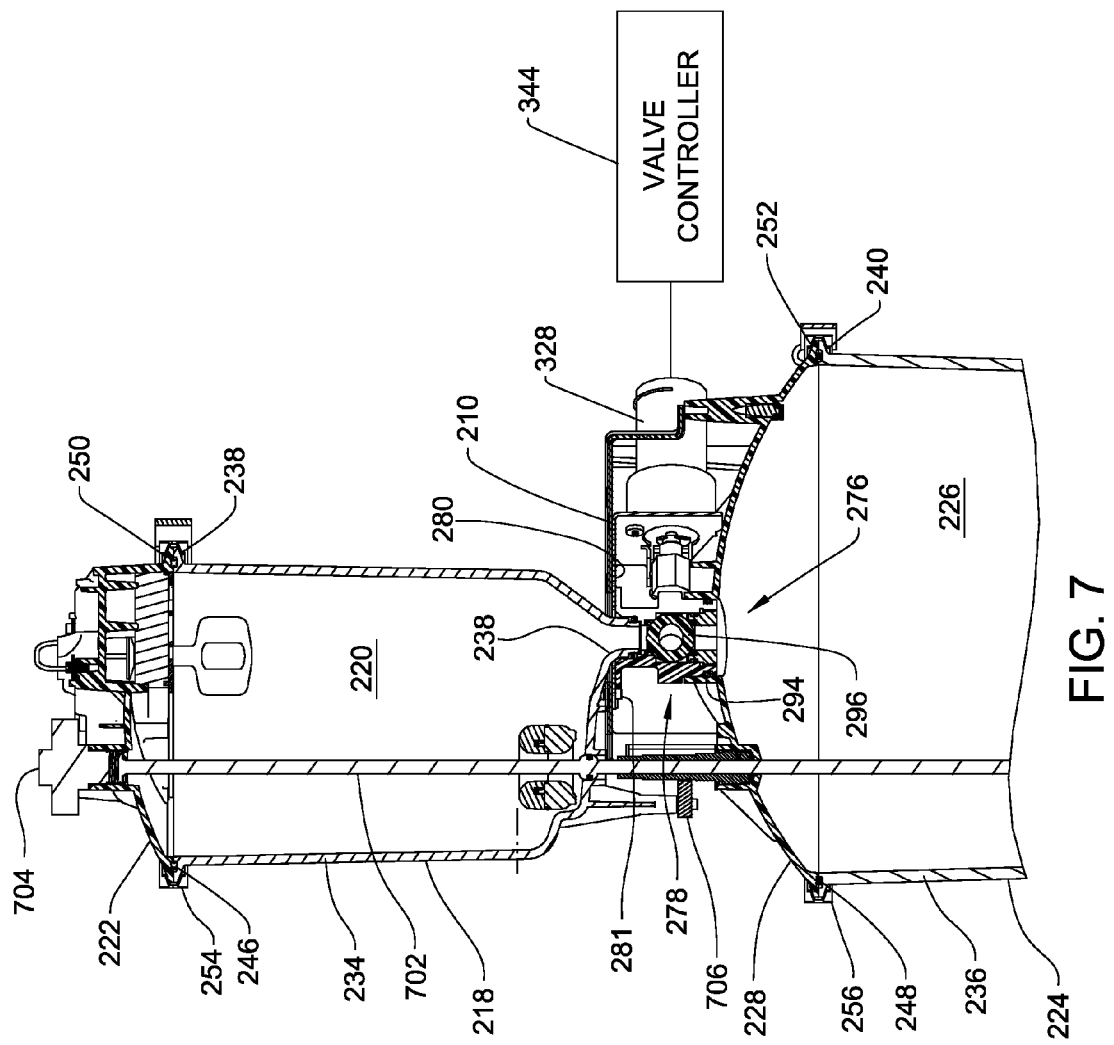
FIG. 7 is a partial cross-sectional view of the upper and lower waste containers illustrating a motor-actuated transfer valve disposed between the waste containers.

Referring to FIG. 7, a transfer valve 276 is disposed between the upper canister 218 and the lower canister 224 to facilitate emptying of the waste material from the upper canister 218 to the lower canister 224 via gravity. The transfer valve 276 is selectively closed to retain cleaning fluid in the upper canister 218 during cleaning (described further below). The transfer valve 276 is also selectively closed to seal the vacuum path between the waste containers 200, 202 to allow independent vacuum regulation (also described further below). The transfer valve 276 moves between open and closed positions. In the open position, the waste material that was present in the upper canister 218 drains, under the force of gravity, to the lower canister 224. In the closed position, the waste material is retained in the upper canister 218. The transfer valve 276 is preferably in the form of a ball valve. With this feature, the upper canister 218 can be emptied and readied for continued use between medical procedures without requiring off-board disposal of the waste material. This reduces the number or trips that a user has to make between the use areas (e.g., operating rooms), in which the waste material is being collected, and the docking station 104, which is typically located outside of the use areas, usually near the waste drain D.

Figure 8:
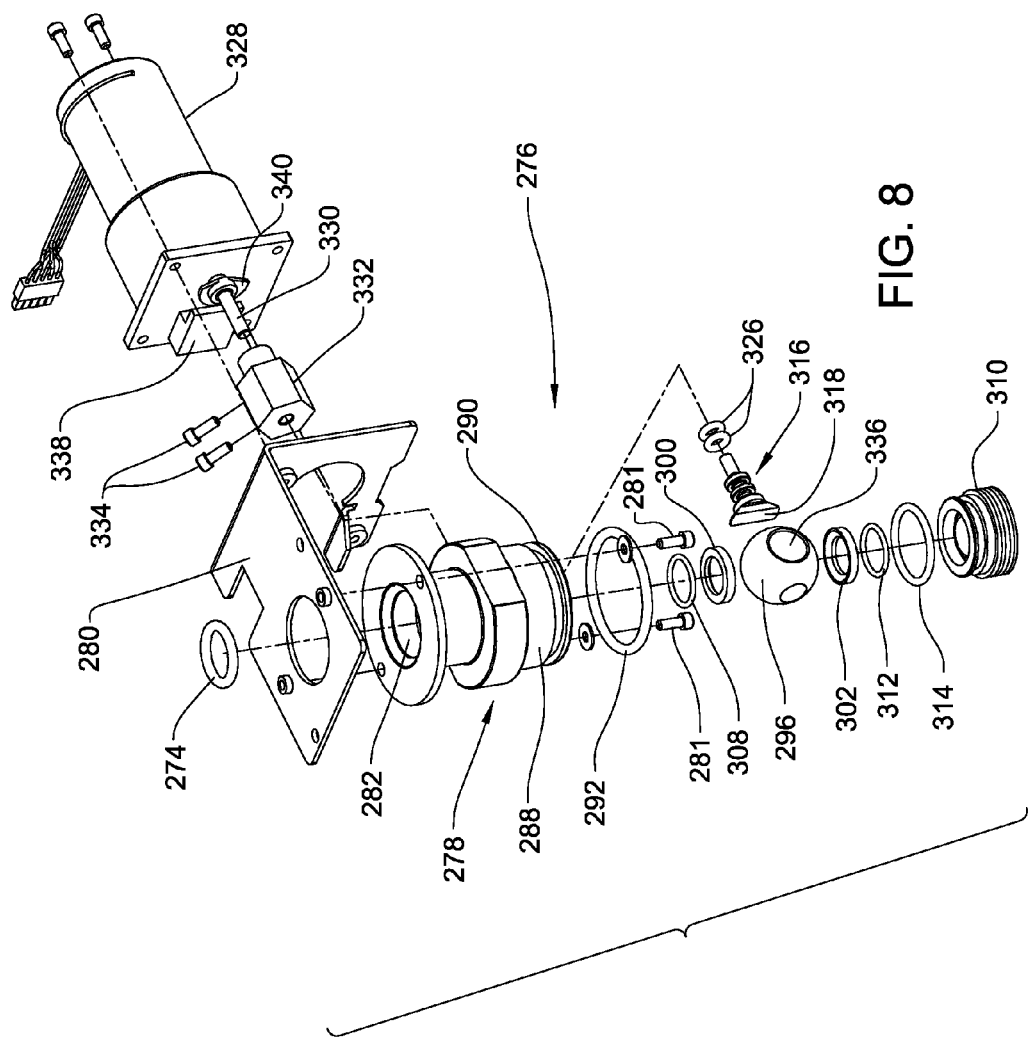
FIG. 8 is an exploded perspective view of the transfer valve and valvemotor.

Referring to FIGS. 8 through 10, the transfer valve 276 includes a valve body 278 mounted to a bracket 280. In one embodiment, the valve body 278 is formed of polyvinylchloride or polypropylene. Fasteners 281 secure the valve body 278 to the bracket 280. The bracket 280 is fixed to the upper frame 210 that supports the upper waste container 200. The valve body 278 defines an upper cavity 282 for receiving a neck 286 of the upper canister 218 (see FIG. 7). The neck 286 is integrally formed with the bottom 230 and the outer wall 234 of the upper canister 218 and extends downwardly from the bottom 230. As shown in FIG. 10, an o-ring 274 seals the neck 286 in the upper cavity 282. The valve body 278 also includes a lower portion 288. The lower portion 288 has an outer surface defining a groove 290. The lower portion 288 is adapted to seat in a valve port 294 integrally formed in the lower cap 228. An o-ring 292 seals the lower portion 288 in the valve port 294.

A ball 296 is seated in a main chamber 298 of the valve body 278. In one embodiment, the ball 296 is formed of polyvinylchloride or polypropylene. The ball 296 is supported in the main chamber between first 300 and second 302 valve seats. The valve seats 300, 302 are annular in shape and include a slightly concave face to receive the ball 296 in a tight sealing manner. The first valve seat 300 abuts an internally facing annular shoulder 304 forming an upper boundary of the main chamber 298. The annular shoulder 306 defines a downwardly facing groove facing into the main chamber 298. An o-ring 308 is seated in the downwardly facing groove to seal the first valve seat 300 to the valve body 278. A nut 310 screws into the lower portion 288 to secure the ball 296 in the valve body 278. In one embodiment, the nut 310 is formed of polyvinylchloride or polypropylene. The second valve seat 302 is captured between the nut 310 and the ball 296. The nut 310 defines an upwardly facing groove and a radially outwardly facing groove. An o-ring 312 is seated in the upwardly facing groove to seal the nut 310 against the second valve seat 302. Another o-ring 314 is seated in the radially outwardly facing groove to seal the nut 310 against an interior of the valve body 278.

A valve stem 316 is coupled to the ball 296 to rotate the ball 296. The ball 296 defines a stem pocket and the valve stem 316 includes a stem head 318 corresponding in shape to the stem pocket. The stem head 318 is elongated in one dimension. When the stem head 318 mates with the stem pocket, the stem head 318 is rotatably fixed to the ball 296. The ball 296 and stem head 318 form a complete ball shape when engaged together. The stem head 318 includes a first annular shoulder 320. The valve stem 316 extends from the annular shoulder 320 to a far end opposite the stem head 318. The valve body 278 defines a generally cylindrical sleeve 322 for receiving the valve stem 316. The sleeve 322 includes a second annular shoulder 324 that abuts the first annular shoulder 320 to prevent the valve stem 316 from popping out of the main chamber 298 through the sleeve 322. The valve stem 316 extends from the ball 296 in the main chamber 298 through the sleeve 322 to the far end. The valve stem 316 is generally cylindrically and is rotatably supported in the sleeve 322. O-rings 326 seal the valve stem 316 in the sleeve 322.

A transfer valve motor 328 is operatively coupled to the transfer valve 276 to move the transfer valve 276 between the open position in which fluid communication is opened between the canisters 218, 224 and the closed position in which fluid communication between the canisters 218, 224 is closed. The valve motor 328 is mounted to the bracket 280. The valve motor 328 includes a motor shaft 330 rotationally coupled to the far end of the valve stem 316 via a coupler 332. Fasteners 334 secure the coupler 332 to the far end of the valve stem 316 and the motor shaft 330. The motor shaft 330 rotates the ball 296 to move the transfer valve 276 between the open and closed positions. The ball 296 includes a through opening 336 that aligns with passages in the neck 286 of the upper canister 218 and the valve port 294 of the lower cap 228 in the open position. The through opening 336 is normal to the passages of the neck 286 and the valve port 294 in the closed position such that the ball 296 seals the neck 286 from the valve port 294. The closed position is shown in FIG. 10.

Figure 11:
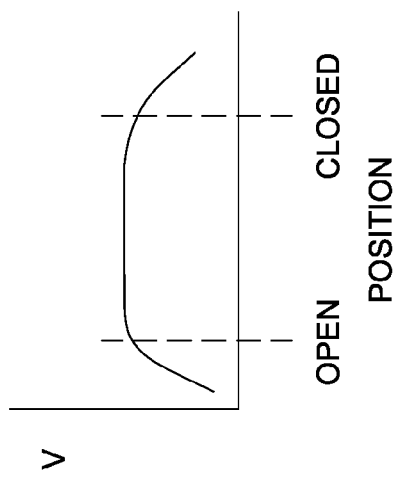
FIG. 11 is a graph illustrating a position signal generated by a position sensor associated with the valve motor.

A position sensor 338 responds to movement of the transfer valve 276 between the open and closed positions to sense a current position of the transfer valve 276. In the preferred embodiment, a single position sensor 338 is utilized to generate a position signal that follows a generally non-linear voltage path between the open and closed positions, as shown in FIG. 11. For instance, in the open position, the position signal is climbing a steep slope, while in the closed position the position signal is falling down a steep slope. The position sensor 338 is preferably a hall-effect sensor that detects rotation of a metallic sensing plate 340, formed of carbon steel in one embodiment. In the preferred embodiment, the sensing plate 340 has a cammed shape (see also FIG. 8). This cammed shape generates the position signal voltage path shown in FIG. 11 between the open and closed positions. It should be appreciated that other position sensors such as contact switches could alternatively be placed to sense when the transfer valve 276 is at the open and/or closed positions.

Figure 12:
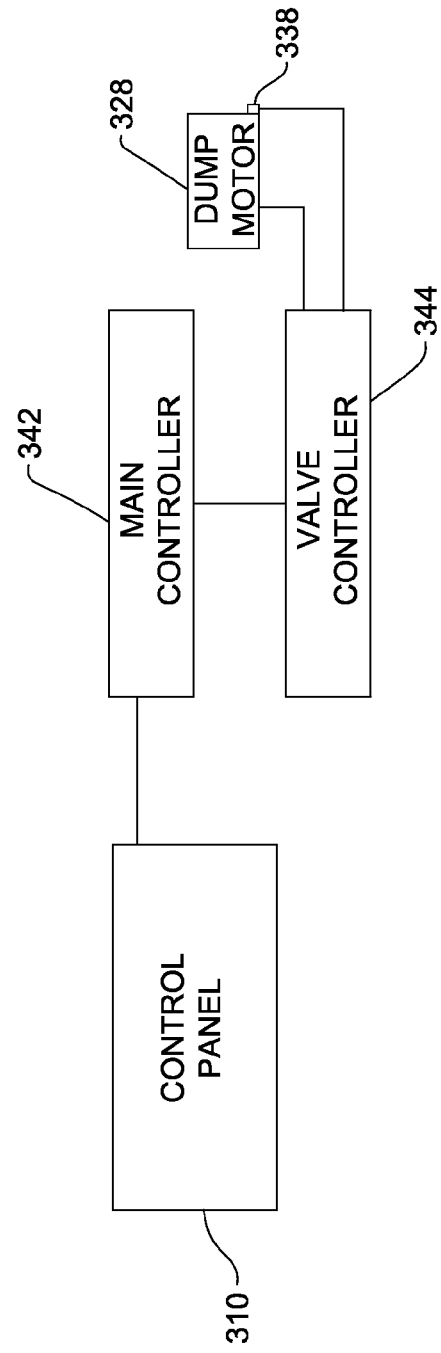
FIG. 12 is a block diagram of the transfer valve and associated controls.

Referring to the block diagram of FIG. 12, a main controller 342 operates the waste collection unit 102. The main controller 342 includes a plurality of sub-controllers (with their own microprocessors, memory, etc.) that operate specific features of the waste collection unit 102. The sub-controllers may communicate with the main controller 342 along a communications bus or by other conventional methods. One of the sub-controllers is a valve controller 344. The valve controller 344, including appropriate microprocessors, controls valve motor 328 to move the transfer valve 276 between the open and closed positions as needed. An on-board control panel 310 is in communication with the main controller 342 to allow user selected operation of the valve motor 328. In one such operation, the user may select to transfer the waste material from the upper canister 218 to the lower canister 224 by actuating a pushbutton 348 (see FIG. 40) or other suitable user-selectable control of the control panel 310. The user can request dumping at any time during use such as when the upper canister 218 is full, or simply when the user desires an empty upper canister 218.

When waste transfer is required, the main controller 342 is programmed to first instruct the valve controller 344 to instruct the valve motor 328 to move the transfer valve 276 to the open position to empty the waste material into the lower canister 224. The valve motor 328 is then automatically instructed to move back to the closed position once upper canister 218 emptied, as determined by a fluid measuring system described further below, or by monitoring time and closing the transfer valve 276 after the time typically associated with transferring waste from a full upper canister 218 has elapsed. The position signal generated by the position sensor 338 is transmitted to the valve controller 344 to control this operation. With the opposing steep slopes of the voltage path generated by the position signal at the open and closed positions, the valve controller 344 can quickly determine which position the transfer valve 276 is in.

In some instances, the main controller 342 may automatically instruct the valve controller 344 to move the transfer valve 276 without requiring user instruction. This is particularly true during a cleaning cycle, described further below, in which the main controller 342, via the valve controller 344, selectively opens and closes the transfer valve 276 to drain, clean, and rinse the waste containers 200, 202.

Figure 13:
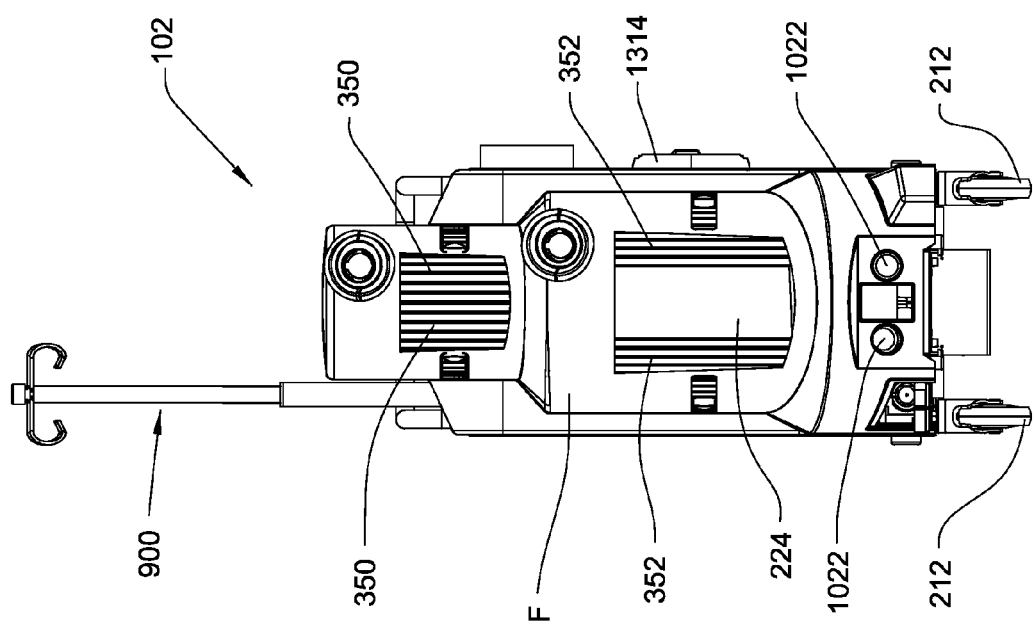
FIG. 13 is a front view of the waste collection unit illustrating upper pocket doors in a closed position and lower pocket doors in a partially open position.

Referring to FIGS. 13 through 15, upper 350 and lower 352 pocket doors (or covers) selectively conceal and reveal the upper 218 and lower 224 canisters during use. This is particularly advantageous when wheeling the waste collection unit 102 down hallways in the health care facility in which other patients or family members may be present. The pocket doors 350, 352 allow the user to conceal the canisters 218, 224 to prevent others from seeing the potentially offensive waste material contained therein. Referring specifically to FIG. 15, the pocket doors 350, 352 slide in upper 354 and lower 356 tracks. The tracks 354, 356 are fixed to an interior of the front cover F by an adhesive or may be integrally formed in the front cover F. Thus, the tracks 354, 356 are arcuate in shape along their length. The canisters 218, 224 can be viewed through the transparent windows 362, 364 (see FIG. 2) when the pocket doors 350, 352 are open.

Still referring to FIGS. 14 and 15, the upper pocket door 350 is shown in more detail. The upper pocket door 350, which is of the same construction as the lower pocket door 352, includes inner 366 and outer 368 plastic panels. The panels 366, 368 are crimped together from top to bottom at predetermined spaces to form a plurality of hinges 369 (see FIG. 14). These hinges 369 allow the pocket doors 350, 352 to bend along the arcuate shaped tracks 354, 356 when sliding between open and closed positions. In other embodiments, a single arcuate panel may be employed to slide in the tracks 354, 356. Ball bearings or other suitable bearing mechanisms could be employed to facilitate sliding of the pocket doors 350, 352 in the tracks 354, 356.

A plastic or foam intermediate layer 370 may be sandwiched between the panels 366, 368 in the sections between the hinges 369, as shown in FIG. 15. The panels 366, 368 may be glued to the intermediate layer 370 with an adhesive. The intermediate layer 370 helps to provide some thickness to the pocket doors 350, 352 while also reducing the weight of the pocket doors 350, 352 and maintaining flexibility in the pocket doors 350, 352. A knob 372 is mounted through the upper pocket door 314 via a fastener 374. The user grasps the knob 372 to slide the upper pocket door 314 along its upper 354 and lower 356 tracks between the open and closed positions. In other embodiments, similar doors or covers for concealing the canisters 218, 224 may be hinged or snap-fit in place, or mounted in any other configuration that achieves the purpose of concealing the canisters 218, 224 from view or exposing the canisters 218, 224 when desired by the user.

Figure 16:
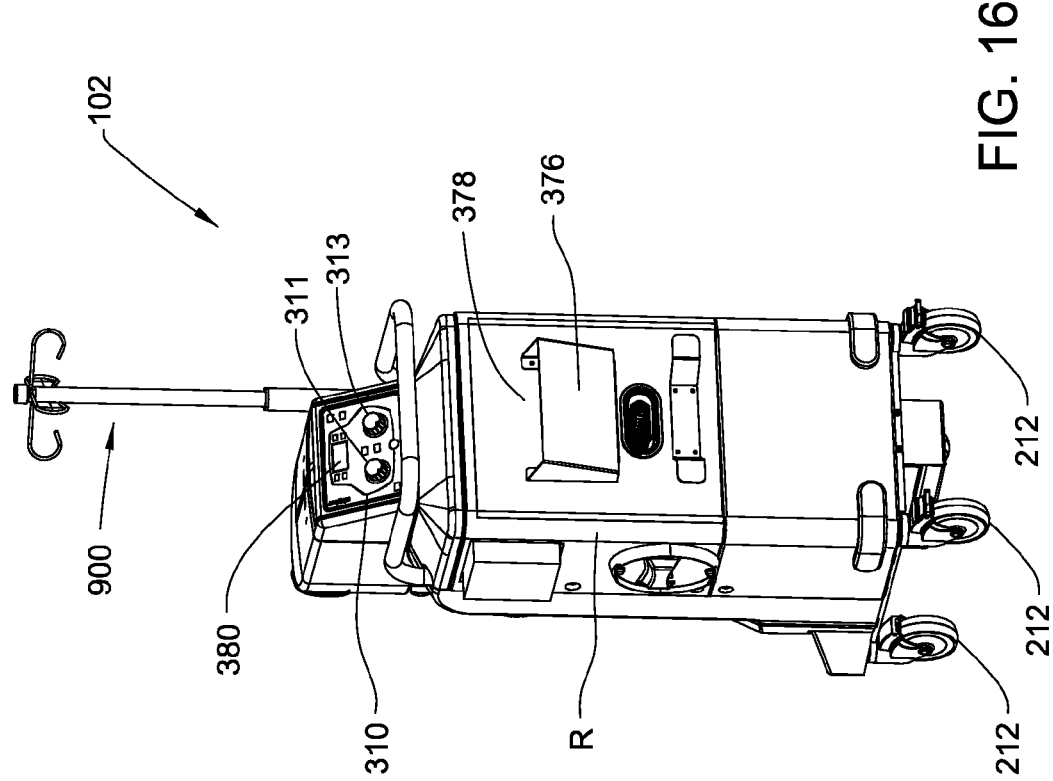
FIG. 16 is a rear perspective view of the waste collection unit.

Referring to FIG. 16, a rear perspective view of the waste collection unit 102 is shown. A storage bracket 376 defining a storage compartment 378 is shown for storing clipboards, patient charts, disposable manifolds 260, and the like. The storage bracket 376 is mounted to a rear cover R of the waste collection unit 102. It should be appreciated that the rear cover R could include multiple, independent panels, or be a single enclosure. For instance, the rear cover R may include two U-shaped sheet metal panels surrounding the back of the waste collection unit 102, one that includes a pair of bumpers, and one that includes the storage bracket 376. The rear cover R may also include a third plastic cover with a beveled shape that carriers the control panel 310. Like the front cover F, the rear cover R is also mounted to the cart base 206 and the vertical chassis 214 (the separate panels could be mounted separately to the vertical chassis 214). A control panel display 380 is shown on the control panel 310 to provide readouts for operation of the waste collection unit 102, as described further below. The control panel display 380 may be a liquid crystal-type (LCD), but other types of displays are known to those skilled in the art. The control panel 310 and control panel display 380 are electronically coupled to the main controller 342 of the waste collection unit 102.

III. Vacuum Circuit

Figure 17:
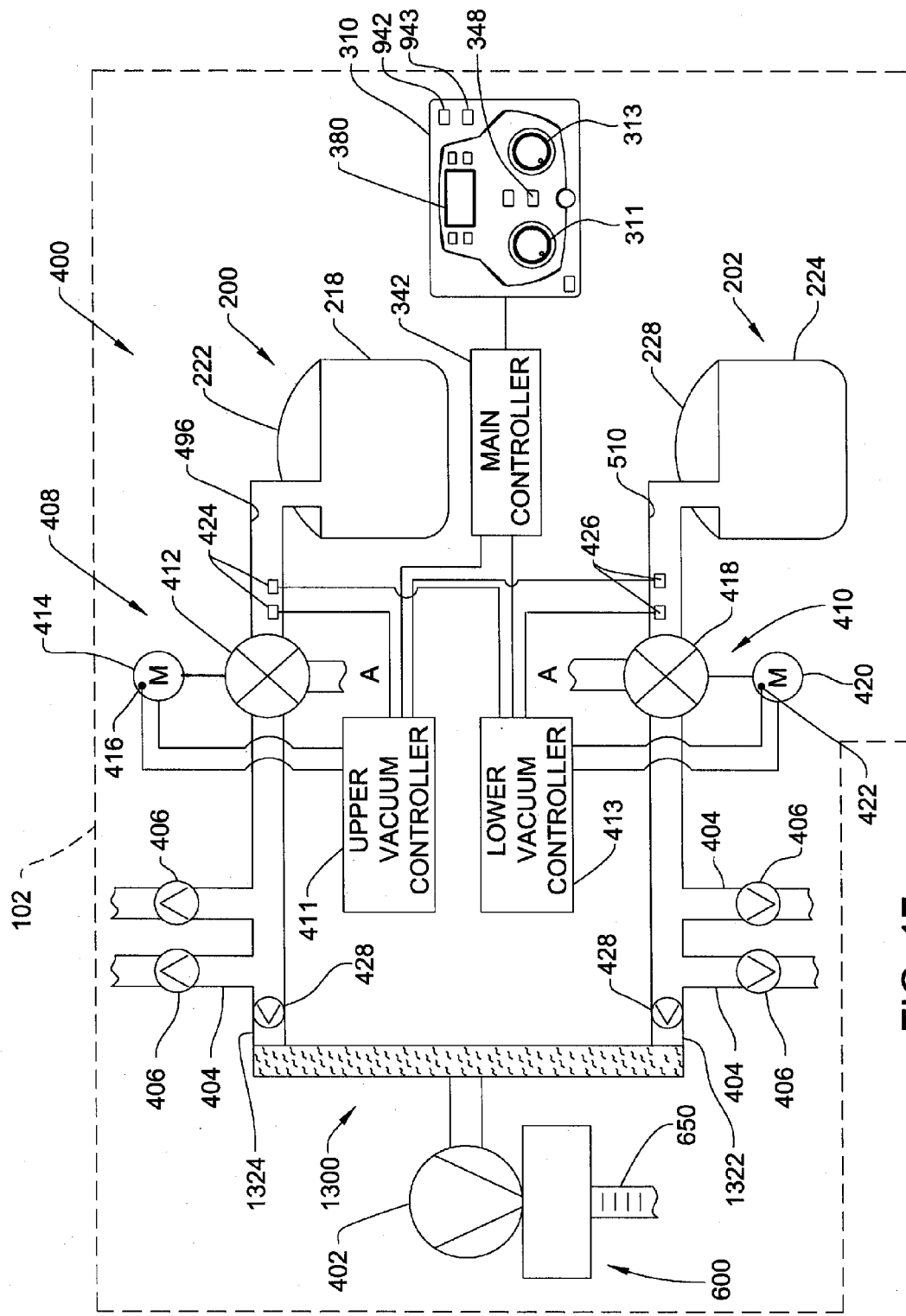
FIG. 17 is a fluid and electrical schematic view of the vacuum circuit of the waste collection unit.

Referring to FIGS. 6 and 17, the vacuum circuit 400 is shown. The vacuum circuit 400 forms part of a vacuum control assembly (or vacuum regulating assembly) that provides independently controllable vacuum levels in each of the waste containers 200, 202. As a result, the user can establish different vacuum levels for the waste containers 200, 202 depending on the particular needs of the medical procedure being performed. The vacuum circuit 400 comprises a vacuum source 402 for providing the vacuum available to the waste containers 200, 202. In some embodiments, the vacuum source 402 is a rotary vane type vacuum pump 402 mounted to the cart base 206 of the cart 204 to provide an on-board vacuum pump. One such vacuum pump 402 is a Gast 1023 Series 12 CFM rotary vane vacuum pump, Part No. 1023-318Q-G274AX, available from Gast Manufacturing, Incorporated, a unit of IDEX Corporation of Northbrook, Ill.

As shown in FIG. 17, the vacuum circuit 400 splits into parallel lines that extend from the vacuum pump 402 to the waste containers 200, 202.

In other embodiments, the vacuum source 402 may be a hospital vacuum system, located remotely from the cart 204. In the preferred embodiment, the waste collection unit 102 is outfitted with the on-board vacuum pump 402, while also providing a plurality of back-up ports 404 capable of connection to the hospital vacuum system. The back-up ports 404 can be used should the on-board vacuum pump 402 fail or should the user desire to use the hospital vacuum system in lieu of the vacuum pump 402. A check valve 406 is associated with each of the back-up ports 404 to prevent air from entering the vacuum circuit 400 through the back-up ports 404 when not in use. For simplicity, only the vacuum pump 402 shall be described below.

Referring specifically to FIG. 17, upper 408 and lower 410 vacuum regulators (also referred to as vacuum-setting valves 408, 410) are included in the vacuum circuit 400. The vacuum regulators 408, 410 are supported on the cart 204 for adjusting the vacuum levels in the waste containers 200, 202. The upper vacuum regulator 408 comprises a first valve member 412. A first actuator 414 is operatively coupled to the first valve member 412 to move the first valve member 412 and selectively open fluid communication or air transfer between the upper waste container 200 and atmospheric pressure A or between the upper waste container 200 and the vacuum pump 402. A first position sensor 416 is responsive to movement of the first valve member 412.

The lower vacuum regulator 410 comprises a second valve member 418. A second actuator 420 is operatively coupled to the second valve member 418 to move the second valve member 418 and selectively open fluid communication or air transfer between the lower waste container 202 and atmospheric pressure or between the lower waste container 202 and the vacuum pump 402. A second position sensor 422 is responsive to movement of the second valve member 418. The vacuum regulators 408, 410 are preferably configured to prevent fluid communication or air transfer between the vacuum pump 402 and atmospheric pressure A. This reduces the amount of total vacuum pressure lost during use such that a single vacuum pump 402 can provide suitable vacuum levels in both the upper 200 and lower 202 waste containers during use, even if both are being used to collect waste material simultaneously.

The main controller 342 controls operation of the vacuum regulators 408, 410 through upper 411 and lower 413 vacuum controllers (e.g., separate microcontrollers) to maintain desired vacuum levels in each of the waste containers 200, 202. Knobs or dials, 311, 313, in communication with the main controller 342, are disposed on the control panel 310 to allow the user to establish the desired vacuum levels in the waste containers 200, 202. Each of the dials 311, 313 is associated with one of the waste containers 200, 202, respectively, to control the vacuum level in the corresponding waste container 200, 202. The user may choose to shut off the vacuum inside one of the waste containers 200, 202, while maintaining a desired vacuum level in the other waste container 200, 202. Alternatively, the user may choose to set two, different vacuum levels for the waste containers 200, 202. Once the desired vacuum levels are established, the main controller 342 instructs the upper 411 and lower 413 vacuum controllers to move the vacuum regulators 408, 410 accordingly until the desired vacuum levels are reached. The control panel display 380 visually displays the current vacuum levels in each of the waste containers 200, 202.

Separate sets of pressure sensors 424, 426 are responsive to pressure changes in each of the waste containers 200, 202. The pressure sensors 424, 426 generate corresponding pressure signals sent to the vacuum controllers 411, 413. The first set of pressure sensors 424 generate pressure signals corresponding to the vacuum level in the upper waste container 200. The second set of pressure sensors 426 generate pressure signals corresponding to the vacuum level in the lower waste container 202. One of each of these sets of pressure signals 424, 426 is sent to each of the vacuum controllers 411, 413. In other words, each of the vacuum controllers 411, 413 receives one pressure signal corresponding to the vacuum level in the upper waste container 200 and one pressure signal corresponding to the vacuum level in the lower waste container 202. This redundancy allows the main controller 342 to compare pressure readings and determine whether any of the pressure sensors 424, 426 are malfunctioning or whether either of the vacuum controllers 411, 413 are malfunctioning. Accordingly, the vacuum regulators 408, 410 are controlled based on the feedback provided by the pressure signals generated by the pressure sensors 424, 426.

Additional check valves 428 are disposed between the upper vacuum regulator 408 and the vacuum pump 402 and between the lower vacuum regulator 410 and the vacuum pump 402. These check valves 428 prevent air from traveling from the vacuum pump 402 when the back-up ports 404 are being used. Otherwise, the hospital vacuum system would not be able to draw a suitable vacuum in the containers 200, 202 during use.

Figure 21:
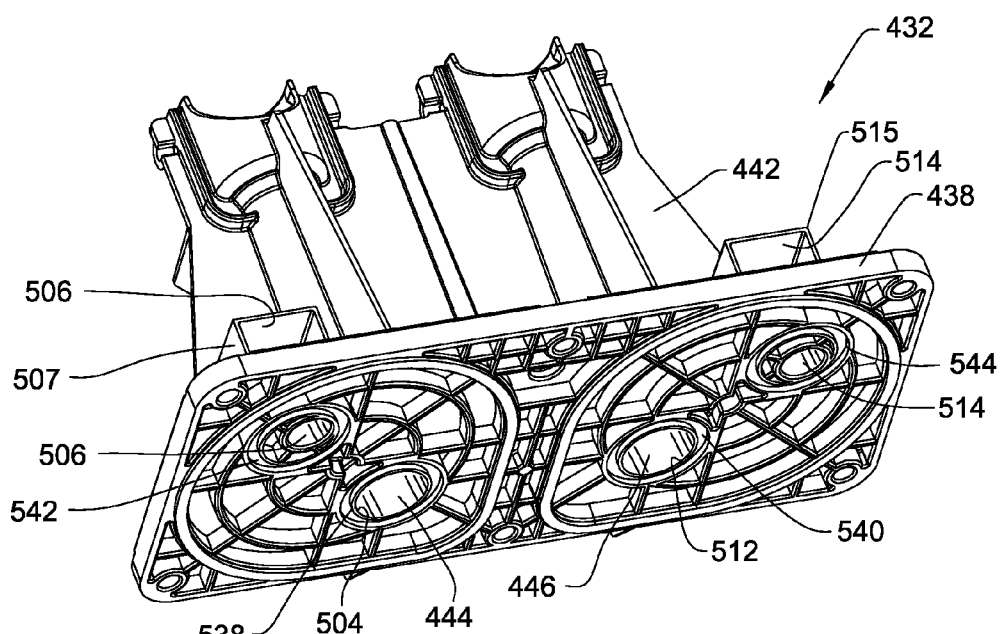
FIG. 21 is a bottom perspective view of the second housing portion.
Figure 22:
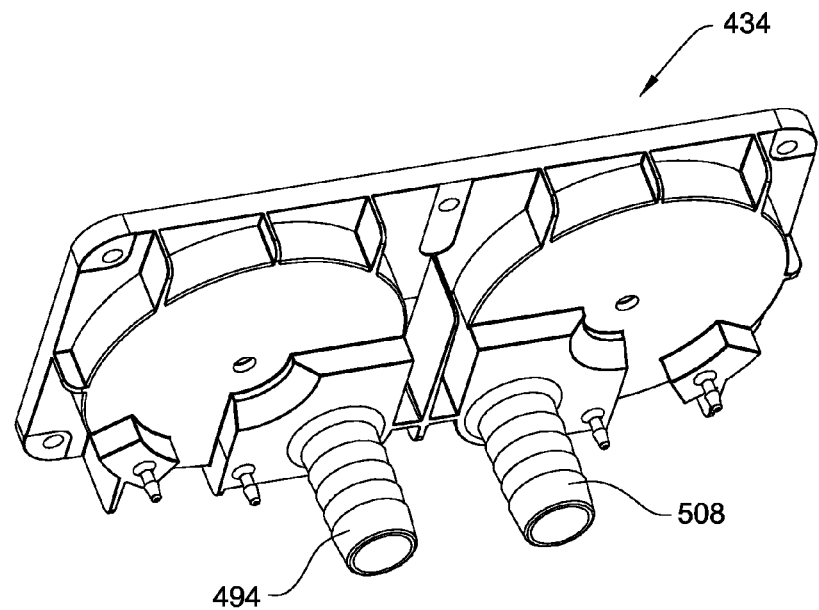
FIG. 22 is a bottom perspective view of the second housing portion.

Referring to FIGS. 18 through 27B, a vacuum manifold 430 integrates both of the vacuum regulators 408, 410 into a single unit. The vacuum manifold 430 comprises a first housing portion 432 connected to a second housing portion 434. The housing portions 432 are preferably formed of plastic materials, but may be formed of other materials including metallic materials. A plurality of fasteners 436 secures the first housing portion 432 to the second housing portion 434. The first 432 and second 434 housing portions are best shown in FIGS. 19 through 22. The first housing portion 432 includes a base section 438. First 440 and second 442 tower sections are disposed on the base section 438 and extend away from the base section 438. Referring specifically to FIG. 21, a first main passage 444 extends longitudinally and completely through the first tower section 440. A second main passage 446 extends longitudinally and completely through the second tower section 442.

Referring back to FIG. 18, two of the back-up ports 404 extend from each of the tower sections 440, 442 in selective fluid communication with the corresponding main passage 444, 446. The check valves 406 associated with the back-up ports 404 are sealed in each of the back-up ports 404 to prevent air from rushing into the corresponding main passage 444, 446 when the back-up ports 404 are not in use. The check valves 406 may be used in conjunction with port caps (not shown), but do not require port caps for their specific function. The check valves 406 may be check valve cartridges commercially available from Neoperl, Inc. of Waterbury, Conn. An example of such a check valve is shown in U.S. Pat. No. 6,837,267 to Weis et al., hereby incorporated by reference.

A nozzle plate 448 is mounted to both of the tower sections 440, 442. A plurality of fasteners 450 secures the nozzle plate 448 to the tower sections 440, 442. The nozzle plate 448 includes a plurality of tapered nozzles 452 integrally formed in the nozzle plate 448 and extending away from the back-up ports 404. The tapered nozzles 452 act as extensions of the back-up ports 404. In use, the hospital vacuum system is connected to the vacuum manifold 430 by placing hospital vacuum tubes (not shown) from the hospital vacuum system onto the tapered nozzles 452. In the preferred embodiment shown, two pairs of the tapered nozzles 452 are provided. Each pair is in fluid communication with the associated main passage 444, 446 in the tower section 440, 442 to which the back-up ports 404 are attached. As a result, during use, two separate vacuum tubes from the hospital vacuum system can be used to provide vacuum to each of the waste containers 200, 202. A pair of o-rings 454 seals the nozzle plate 448 to the back-up ports 404.

Figure 18:
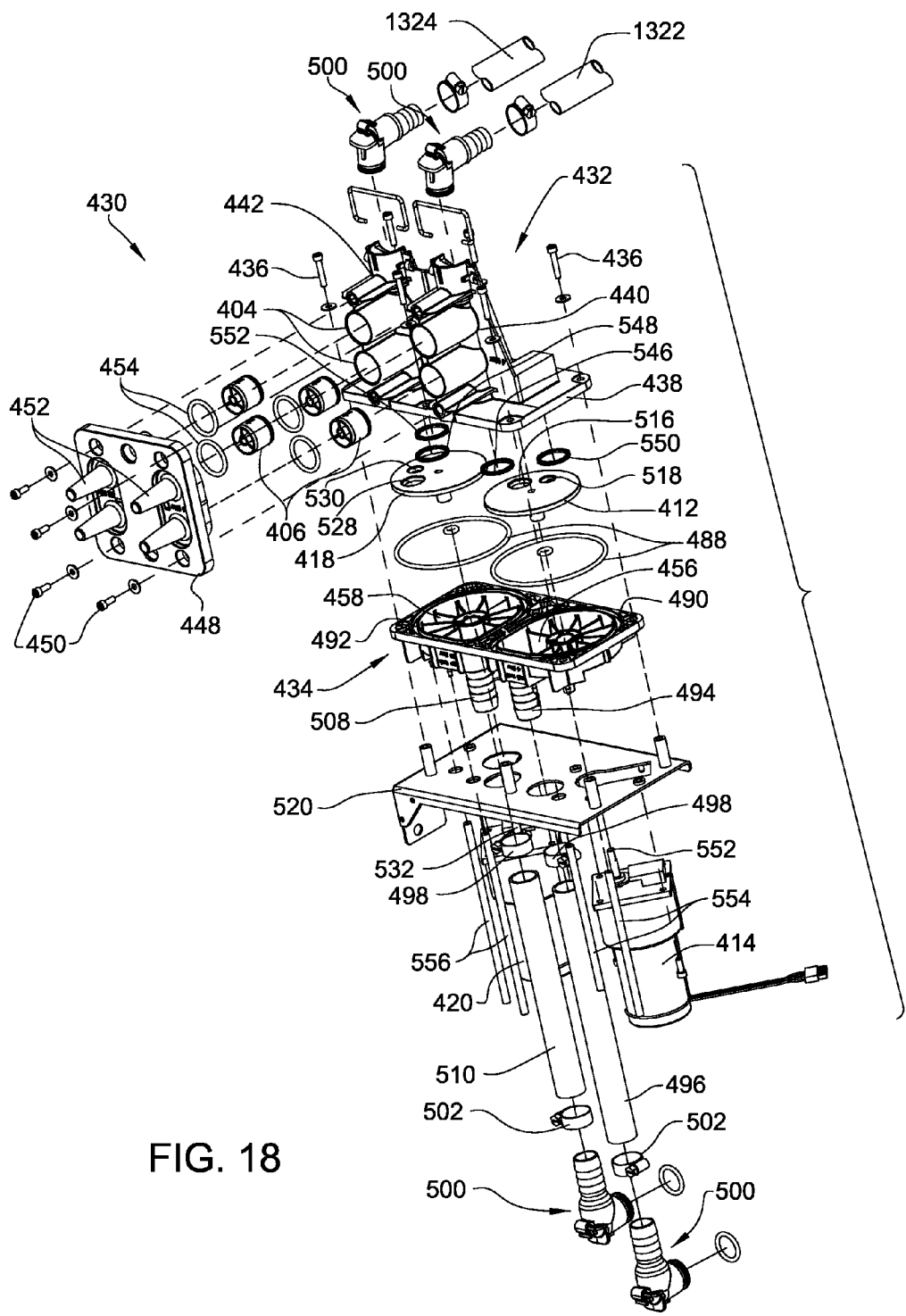
FIG. 18 is an exploded perspective view of a vacuum manifold.
Figure 19:
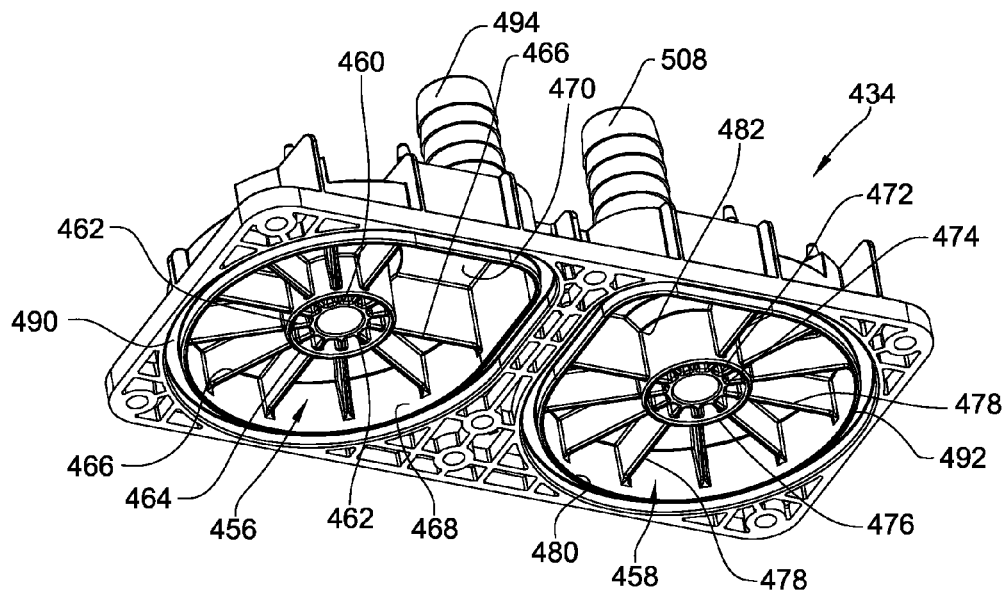
FIG. 19 is a top perspective view of a second housing portion of the vacuum manifold.
Figure 20:
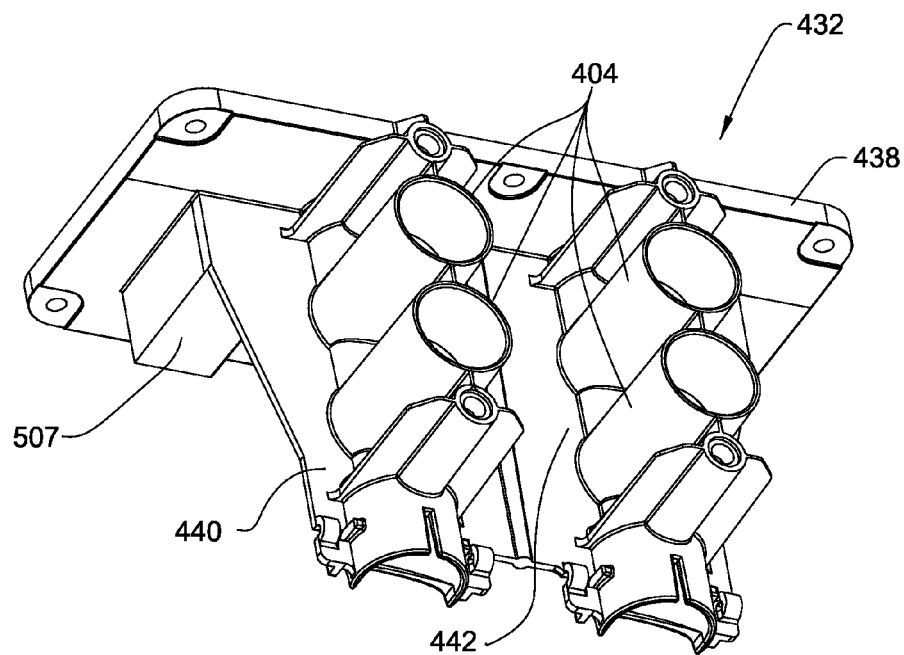
FIG. 20 is a top perspective view of a first housing portion of the vacuum manifold.

Referring specifically to FIG. 19, the second housing portion 434 defines first 456 and second 458 cavities. A first central hub 460 is generally disposed centrally in the first cavity 456. A first plurality of support ribs 462 integrally connects the first central hub 460 with a first inner ring 464. A first plurality of webs 466 extend radially outwardly from the first inner ring 464 to a first peripheral wall 468 to define a first plurality of pockets 470. A second central hub 472 is generally disposed centrally in the second cavity 458. A second plurality of ribs 474 integrally connects the second central hub 472 with a second inner ring 476. A second plurality of webs 478 extend radially outwardly from the second inner ring 476 to a second peripheral wall 480 to define a second plurality of pockets 482. The ribs 462, 474 and the webs 466, 478 are designed to provide structural rigidity to the first 456 and second 458 cavities. They are designed to withstand vacuum pressures exceeding 26 inches of Hg. O-rings 488 (see FIG. 18) are positioned in grooves 490, 492 surrounding the peripheral walls 468, 480. These o-rings 488 seal the first housing portion 432 to the second housing portion 434.

Figure 23A:
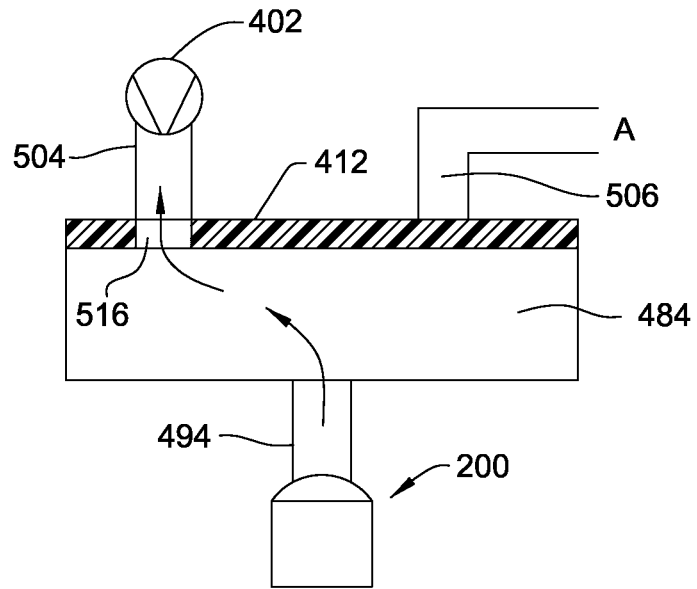
FIG. 23A is a schematic illustration of a first regulating chamber with a first valve member.
Figure 23B:
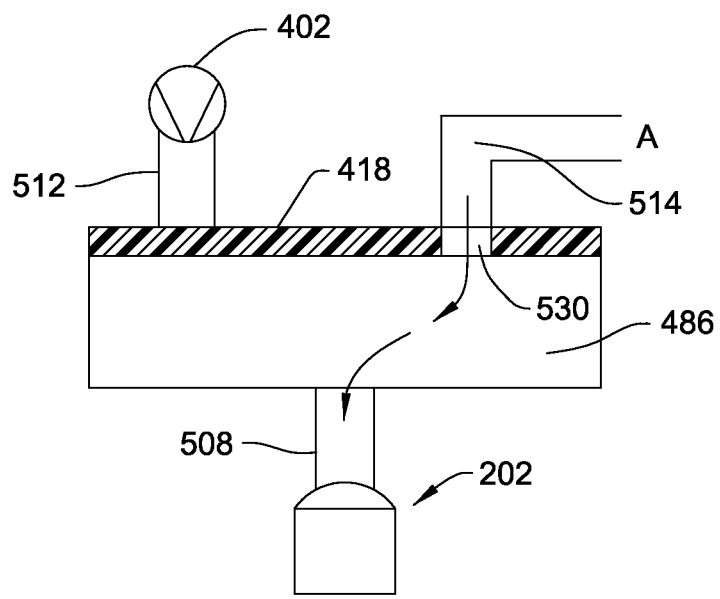
FIG. 23B is a schematic illustration of a second regulating chamber with a second valve member.
Figure 24:
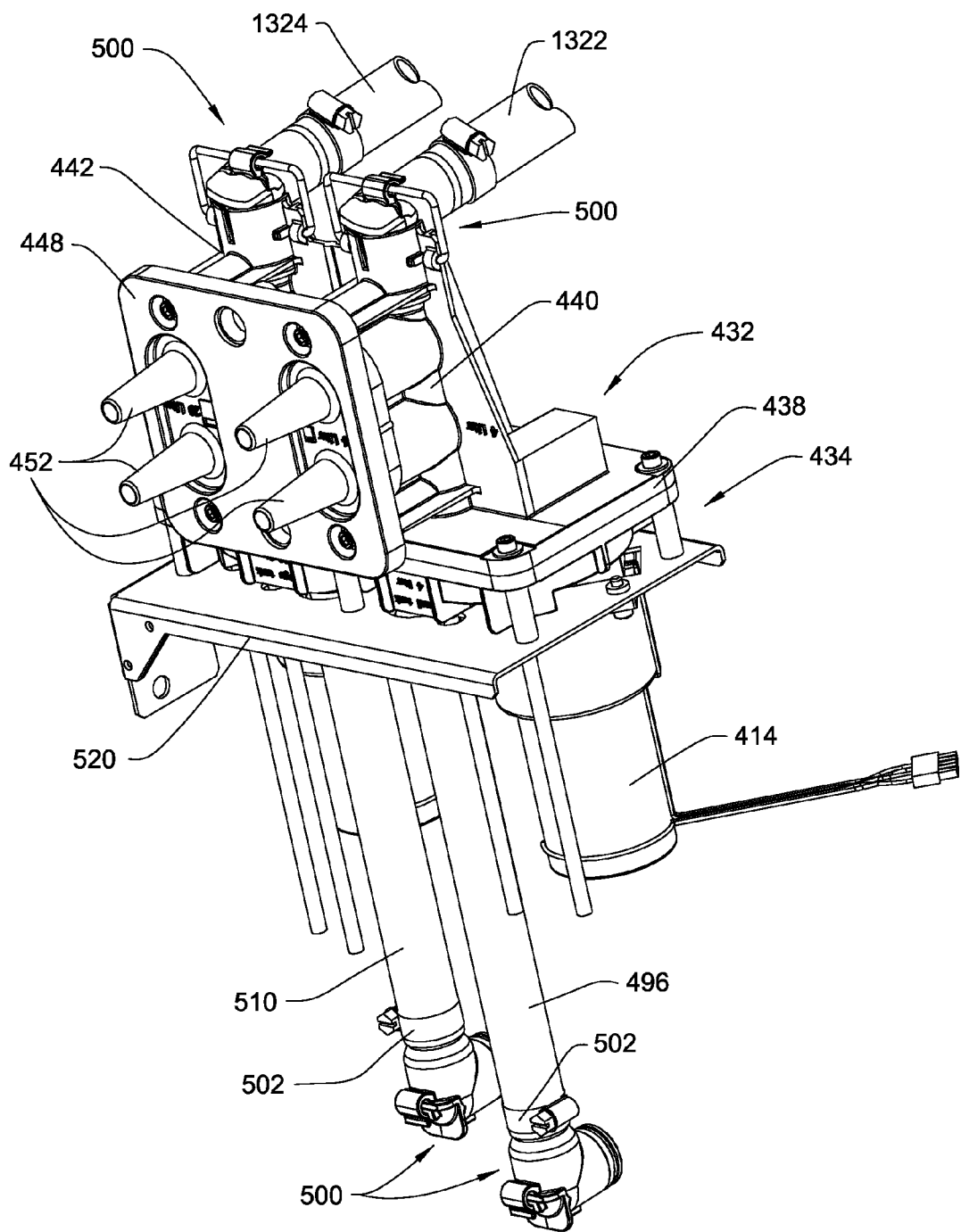
FIG. 24 is a front perspective view of the vacuum manifold.
Figure 25:
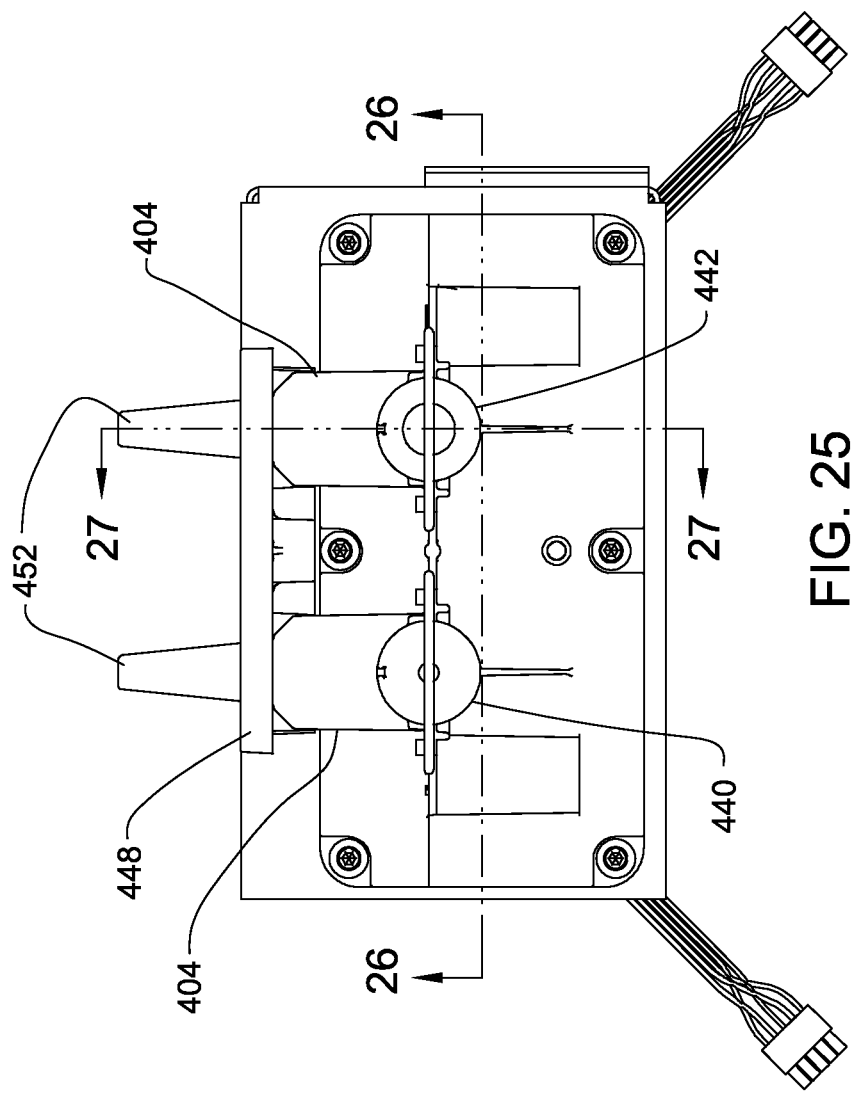
FIG. 25 is a top view of the vacuum manifold.

The first 456 and second 458 cavities form first 484 and second 486 regulating chambers when the first housing portion 432 is connected to the second housing portion 434. The regulating chambers 484, 486 are schematically represented in FIGS. 23A and 23B. In FIG. 23A, the first regulating chamber 484 includes a first inlet 494 in fluid communication with the upper waste container 200 and a first passage 506 open to atmospheric pressure A. The first regulating chamber 484 also includes a first outlet 504 in fluid communication with the vacuum pump 402. Referring back to FIG. 18, the first inlet 494 is preferably in the form of a barbed nozzle 494 for receiving one end of a vacuum line 496. The vacuum line 496 is sealed about the barbed nozzle 494 by a hose clamp 498. The other end of the vacuum line is connected to an elbow joint 500 by another hose clamp 502. The elbow joint 500 is adapted to connect to the upper cap 222 of the upper waste container 200, as described further below. The first outlet 504 is further defined as the entrance to the first main passage 444 (see FIG. 21) defined through the first tower section 440. The first passage 506 is formed in a first block 507 (see FIG. 21) attached the first tower section 440.

Referring to the schematic view of FIG. 23B, the second regulating chamber 486 includes a second inlet 508 in fluid communication with the lower waste container 202 and a second passage 514 open to atmospheric pressure A. The second regulating chamber 486 also includes a second outlet 512 in fluid communication with the vacuum pump 402. Referring back to FIG. 18, the second inlet 508 is preferably in the form of a barbed nozzle 508 for receiving one end of a second vacuum line 510. The second vacuum line 510 is sealed about the barbed nozzle 508 by a hose clamp 498. The other end of the second vacuum line 510 is connected to an elbow joint 500 by another hose clamp 498. The elbow joint 500 is adapted to connect to the lower cap 228 of the lower waste container 202, as described further below. The second outlet 512 is further defined as the entrance to the second main passage 446 (see FIG. 21) through the second tower section 442. The second passage 514 is formed in a second block 515 (see FIG. 21) attached to the second tower section 442.

Figure 26:
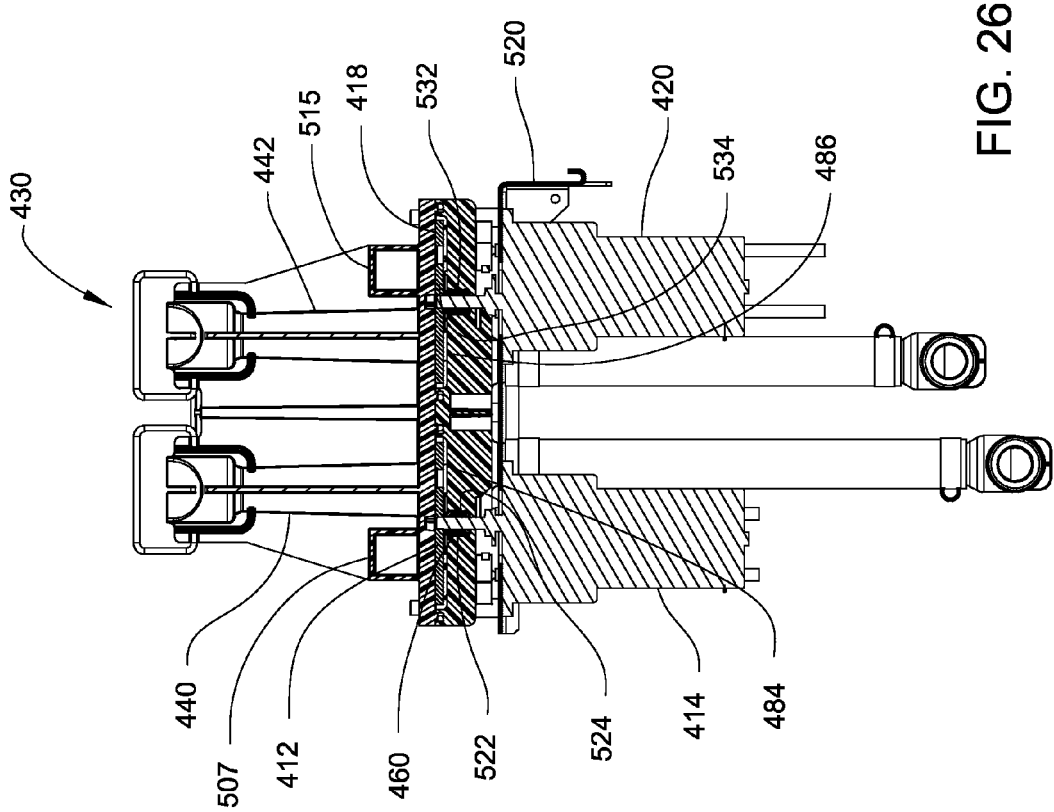
FIG. 26 is a cross-sectional view of the vacuum manifold illustrating the first and second valve members.
Figure 27:
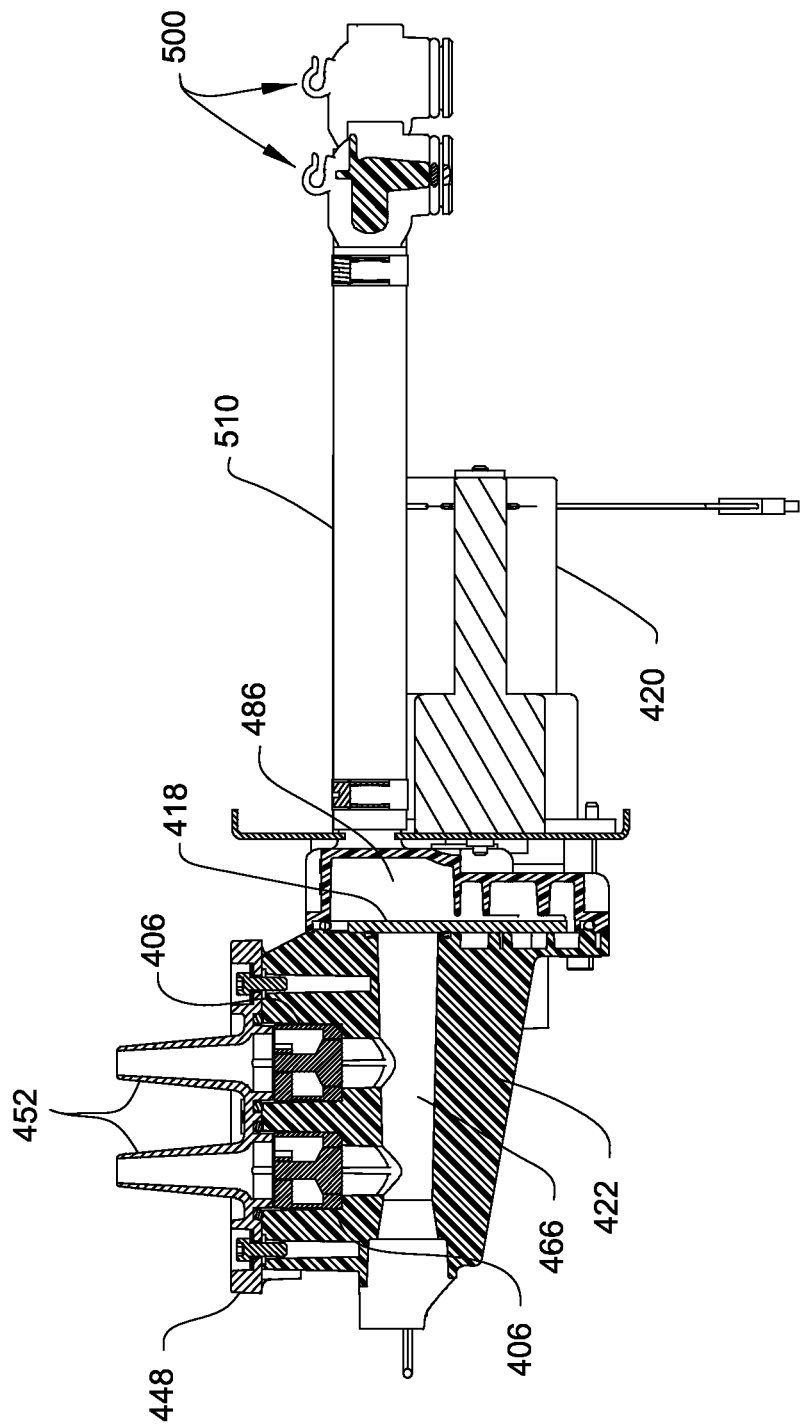
FIG. 27 is a cross-sectional view of the vacuum manifold illustrating a second main passage.

Referring to FIGS. 18, 23A, and 26, the first valve member 412 is disposed in the first regulating chamber 484. The first valve member 412 has a disk shape. Preferably, the first actuator 414 is a first position sensing motor 414 adapted to rotate the first valve member 412 between a plurality of rotational positions. The first valve member 412 defines a first source opening 516 for providing variable fluid communication between the first inlet 494 and the first outlet 504 and a first vent opening 518 for providing variable fluid communication between the first inlet 494 and the first passage 506. Accordingly, the first position sensing motor 414 rotates the first valve member 412 to adjust the vacuum level in the upper waste container 200 by regulating the amount of fluid flowing through the first valve member 412. The first valve member 412 is spaced from a top of the webs 466 such that fluid can pass beneath the first valve member 412 from the first inlet 494 to the first outlet 504 or to the first passage 506 when the first source opening 516 or the first vent opening 518 are properly aligned.

Referring specifically to FIG. 26, the first position sensing motor 414 is mounted to a bracket 520 and includes a first drive shaft 522 that protrudes through the bracket 520 and the first central hub 460 to engage the first valve member 412 at its center. A bushing 524 is disposed in a counterbore in the first central hub 460 and surrounds the first drive shaft 522. An o-ring seals the first drive shaft 522 in the first central hub 460. The bracket 520 attaches the vacuum manifold 430 to the vertical chassis 214 of the cart 204.

Referring to FIGS. 18, 23B, and 26, the second valve member 418 is disposed in the second regulating chamber 486. The second valve member 418 has a disk shape and is rotatably coupled to the second actuator 420. Preferably, the second actuator 420 is a second position sensing motor 420 adapted to rotate the second valve member 418 between a plurality of rotational positions. The second valve member 418 defines a second source opening 528 for providing variable fluid communication between the second inlet 508 and the second outlet 512 and a second vent opening 530 for providing variable fluid communication between the second inlet 508 and the second passage 514. The second valve member 418 is spaced from a top of the webs 478 such that fluid can pass beneath the second valve member 418 from the second inlet 508 to the second outlet 512 or to the second passage 514 when the second source opening 528 or the second vent opening 530 are properly aligned.

Referring specifically to FIG. 26, the second position sensing motor 420 is mounted to the bracket 520 and includes a second drive shaft 532 that protrudes through the bracket 520 and the second central hub 472 to engage the second valve member 418 at its center. A bushing 534 is disposed in a counterbore in the second central hub 472 and surrounds the second drive shaft 532. An o-ring seals the second drive shaft 532 in the second central hub 472.

Referring specifically to FIG. 21, first 538 and second 540 grooves are defined about the first outlet 504 and the second outlet 512. Additionally, third 542 and fourth 544 grooves are defined about the first passage 506 and the second passage 514. Referring back to FIG. 18, first 546 and second 548 face seals are seated in the first 538 and second 540 grooves and third 550 and fourth 552 face seals are seated in the third 542 and fourth 544 grooves. These face seals 546, 548, 550, 552 seal between the first 412 and second 418 regulator disks and the first housing portion 432 to prevent the undesired movement of fluid.

Figure 28B:
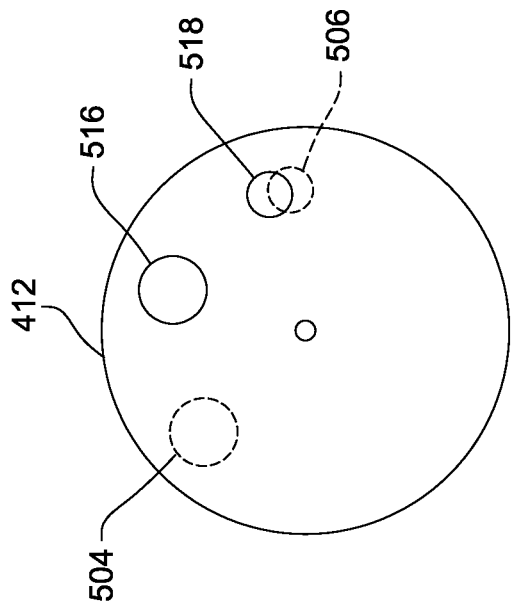
FIG. 28B is an illustration of the first valve member moved to a second position in which fluid communication is closed between the vacuum source and the upper waste container and fluid communication is opened between the upper waste container and atmospheric pressure.
Figure 28A:
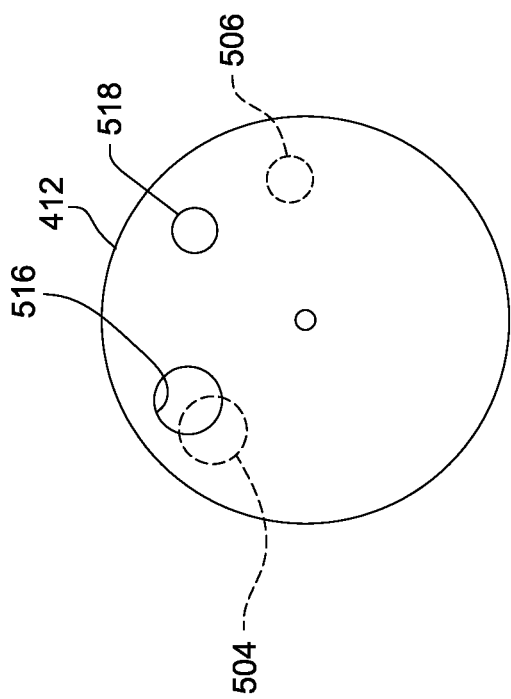
FIG. 28A is an illustration of the first valve member in a first position in which fluid communication is open between a vacuum source and the upper waste container.

Referring to FIG. 28A, the first valve member 412 is shown in a position in which the first source opening 516 partially overlaps with the first outlet 504 to allow fluid communication between the first inlet 494 and the first outlet 504. This opens fluid communication between the upper waste container 200 and the vacuum pump 402. The amount of overlap can be varied to increase or decrease the vacuum level in the upper waste container 200. By fully aligning the first source opening 516 with the first outlet 504, the upper waste container 200 is exposed to the full vacuum available from the vacuum pump 402. By completely misaligning the first source opening 516 relative to the first outlet 504, fluid communication is closed between the vacuum pump 402 and the upper waste container 200. In the position shown in FIG. 27A, the first vent opening 518 is not aligned whatsoever with the first passage 506 such that there is no fluid communication between the upper waste container 200 and atmospheric pressure A.

In FIG. 28B, the first valve member 412 is shown moved to a position in which the first source opening 516 is not aligned whatsoever with the first outlet 504. Thus, fluid communication is closed between the vacuum pump 402 and the upper waste container 200. However, in this position, the first vent opening 518 overlaps with the first passage 506 such that the upper waste container 200 is exposed to atmospheric pressure A to drive the vacuum level in the upper waste container 200 closer to atmospheric pressure A from its current pressure. The principles discussed here apply equally to the second valve member 418, but only the first valve member 412 is discussed for convenience. The regulator disks 412, 418 are shown formed of plastic materials, but they may also be formed of metallic materials such as stainless steel and the like.

Referring back to FIG. 17, the main controller 342 controls the vacuum controllers 411, 413, which control movement of the first 412 and second 418 regulator disks as previously discussed. Each of the position sensing motors 414, 420 includes an integrated position sensor 416, 422 that senses movement of the drive shafts 522, 532, which corresponds to movement of the regulator disks 412, 418. In other words, as the regulator disks 412, 418 are rotated, the position signals generated by the position sensors 416, 422 vary. The position signals are communicated to the vacuum controllers 411, 413 to determine a current position of the regulator disks 412, 418. This feedback is utilized by the vacuum controllers 411, 413, along with the pressure signals associated with the waste containers 200, 202, to determine how to adjust the regulator disks 412, 418 to achieve the desired vacuum levels in the waste containers 200, 202.

Referring back to FIGS. 18 and 24, first 554 and second 556 pairs of sensor tubes are attached to nipples 558 disposed on the second housing portion 434 of the vacuum manifold 430. One of the first pair 554 and one of the second pair 556 of the sensor tubes extend from the second housing portion 434 to the pressure sensors 424, 426. These sensor tubes 554, 556 essentially carry the existing vacuum levels in the waste containers 200, 202 back to the pressure sensors 424, 426.

Figure 29:
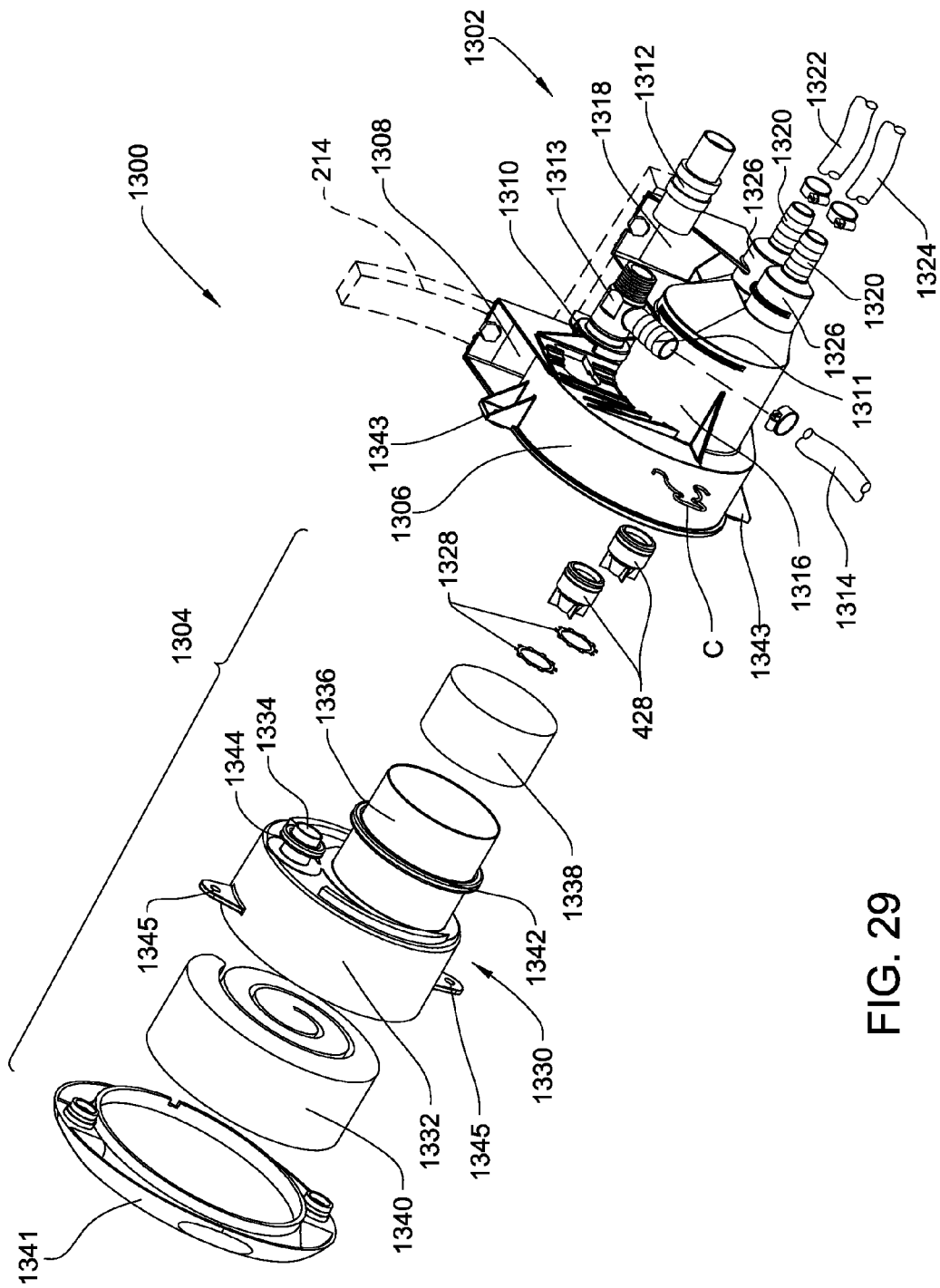
FIG. 29 is a exploded perspective view of a filter unit for the vacuum circuit.
Figure 31:
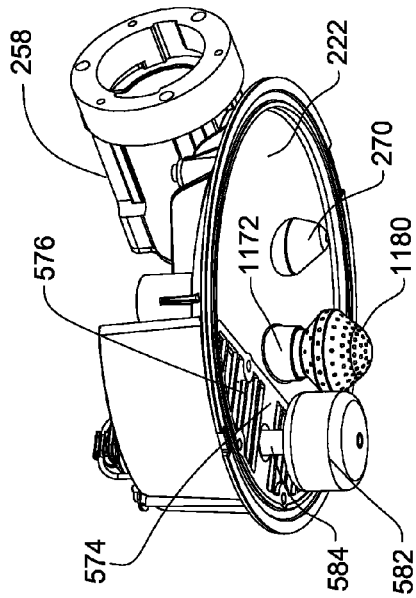
FIG. 31 is a bottom perspective view of the filter assembly disposed in the upper cap.
Figure 30:
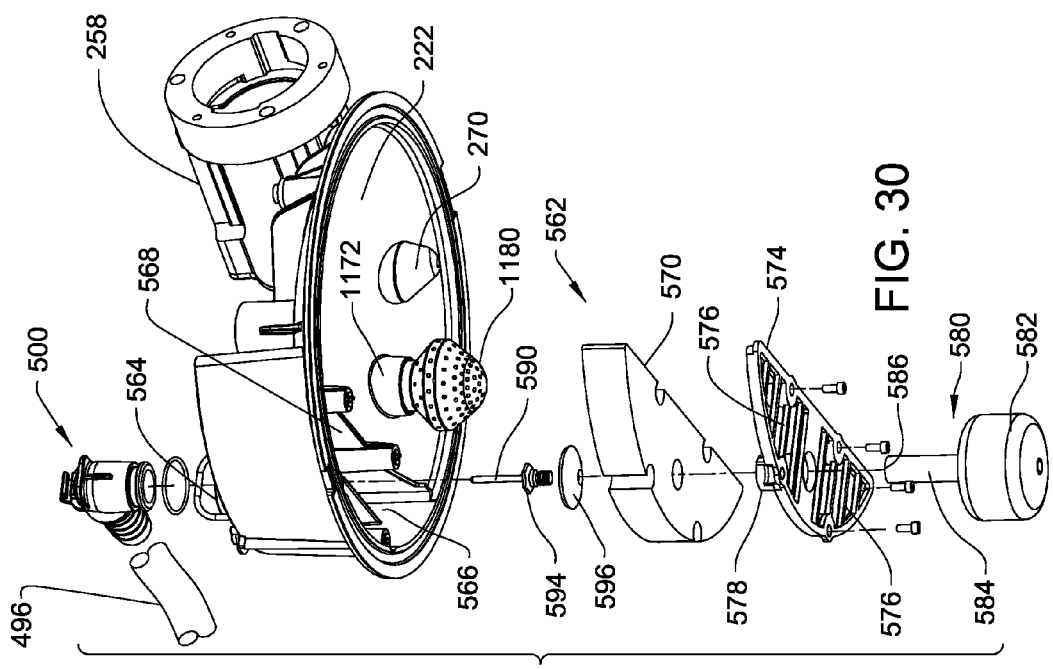
FIG. 30 is an exploded perspective view of a filter assembly with float positioned in the upper cap of the upper waste container.
Figure 32:
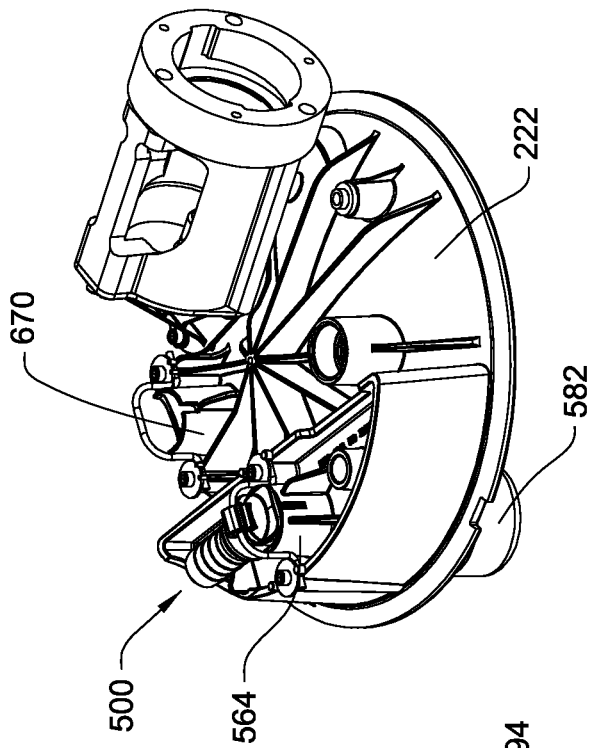
FIG. 32 is a top perspective view of the upper cap.

Referring to FIGS. 29 and 30, a filter unit 1300 filters the fluid drawn into the vacuum circuit 400 by the vacuum pump 402. The filter unit 1300 includes a filter housing 1302 for receiving a filter cartridge 1304. The filter housing 1302 may be formed of plastic or metallic materials. The filter housing 1302 includes a first hollow base section 1306. A mounting bracket 1308 is integrally formed with the first hollow base section 1306 to mount the first hollow base section 1306 to the vertical chassis 214 of the cart 204. An outlet 1310 is defined in the first hollow base section 1306. A tee connector 1313 is disposed in the outlet and secured there by a retaining clip C. A relief valve 1312 connects to one end of the tee connector 1313 and a barbed nozzle 1311 connects to the other end of the tee connector 1313. The barbed nozzle 1311 connects to a vacuum line 1314 extending to the vacuum pump 402.

A first hollow body section 1316 extends forwardly from the first hollow base section 1306. A second mounting bracket 1318 is integrally formed with the first hollow body section 1316 to mount the first hollow body section 1316 to the vertical chassis 214. A pair of inlets 1320, in the form of barbed nozzles 1320, extends from the first hollow body section 1316. One of the inlets 1320 connects to a vacuum line 1322 that extends from the connector 500 mounted to the first tower section 440 (see FIG. 24). The other inlet 1320 connects to a vacuum line 1324 that extends from the connector 500 mounted to the second tower section 442 (see FIG. 24).

Two hollow neck sections 1326 extend forwardly from the first hollow body section 1316. The two check valves 428 are inserted inside the hollow neck sections 1326 just downstream of the inlets 1320. Retainers 1328 hold the check valves 428 inside the hollow neck sections 1326. The check valves 428 may be check valve cartridges commercially available from Neoperl, Inc. of Waterbury, Conn. An example of such a check valve is shown in U.S. Pat. No. 6,837,267 to Weis et al., hereby incorporated by reference.

The first hollow base section 1306 and first hollow body section 1316 are integrally formed to define a chamber for receiving the filter cartridge 1304. The filter cartridge 1304 includes a cartridge housing 1330 with a second hollow base section 1332 having a hollow boss 1334. A second hollow body section 1336 extends forwardly from the second hollow body section 1316. The second hollow body section 1336 may be integrally formed with the second hollow base section 1306 or may be a separate component joined to the second hollow base section 1306. A HEPA filter element 1338 is shaped to fit snugly inside the second hollow body section 1336. An activated carbon filter element 1340 is shaped to fit snugly inside the second hollow base section 1332. In one embodiment, the activated carbon filter element 1340 has a porosity of 10 to 30 pores per inch, most preferably 20 pores per inch, and is impregnated with activated carbon. The activated carbon in the activated carbon filter element 1340 helps to remove foul odors associated with the fluid drawn into the vacuum circuit 400. The activated carbon filter element 1340 is preferably provided in a spiral configuration. This spiral configuration provides a compact package that allows longer fluid contact time with the activated carbon since the fluid follows the spiral. The longer contact time, along with the depth of the carbon, allows the activated carbon to remove more foul odors and last longer.

A plastic cover 1341 mounts to the first 1306 and second 1332 hollow base sections to secure the activated carbon filter element 1340 in the second hollow base section 1332 and to secure the filter cartridge 1304 in the filter housing 1302. More specifically, the first 1306 and second 1332 hollow base sections include first 1343 and second 1345 pairs of ears for receiving fasteners (not shown) to mount the cover 1341 to the hollow base sections 1306, 1332. In other embodiments, the cover 1341 may only mount to the second hollow base section 1332 to be an integrated and disposable part of the disposable filter cartridge 1304. In this case, a filter door w/foam backing (not shown) is mounted to the rear cover R and presses against the cover 1341 to hold the filter cartridge 1304 inside the filter housing 1302. In other words, in this embodiment, there are no fasteners holding the filter cartridge 1304 in place in the filter housing 1302.

An o-ring 1342 surrounds the second hollow body section 1336 to seal the second hollow body section 1336 inside the hollow body section 1316 of the filter housing 1302. The o-ring 1342 prevents fluid that enters the filter housing 1302 through the inlets 1320 from passing around the second hollow body section 1336 and instead forces the fluid to enter the HEPA filter element 1338. Likewise, the boss 1334 has an o-ring 1344 that seals the hollow boss 1334 inside the outlet 1310 of the filter housing 1302 to prevent fluid from passing around the hollow boss 1334 on its way out through the outlet 1310. This forces the fluid to pass into the inlets 1320, through the HEPA filter element 1338 and the activated carbon filter element 1340 before exiting through the outlet 1310.

During use, the relief valve 1312 prevents the vacuum pump 402 from overheating. Without the relief valve 1312, the vacuum pump 402 may inadvertently overheat during use when the vacuum pump 402 is operating, but suction is not active in either waste container 200, 202 for prolonged periods of time. The relief valve 1312 is set to allow cool air flow into the vacuum pump 402 when the maximum vacuum level of the vacuum pump 402 has been reached. This cools the vacuum pump 402 and prevents an unwanted shut down. As shown in FIG. 1, the cover 1341 may be externally exposed through the rear cover R of the waste collection unit 102. Alternatively, the cover 1341 may be concealed behind the filter door (not shown). When the user desires to change the filter cartridge 1304, such as when the filter elements 1338, 1340 become clogged, the user simply removes the fasteners holding the cover 1341 to the hollow base sections 1306, 1332 and removes the filter cartridge 1304, or, alternatively, the user removes the filter door to access the filter cartridge 1304, which then easily pops out by grasping a handle (not shown) connected to the cover 1341. The user grasps the filter cartridge 1304 and pulls it from the filter housing 1302 and a new filter cartridge 1304 is installed in its place.

IV. Mist Trap and Float

Referring to FIGS. 30 through 33, each of the caps 222, 228 are outfitted with a filter and float assembly 562 for preventing water droplets and waste material from entering the vacuum circuit 400. Otherwise, these materials may enter the vacuum lines 496, 510, and potentially foul the downstream vacuum pump 402. A vacuum port 564 (see FIG. 33) is defined in each of the caps 222, 228. The elbow joints 500 that extend from the vacuum lines 496, 510 of the vacuum manifold 430 are connected to these vacuum ports 564 to provide the vacuum inside the waste containers 200, 202. Only the vacuum port 564 of the upper cap 222 is shown for convenience. The vacuum port 564 of the upper cap 222 opens into a filter compartment 566. The filter compartment 566 is defined by a partitioning wall 568 extending from an underside of the upper cap 222, best shown in FIG. 30. The filter and float assembly 562 is disposed in the filter compartment 566.

The filter and float assembly 562 includes a mist trap 570 disposed in the filter compartment 566 such that any fluid, e.g., air, passing into the vacuum port 564 from within the upper canister 218 must first pass through the mist trap 570. The mist trap 570 is preferably a filter element having a porous structure formed of activated carbon material. The porosity of the mist trap 570 is from 5 to 20 pores per inch, most preferably 10 pores per inch. The porous structure works to absorb water droplets entrained in the fluid passing into the vacuum port 564 to prevent fouling of the vacuum pump 402. A retaining member retains the mist trap 570 within the filter compartment 566. The retaining member includes a vent plate 574 defining a plurality of elongated vents 576 to allow the fluid to pass into the mist trap 570. The vent plate 574 includes a sleeve 578 extending upwardly.

Figure 33:
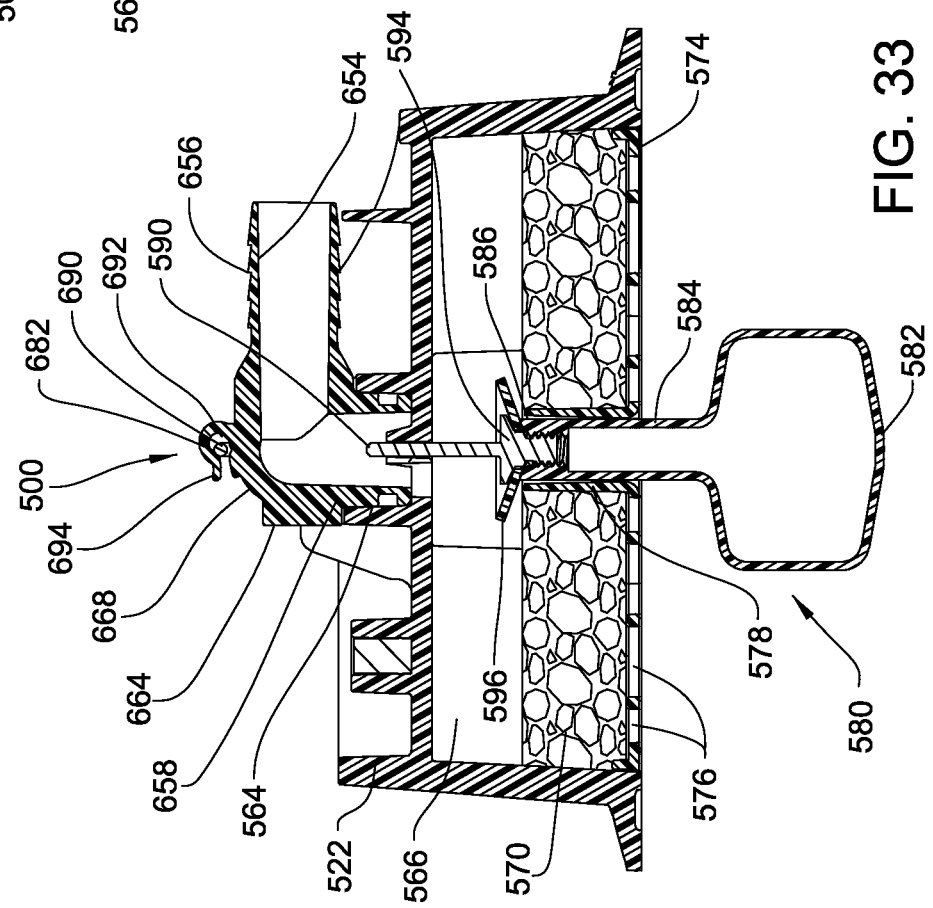
FIG. 33 is a cross-sectional view of the filter assembly.
Figure 34:
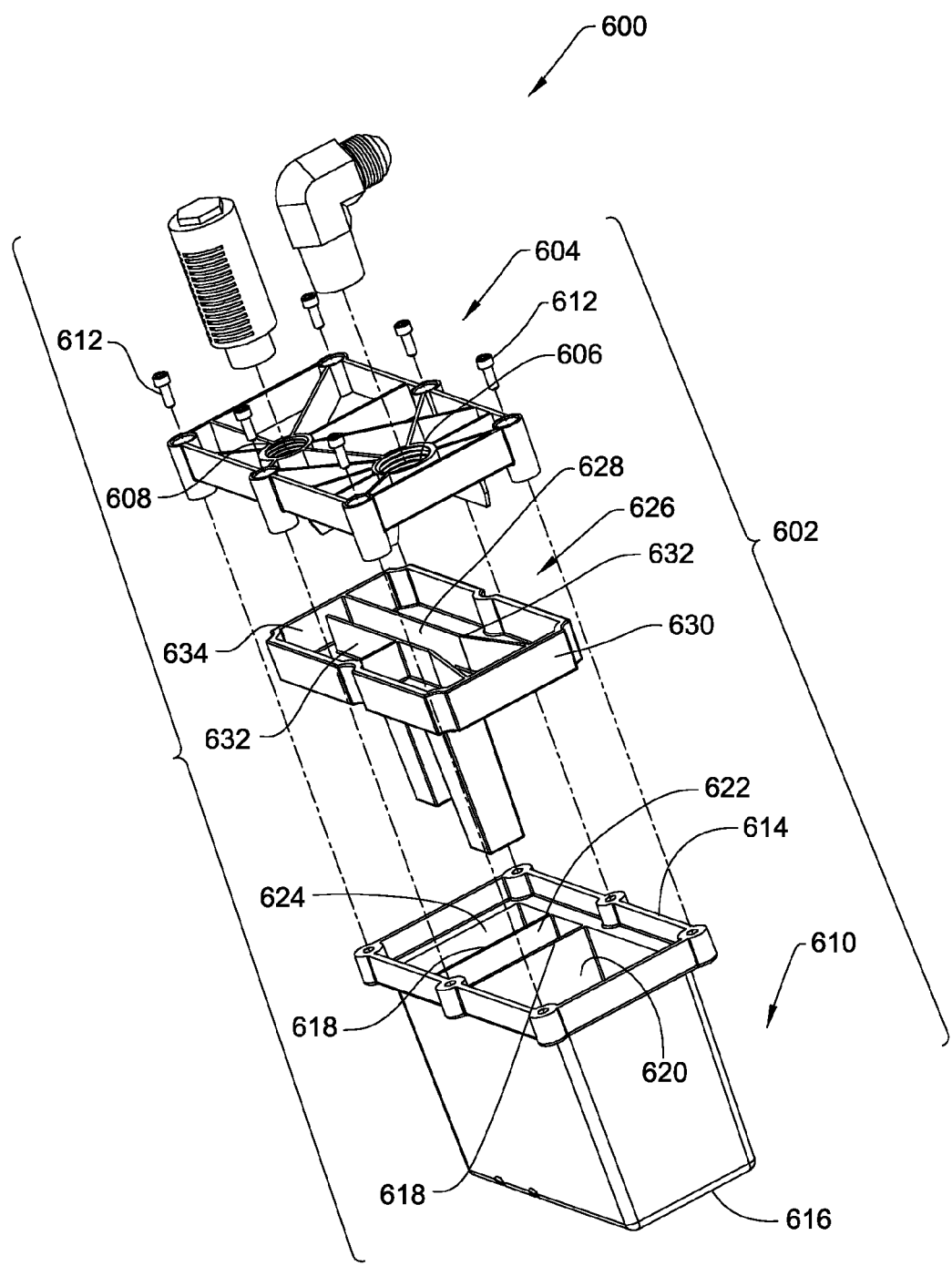
FIG. 34 is an exploded perspective view of a noise attenuator for use in the vacuum circuit.
Figure 35:
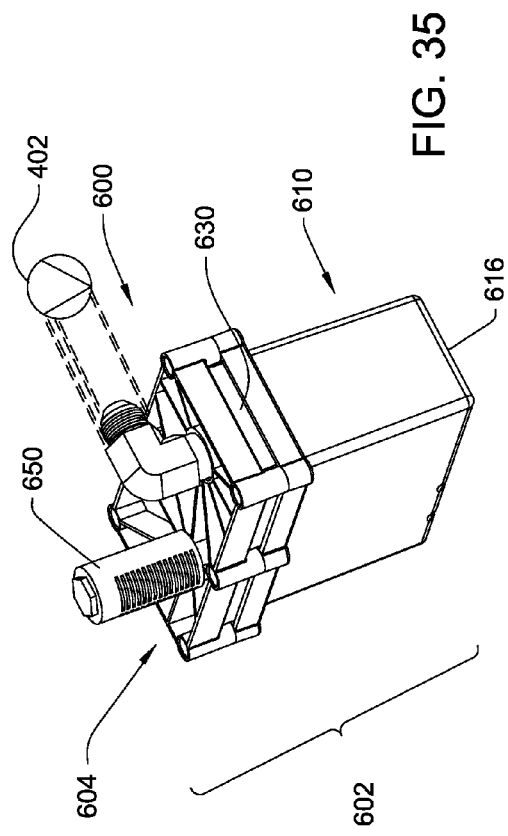
FIG. 35 is a top perspective view of the noise attenuator.

Referring specifically to FIG. 33, a float 580, formed of plastic or other lightweight materials, is slidably supported in the sleeve 578 of the vent plate. More specifically, the float 580 includes a balloon-like head 582 and a neck 584 extending upwardly from the head 582 to a tip 586. The neck 584 slides in the sleeve 578. Threads are defined in the tip 586 of the neck 584. A stem 590 having threads at one end engages the threads of the tip 586. The stem 590 includes a shoulder 594. The shoulder 594 traps a seal member 596 between the stem 590 and the tip 586. The stem 590 extends to a second end away from the neck 584 that is slidably supported in a bore defined within the upper cap 222 at a bottom of the vacuum port 564.

During use, should the level of the waste material in the upper canister 218 exceed a predetermined threshold, the waste material will lift the float 580 upwardly and drive the second end of the stem 590 further into the vacuum port 564. Eventually, the shoulder 594 will abut the upper cap 222 and prevent further upward movement of the float 580. At this point, the seal member 596 covers the vacuum port 564 and mechanically shuts off the suction draw from the vacuum pump 402. In other words, fluid will be prevented from entering the vacuum port 564 from the upper canister 218. As a result, additional waste material is not suction drawn into the upper waste container 200. The float 580 provides a back-up shut off valve to the vacuum pump 402 should the electronic shut-off fail.

V. Noise Attenuator

Referring to FIGS. 17 and 34 through 36, a noise attenuator 600 is used to reduce noise that results from operation of the vacuum pump 402 on the waste collection unit 102. It should be appreciated that a noise attenuator 600 such as the one shown in U.S. Pat. No. 6,935,459 to Austin et al., issued on Aug. 30, 2005, hereby incorporated by reference, may also be used on the exhaust of the vacuum pump 402 to reduce noise. The noise attenuator 600 shown in FIGS. 34 through 36 operates on the same basic principles as that of the noise attenuator disclosed in the '459 patent to Austin et al.

As previously discussed, the vacuum pump 402 is preferably of the rotary vane type. The vacuum pump 402 is capable of generating vacuum pressures of 0 to 26 inches of Hg. As understood by those skilled in the art, the vacuum pump 402 includes a shaft (not shown) that rotates a plurality of vanes (not shown). The rotation of the vanes produces loud sound waves at a first harmonic frequency $F_1$, a second harmonic frequency $F_2$, a third harmonic frequency $F_3$, etc. The sound waves emanate from the vacuum pump 402 and travel through the fluid. The ability to effectively eliminate the sound waves is hindered by the small space available to do so. The noise attenuator 600 is sufficiently compact to fit within the waste collection unit 102 and more effectively eliminates the sound waves traveling through the fluid than other types of devices currently in use.

The noise attenuator 600 includes a manifold 602, preferably formed of plastic, having an internally-ribbed member 604 defining an inlet 606 and an outlet 608. The manifold 602 also includes a lower box-shaped portion 610 connected to the ribbed member 604. A plurality of fasteners 612 secure the ribbed member 604 to the lower box-shaped portion 610. The box-shaped portion 610 has an open first end 614 and a closed second end 616. A plurality of partitions 618 divides the box-shaped portion 610 into first 624, second 622, and third 620 chambers that are open at the first end and closed at the second end. A cartridge 626 is captured between the ribbed member 604 and the box-shaped portion 610. The cartridge 626 defines a main duct 628 extending between the inlet 606 and the outlet 608.

Figure 36:
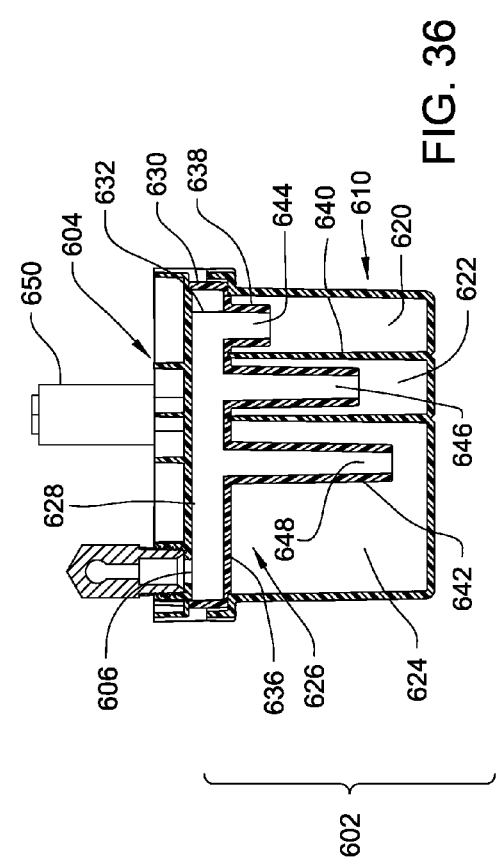
FIG. 36 is a cross-sectional view of the noise attenuator.

The main duct 628 accommodates the flow of fluid from the inlet 606, which is connected to the exhaust of the vacuum pump 402, to the outlet 608, which ultimately leads to the external environment. The cartridge 626 includes a peripheral wall 630 and a plurality of interior walls 632 such that the main duct 628 leads around a bend 634 between the inlet 606 and outlet 608. The walls 630, 632 also locate the main duct 628 such that it passes down a center of the cartridge 626. Referring specifically to FIG. 36, the cartridge 626 further includes a bottom 636 and the walls 630, 632 extend upwardly from the bottom 636. First 642, second 640, and third 638 necks extend downwardly from the bottom 636 into the first 624, second 622, and third 620 chambers. Each of the necks 642, 640, 638 has a successively smaller length. The necks define first 648, second 646, and third 644 passages from the main duct 628 into the first 624, second 622, and third 620 chambers.

As the fluid passes through the main duct 628, the sound waves traveling in the fluid are attenuated by the plurality of chambers 624, 622, 620. The first chamber 624 defines a volume $V_1$ for attenuating the sound waves generated at the first harmonic frequency $F_1$. The first neck 642 extends into the first chamber 624. More specifically, the first neck 642 includes a proximal end integral with the bottom 636 of the cartridge 626 and extends downwardly to a distal end. The distal end of the first neck 642 is suspended in the volume $V_1$ of the first chamber 624. That is, the distal end of the first neck 642 does not contact the box-shaped portion 610.

The first harmonic frequency $F_1$ denotes the frequency at which the acoustic field reaches its largest magnitude. Thus, a significant noise reduction is achieved by attenuating the sound waves at the first harmonic frequency $F_1$. The first harmonic frequency $F_1$ is defined by the following equation:

$$F_1 = R*N \qquad (1)$$

where $F_1$ is the first harmonic frequency, R is a number of rotations of the shaft per second, and N is a number of vanes. Preferably, R is 25 or greater and N is 4 or greater. More preferably, R is 29 and N is 4. The first harmonic frequency $F_1$ is also defined by the following equation:

$$F_1 = \frac{C}{2\Pi}\sqrt{\frac{A_1}{V_1 L_1}} \qquad (2)$$

where $F_1$ is the first harmonic frequency and is a constant with respect to the noise attenuator, C is a velocity of sound at 17° C., $A_1$ is a cross-sectional area of the first passage 648, $V_1$ is the volume of the first chamber 624, and $L_1$ is a length of the first passage 648. Thus, by fixing the dimensions of the first chamber 624 and the first passage 648, the noise attenuator 600 is tuned to attenuate sound waves at the first harmonic frequency $F_1$. In the preferred embodiment, the first harmonic frequency $F_1$ is 100 Hertz or greater. More preferably, the first harmonic frequency $F_1$ is 116 Hertz. The first chamber 624 and the first neck 642 can be tuned to attenuate sound waves at various frequencies. In alternative embodiments, another equation could be used to define the frequency of a Helmholtz resonator. This equation takes into account end effects of the 'passage'. It's referred to as "port end correction", and looks similar to the above-equation, but with an added compensation factor:

$$F_1 = \frac{C}{2\Pi}\sqrt{\frac{A_1}{V_1(L_1 + .732 D_1)}} \qquad (3)$$

Where $D_1$ is the diameter of the passage for a round cross-section. For purposes of simplicity, only use of the above-equation will be discussed throughout.

The second chamber 622 attenuates the sound waves at the second harmonic frequency $F_2$. The second chamber 622 defines a volume $V_2$ for attenuating the sound waves generated at the second harmonic frequency $F_2$. The second neck 640 extends into the second chamber 622. More specifically, the second neck 640 includes a proximal end integral with the bottom 636 of the cartridge 626 and extends to a distal end. The distal end of the second neck 640 is suspended in the volume $V_2$ of the second chamber 622. That is, the distal end of the second neck 640 does not contact the box-shaped portion 610.

The second harmonic frequency $F_2$ is double the first harmonic frequency $F_1$ and denotes the frequency at which the acoustic field reaches its next largest magnitude in comparison to the first harmonic frequency $F_1$. Thus, a greater noise reduction is achieved by attenuating the sound waves at the first harmonic frequency $F_1$ and the second harmonic frequency $F_2$ than by merely attenuating the sound waves at the first harmonic frequency $F_1$. The second harmonic frequency $F_2$ is defined by the following equation:

$$F_2 = \frac{C}{2\Pi}\sqrt{\frac{A_2}{V_2 L_2}} \qquad (4)$$

where $F_2$ is the second harmonic frequency and is a constant with respect to the noise attenuator, C is the velocity of sound at 17° C., $A_2$ is a cross-sectional area of the second passage 646, $V_2$ is the volume of the second chamber 622, and $L_2$ is a length of the second passage 646. Preferably, the second harmonic frequency $F_2$ is 200 Hertz or greater. More preferably, the second harmonic frequency $F_2$ is 232 Hertz. The second chamber 622 and second passage 646 can be tuned to attenuate sound waves at various frequencies.

The third chamber 620 attenuates the sound waves at the third harmonic frequency $F_3$. The third chamber 620 defines a volume $V_3$ for attenuating the sound waves generated at the third harmonic frequency $F_3$. The third neck 638 extends into the third chamber 620. More specifically, the third neck 638 includes a proximal end integral with the bottom 636 of the cartridge 626 and extends to a distal end. The distal end of the third neck 638 is suspended in the volume $V_3$ of the third chamber 620. That is, the distal end of the third neck 638 does not contact the box-shaped portion 610.

The third harmonic frequency $F_3$ is triple the first harmonic frequency $F_1$ and denotes the frequency at which the acoustic field reaches its next largest magnitude in comparison to the second harmonic frequency $F_2$. Thus, a greater noise reduction is achieved by attenuating the sound waves at the first harmonic frequency $F_1$, the second harmonic frequency $F_2$, and the third harmonic frequency $F_3$ than by merely attenuating the sound waves at the first harmonic frequency $F_1$ and the second harmonic frequency $F_2$. The third harmonic frequency $F_3$ is defined by the following equation:

$$F_3 = \frac{C}{2\Pi}\sqrt{\frac{A_3}{V_3 L_3}} \quad (5)$$

where $F_3$ is the third harmonic frequency and is a constant with respect to the noise attenuator, C is the velocity of sound at 17° C., $A_3$ is a cross-sectional area of the third passage 644, $V_3$ is the volume of the third chamber 620, and $L_3$ is a length of the third passage 644. Preferably, the third harmonic frequency $F_3$ is 300 Hertz or greater. More preferably, the third harmonic frequency $F_3$ is 348 Hertz. The third chamber 620 and third passage 644 can be tuned to attenuate sound waves at various frequencies. Additional chambers or fewer chambers could be formed to attenuate sound waves at frequencies other than the first harmonic frequency $F_1$, the second harmonic frequency $F_2$, and the third harmonic frequency $F_3$. However, the most significant noise reduction is experienced by attenuating sound waves at all three harmonic frequencies $F_1$, $F_2$, $F_3$.

A muffler 650 is connected to the outlet 608 and is in fluid communication with the main duct 628 for dampening some of the sound waves not attenuated by the chambers 620, 622, 624. Preferably, the muffler 650 extends from an opposite side of the manifold 602 as the remaining sound waves are forced around the bend 634 of the main duct 628 before entering the outlet 608 and the muffler 650. The fluid flow exits the noise attenuator 600 through the muffler 650. Preferably, the muffler 650 is of the type commercially available from Gast Manufacturing, Incorporated. However, the muffler 650 can be any type of muffler capable of fitting with the noise attenuator 600 on the cart 204.

VI. Elbow Connectors

Figure 37:
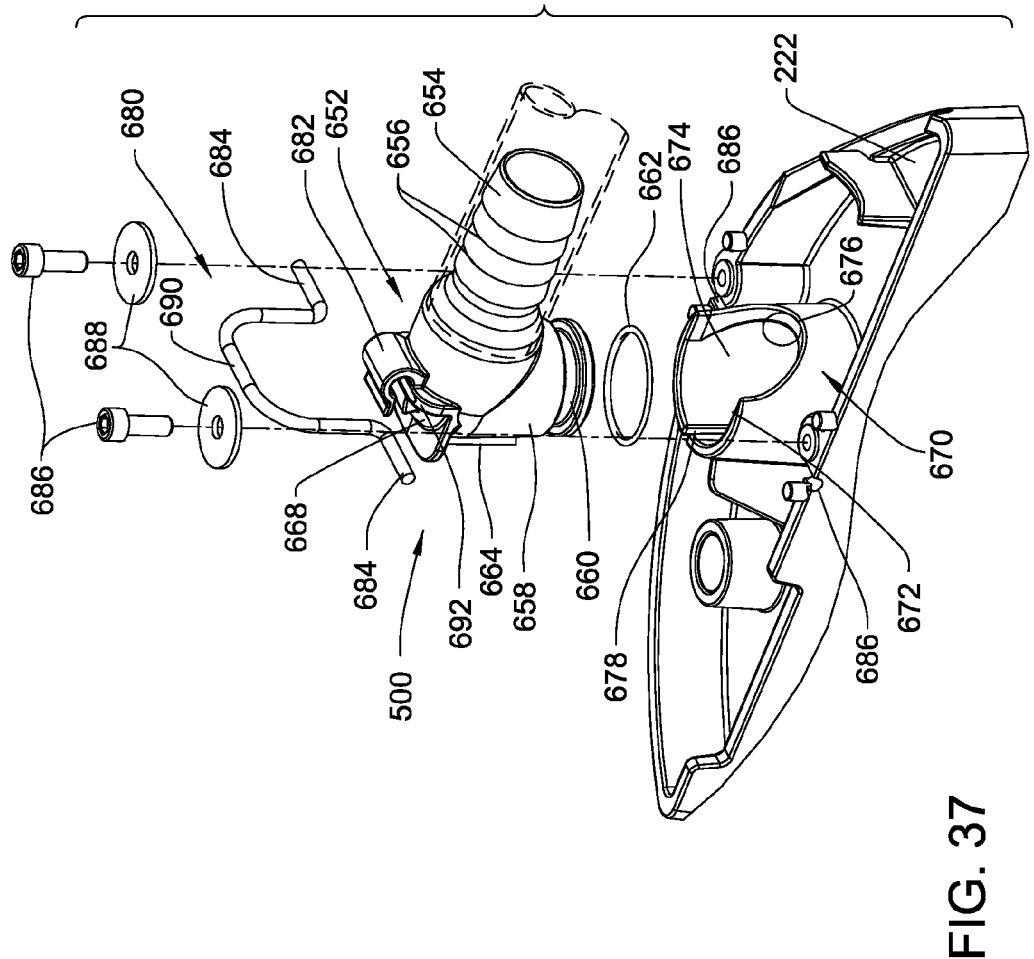
FIG. 37 is an exploded perspective view illustrating an elbow connector used in connecting vacuum and water lines of the waste collection unit.

Referring to FIG. 37, the elbow connector 500 is described in greater detail. The elbow connector 500 is representative of several elbow connectors 500 used in the system 100 to connect vacuum lines (e.g., vacuum tubes, hoses, conduits, etc.) to the components in the vacuum circuit 400 and to connect water lines (e.g., water tubes, hoses, conduits, etc.) to components in a cleaning system, described further below. Thus, the elbow connectors 500 can be designed and rated to accommodate vacuum pressure or water pressure. One of the primary advantages of the elbow connectors 500 is the ease in which they can be attached and/or removed during assembly and/or servicing.

The elbow connector 500 is preferably formed of a plastic material capable of withstanding high vacuum pressures or water pressures. The elbow connector 500 includes a generally L-shaped body 652 with a first arm 654 having a plurality of annular ridges 656 defined on its outer surface. The L-shaped body 652 also includes a second arm 658 with a groove 660 defined in its outer surface. The ridges 656 are configured to grip a vacuum or water line that connects to the first arm 654. An o-ring 662 is seated in the groove 660. A rib 664 (see also FIG. 33) is integrally formed on the outer surface of the second arm 658 and extends from near a bend 668 of the L-shaped body 652 down the second arm 658.

A receptacle 670 receives the elbow connector 500 to complete the connection to the component with which the elbow connector 500 is to be attached. In FIG. 37, the receptacle 670 is defined in the upper cap 222 of the upper waste container 200. The receptacle 670 includes an outer wall 672 that defines a pocket 674 for receiving the elbow connector 500. The outer wall 672 includes an arcuate cut-out portion 676 on which the first arm 654 rests when the elbow connector 500 is seated in the receptacle 670. The outer wall 672 also defines an elongated slot 678, opposite the arcuate cut-out portion 676, which extends from a top of the outer wall 672 downwardly along the outer wall 672. The rib 664 formed on the outer surface of the second arm 658 of the L-shaped body 652 is configured to snugly mate with the elongated slot 678 when the elbow connector 500 is seated in the receptacle 670. This prevents unwanted rotation of the elbow connector 500 in the receptacle 670.

A retainer 680 and associated detent clip 682 prevents the elbow connector 500 from popping out of the receptacle 670 once in place. The retainer 680 is preferably formed of round metal stock into a generally U-shape with opposing extensions 684 at each end. Semi-circular grooves 686 are formed in the upper cap 222 for pivotally supporting the extensions 684 such that the retainer 680 can be rotated between an unlocked position in which the retainer 680 lays flat on the upper cap 222 and a locked position (see FIG. 33) in which the retainer 680 engages the elbow connector 500 to lock the elbow connector 500 in the receptacle 670. A pair of fasteners 686 and washers 688 holds the extensions 684 in the semi-circular grooves 686.

When moving to the locked position, as shown in FIG. 33, an upper bar 690 of the retainer 680 engages the detent clip 682 and snap-fits into a detent pocket 692. The detent clip 682 is integrally formed on the first arm 654 and includes a lip 694 that flexes upwardly as the upper bar 690 is pressed into the detent pocket 692. Once the upper bar 690 is secure in the detent pocket 692, the lip 694 moves back to its initial position to hold the retainer 680 in the locked position. To release the retainer 680, the upper bar 690 is simply removed from the detent pocket 692 by pressing against the lip 694 and again flexing the lip 694 upwardly to allow the retainer 680 to move back to the unlocked position. This quick-lock action of moving between the locked and unlocked positions, and vice versa, in a single rotational or flipping motion, provides for easy assembly and servicing of the waste collection unit 102.

VII. Volumetric Liquid Measuring

Figure 38:
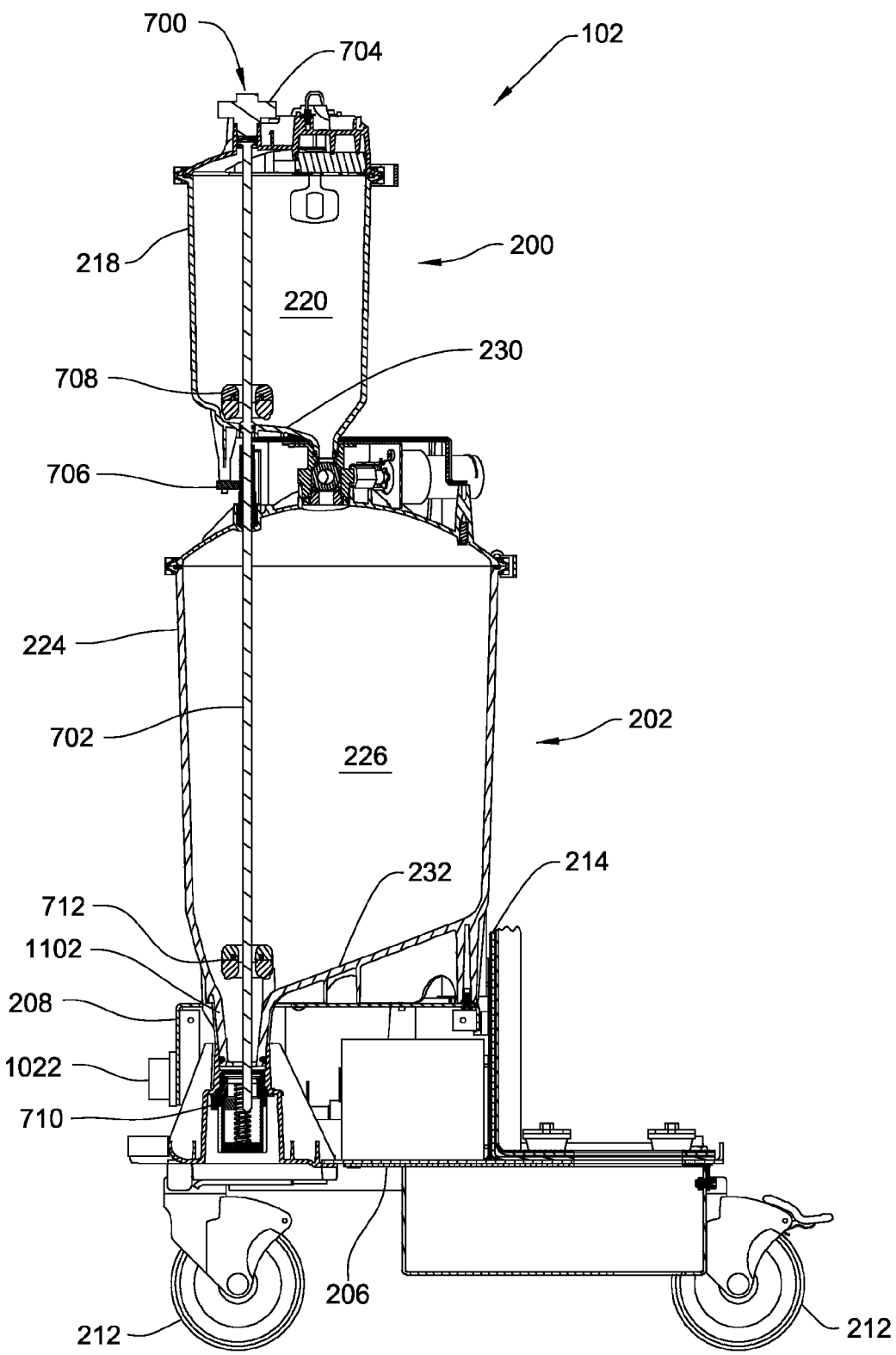
FIG. 38 is a cross sectional diagram of the waste collection unit showing components of the level sensing system.

Referring to FIG. 38, the mobile waste collection unit 102 includes a liquid measuring system 700. The fluid measuring system 700 provides an estimation of the volume of liquid (e.g., the waste materials) collected by the unit 102. Specifically, in the preferred embodiment, the liquid measuring system 700 provides separate estimations of the liquid in the upper canister 218 of the upper waste container 200 and the liquid in the lower canister 224 of the lower waste container 202.

The liquid measuring system 700 includes a sensor rod 702. In the preferred embodiment, the sensor rod 702 is a single sensor rod 702 which runs through both the upper waste chamber 220 of the upper canister 218 and the lower waste chamber 226 of the lower canister 224. Utilizing a single sensor rod 702 is done for efficiency, weight, and cost reasons. However, those skilled in the art realize that multiple sensor rods 702 could be implemented, e.g., one sensor rod 702 for each canister 218, 224.

In the preferred embodiment, the sensor rod 702 is formed of a magnetostrictive (or ferromagnetic) material. Those skilled in the art realize that magnetostrictive materials change in shape when subjected to a magnetic field. A transceiver 704 is electrically connected to the sensor rod 702 and preferably disposed above said upper canister 218. The transceiver 704 generates an interrogation pulse that propagates along the sensor rod 702. This interrogation pulse is thus directed downward and creates an electromagnetic field as it travels along the sensor rod 702. Thus, the sensor rod 702 acts as a waveguide for the interrogation pulse.

A plurality of reflecting elements are disposed adjacent to and along the sensor rod 702. The reflecting elements cause return pulses to be reflected back toward the transceiver 704 in response to receiving the interrogation pulse. In the preferred embodiment, each reflecting element includes at least one magnet. The magnets create magnetic fields in the magnetostrictive sensor rod 702 which result in the return pulses. The liquid measuring system 700 of the preferred embodiment includes four reflecting elements. An upper reference element 706 and an upper float element 708 are associated with the upper waste container 200. A lower reference element 710 and a lower float element 712 are associated with the lower waste container 202. The upper float element 708 is disposed within the upper waste container 200 and the lower float element 712 is disposed within the lower waste container 202.

The float elements 708, 712 are preferably doughnut shaped and buoyant such that they float on a surface of the liquid stored in each respective canister 218, 224. Both float elements are slidably mounted to the sensor rod 702. The upper reference element 706 is disposed adjacent the bottom 230 of the upper waste container 200 and the lower reference element 710 is disposed adjacent the bottom 232 of the lower waste container 202. Preferably, the reference elements 706, 710 are also disposed outside of each respective canister 218, 224, such that they do not come into contact with liquid. However, the reference elements 706, 710 could be disposed within each respective canister 218, 224 and not buoyant, such that they sink to the bottom of each respective canister 218, 224. The sensor rod 702, elements 706, 708, 710, 712, and transceiver 704 may be implemented with "M-Series Digital" components available from MTS Systems Corporation, Sensor Division, located in Cary, N.C.

As stated above, due to their proximity to the sensor rod 702, the elements 706, 708, 710, 712 cause return pulses to reflect back towards the transceiver 704 in response to the interrogation pulse. Specifically, the upper float element 706 causes an upper float return pulse, the upper reference element 708 causes an upper reference return pulse, the lower float element 710 causes a lower float return pulse, and the lower reference element 712 causes a lower reference return pulse. The transceiver 704 receives these return pulses caused by the elements 706, 708, 710, 712. Since the elements 706, 708, 710, 712 are spaced apart from one another, the pulses are received at the transceiver 704 at different times. The delays between the times are generally proportional to the amount of spacing between the elements 706, 708, 710, 712. Therefore, the delays are utilized to estimate the amount of liquid and other waste material in each canister 218, 224, as is described in greater detail below.

Figure 39:
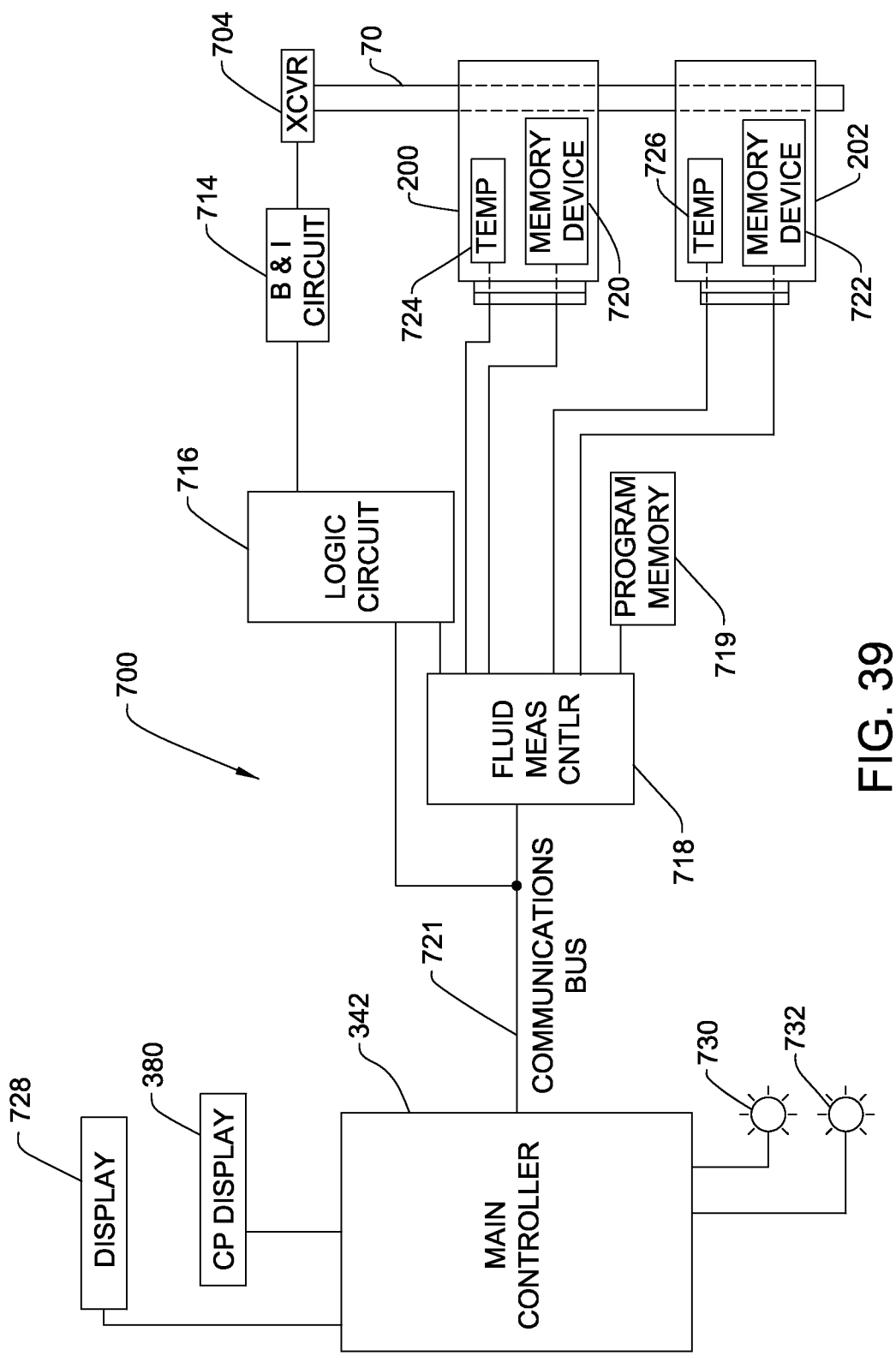
FIG. 39 is an electrical block diagram a level sensing system.

Upon the generation of the interrogation pulse and receipt of the subsequent return pulses transceiver 704 produces a transceiver signal. The transceiver signal provides a momentary state change (e.g., a logical high pulse) in real-time for the interrogation pulse and each return pulse. Thus, each time an interrogation pulse is emitted and four return pulses are received, five (5) distinct momentary state changes are output. In the preferred embodiment, as shown in FIG. 39, the transceiver 704 is electrically connected to a buffering and isolation circuit 714. The buffering and isolation circuit 714 receives the transceiver signal and buffers the transceiver signal to improve the waveforms. The buffering and isolcation circuit 714 also electro-optically isolates the transceiver 704 from the remaining circuitry.

The system 700 further includes a logic circuit 716. The logic circuit 716 is electrically connected to the buffering and isolation circuit 714, and thus in communication with the transceiver 704. The logic circuit 716 is preferably implemented utilizing a field-programmable gate array (FPGA). One suitable FPGA is the Spartan-3 manufactured by Xilinx, Inc., headquartered in San Jose, Calif. Of course, those skilled in the art realize other suitable techniques and devices to implement the logic circuit 716.

The logic circuit 716 digitally filters the transceiver signal received from the transceiver 704. Specifically, the logic circuit 716 preferably acts as a double-stage finite impulse response (FIR) filter. This filter acts as a low-pass filter, i.e., eliminating higher frequencies, to give an average reading for each return pulse time. Thus, the effect of the movement of the liquids within the containers 200, 202 is lessened. After filtering, the logic circuit 716 also generates time data corresponding to the times of the interrogation pulse and the return pulses. Said another way, the logic circuit 716 provides a numeric value for each time which is used in further computations. The logic circuit 716 measures the elapsed time from the receipt of the momentary state change representative of the interrogation pulse to receipt of the momentary state change representative of the receipt of each return pulse. Thus for each momentary state change representative of the receipt of a return pulse, the logic circuit 716 outputs a data packet in which data is contained indicating the elapsed time between transmission of the interrogation pulse and the receipt of the return pulse. Therefore, four (4) such data packets, one for each return pulse, are output from the logic circuit 716.

A liquid measuring controller 718 is electrically connected to the logic circuit 716 for transmitting and receiving data from the logic circuit 716. The liquid measuring controller 718 is preferably a microprocessor based device, such as a microcontroller. A program memory 719 is also electrically connected to the liquid measuring controller 718. The program memory 719 contains a non-volatile copy of the software program that is run by the logic circuit 716, which has a volatile memory which may clear upon loss of power. Therefore, upon startup, the liquid measuring controller 718 reads the program from the program memory 719 and transmits the program to the logic circuit 716. The liquid measuring controller 718 and the logic circuit 716 are also electrically connected to a communications bus 721. The communications bus 721 is electrically connected to the main controller 342. Thus, the liquid measuring controller 718 and the logic circuit 716 are in communication with the main controller 342. As such, the main controller 342 may also be considered to be in communication with the transceiver 704.

The main controller 342 utilizes the elapsed time data from the logic circuit 716 to estimate a volume of liquid in the lower waste container 202 and a volume of liquid in the upper waste container 200. By utilizing the times provided by the transceiver 704 and the basic geometry of each container 200, 202, the main controller 342 provides a fairly accurate estimation of the volume stored in each container 200, 202. However, other factors may affect the accuracy of this estimation. These factors include, but are not limited to, normal variations in the dimensions of the waste containers 200, 202 from a mathematical model as well as variations in the dimensions resulting from the manufacturing process, volumetric expansion and contraction of the containers and the liquid due to temperature, variation caused by the electronics of the transceiver 704, and disturbances in the liquid stored in the container 200, 202 caused by the flow of air within the container 200, 202.

Since the sensor rod 702 is essentially linear, the basic relationship between times t of the return pulses and distances Z of the return pulses is also linear. This basic relationship is developed from the general equation for a line (y=mx+b) and can be described as $$t = Z \cdot G + b,$$

where G is the gradient (or slope) of the linear relationship between time t and distance Z in the sensor rod 702 and b represents the time t when the distance Z equals zero (i.e., at the very top of the sensor rod 702). Applying the above equation to each element 706, 708, 710, 712 provides $$t_{UFE} = Z_{UFE} * G + b,$$

$$t_{URE} = Z_{URE} * G + b,$$

$$t_{LFE} = Z_{LFE} * G + b, \text{ and}$$

$$t_{LRE} = Z_{LRE} * G + b,$$

where "UFE" refers to the upper float element 708, "URE" refers to the upper reference element 706, "LFE" refers to the lower float element 712, and "LRE" refers to the lower reference element 710. By first solving for the distances $Z_{UFE}$, $Z_{URE}$, $Z_{LFE}$, $Z_{LRE}$, the volume of liquid in each container 200, 202 may be estimated. The gradient G is not affected by temperature; however, b is affected by temperature. In the preferred embodiment, the transceiver 704 is preprogrammed by its manufacturer with the gradient G of the transceiver 704/sensor rod 702 combination. This gradient G may then be communicated from the transceiver 704 to the main controller 342 for use in volumetric calculations.

In the preferred embodiment, an upper memory device 720 is coupled to the upper waste container 200 and a lower memory device 722 is coupled to the lower waste container 202. The liquid measuring controller 718 is in communication with the memory devices 720, 722 and receives data stored on the devices 720, 722. The memory devices 720, 722 are preferably Non-volatile Random Access Memory (NVRAM) devices, however, other suitable memory devices are known to those skilled in the art. The memory devices 720, 722 each store a series of calibration data points. In the upper memory device 720, each calibration data point correlates a known volume stored in the upper container 200 to the difference between the upper reference element time $t_{URE}$ and upper float element time $t_{UFE}$ when the known volume is in the upper container 200 at a known, calibration temperature $T_{CAL}$. In the lower memory device 722, each calibration data point correlates a known volume stored in the lower container 202 to the difference between the lower reference element time $t_{LRE}$ and lower float element time $t_{LFE}$ when the known volume is in the lower container 200 at the known calibration temperature $T_{CAL}$. The data stored in each memory device 720, 722 is unique to that specific container 200, 202 for which it is coupled to.

As described above, the canisters 218, 224 each define respective chambers 220, 226. In the preferred embodiment, the interior chambers 220, 226 of the waste containers 200, 202 are each generally shaped as a frustum of a right circular cone. However, the bottom of each chamber 220, 226 is irregularly shaped (i.e., not shaped like the bottom of the frustum of the right circular cone). Therefore, each container 200, 202 is prefilled with an amount of liquid to provide a prefill level, which is a "zero point" or "tare point" from which to make volumetric calculations. In other words, the prefilled liquid forms the bottom of the frustum of the right circular cone. The distances $X_U$, $X_L$ between the prefill level and the respective reference element 708, 712 may be stored in the respective memory device 720, 722. The prefilled liquid also functions to lift the float elements 706, 710 up from the bottom of each chamber 220, 226. Those skilled in the art realize that the volume of liquid stored in each container 200, 202 may be computed for other shapes, including, but not limited to, cylindrical or spherical shapes.

The liquid measuring system 700 of the preferred embodiment also includes an upper temperature sensor 724 for sensing a temperature of the upper waste container 200 and a lower temperature sensor 726 for sensing a temperature of the lower waste container 202. Preferably, the lower temperature sensor 726 is coupled to the lower waste container 202 and the upper temperature sensor 724 is coupled to the upper waste container 200. The temperatures sensors 724, 726 may be implemented as thermocouples or RTDs, which are typically placed in contact with the item being measured (e.g., the containers 200, 202). Alternatively, the temperature sensors 724, 726 may be an infrared temperature sensor that need not contact the containers 200, 202. The temperatures sensors 724, 726 are in communication with the main controller 342 such that the main controller 342 receives the temperature of each container 200, 202.

The memory devices 720, 722 and the temperature sensors 724, 726 are electrically connected to the liquid measurement controller 718. Thus, the memory devices 720, 722 and the temperature sensors 724, 726 are in communication with the main controller 342. A pair of connectors (not numbered), one connector for each container 200, 202, allows for the electrical connection and disconnection of the memory devices 720, 722 and the temperature sensors 724, 726 from the liquid measurement controller 718. Therefore, when container 200, 202 is replaced, a different memory device 720, 722 (having different, unique data points) and temperature sensor 724, 726 are then in communication with the main controller 342.

The main controller 342 utilizes the data points provided by the memory devices 720, 722 and temperatures provided by the temperature sensors 724, 726, along with the interrogation pulse/return pulse elapsed time values to generate its estimates of the volumes stored in the containers 200, 202. The main controller 342 may also use the coefficient of thermal expansion (CTE) of the containers 200, 202 in its estimate of the volume stored in each container 200, 202.

In the preferred embodiment, the estimated volume $V_{EST}$ of the liquid stored in each container is the sum of the volume $V_C$ based on the calibration data points at the calibration temperature $T_{CAL}$ and the volume change $\Delta V$ due to temperature variation. In short, $$V_{EST} = V_C + \Delta V.$$

To compute $V_C$ for each tank, the main controller calculates the difference between the time of the float element $t_{UFE}$, $t_{LFE}$ from the time of the reference element $t_{URE}$, $t_{LRE}$. The main controller then interpolates the volume $V_C$ by using the calculated difference and data points from the appropriate memory device 720, 722. To compute $\Delta V$ for each tank, the main controller utilizes the formula $$\Delta V = \pi * h * \frac{1}{3} * \begin{bmatrix} (2 * R^2 * CTE * \Delta T) + (R^2 * CTE^2 * \Delta T^2) + \\ (2 * R * r * CTE * \Delta T) + \\ (R + r + CTE^2 + \Delta T^2) + (2 * r^2 * CTE * \Delta T) + \\ (r^2 * CTE^2 * \Delta T^2) \end{bmatrix},$$

which is based on the formula for a frustum of a right circular cone. The coefficient of thermal expansion CTE for each tank may be stored in the memory devices 720, 722 or the main controller 342. The height h represents the distance between the appropriate float element 706, 710 and the prefill level and can be computed using the distances $X_U$, $X_L$ stored in the memory devices 720, 722. The lower radius r represents the radius of the appropriate interior chamber 220, 226 at the prefill level and may also be stored in the memory devices 720, 722. The upper radius R may be computed using the formula $$R = h*(R_T - r)/H + r,$$

where $R_T$ is the radius of the top of the chamber 220, 226, and H is the distance between the top of the chamber (where $R_T$ is measured) and the prefill level. These values may be stored in the memory devices 720, 722 or the main controller 342. Finally, $\Delta T$ is the temperature difference between the temperature T measured by the temperature sensors 724, 726 and the calibration temperature $T_{CAL}$.

Figure 40:
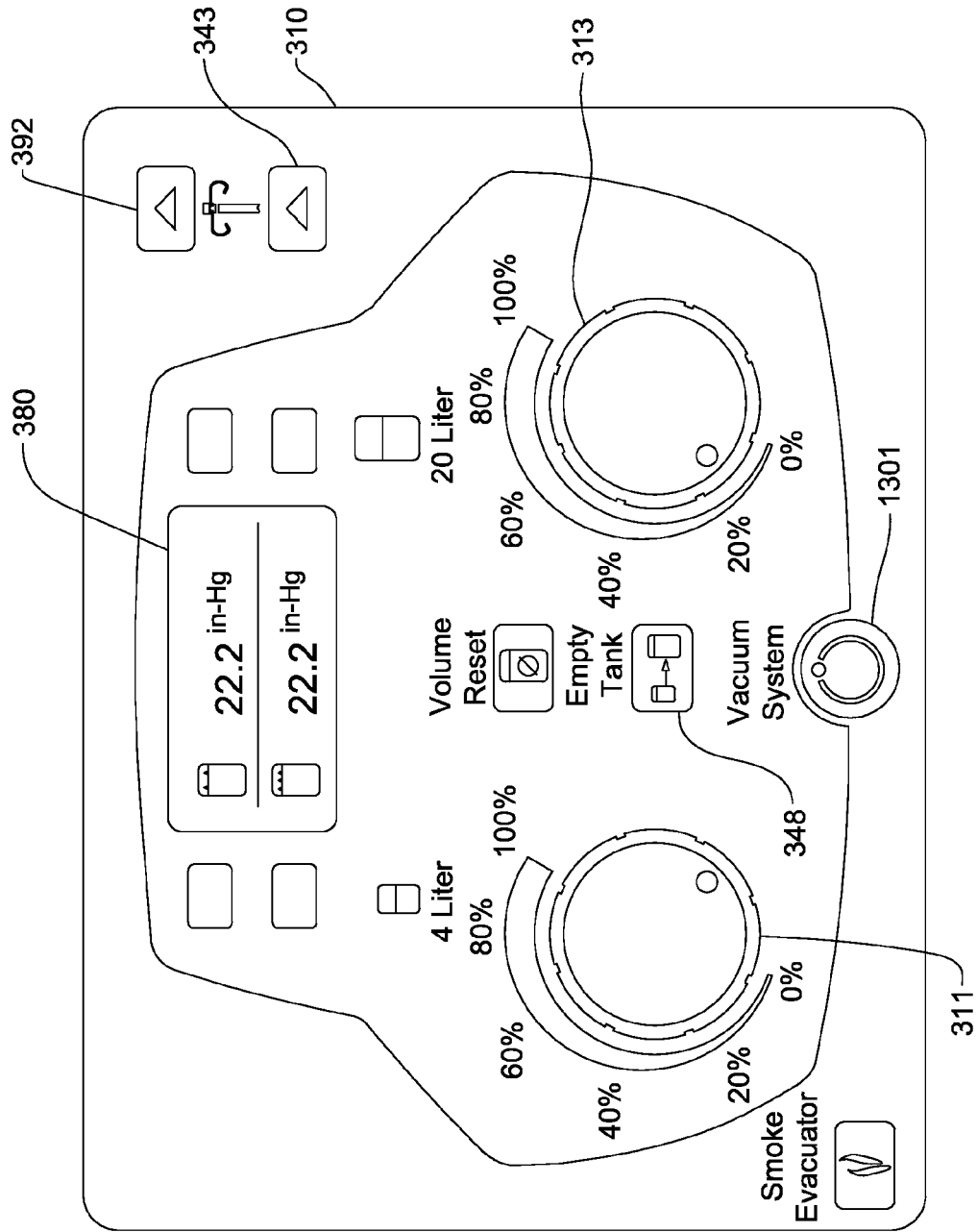
FIG. 40 is a graphical representation of a control panel of the waste collection unit.

Once the estimate of the volumes $V_{EST}$ for each container 200, 202 is calculated by the main controller 342, the volumes $V_{EST}$ are communicated to the control panel display 380 and/or a volume display 728. The displayed volumes may be utilized by health care professionals and other users of the mobile collection unit 102. A detailed illustration of the control panel 310 of the preferred embodiment, including the control panel display 380, is shown in FIG. 40. An illustration of the volume display 728 is shown in FIG. 40A. The volume display 728 is preferably housed by a display housing (not numbered) with axes that allow 270 degrees or greater rotation and/or 15 degrees or greater tilting to accommodate a wide range of view positions.

The mobile collection unit 102 may also include an upper canister lamp 730 and a lower canister lamp 732, each in communication with the main controller 342. The upper canister lamp 730 illuminates the upper canister 218 and the lower canister lamp 732 illuminates the lower canister 224. The illumination of the canisters 218, 224 may be seen through the transparent windows 362, 364. The canister lamps 730, 732 may be activated in response to the estimated volume of the liquid in each canister 218, 224 as calculated by the main controller 342. The canister lamps 730, 732 may each be capable of displaying different color light, for example, having multiple light emitting diodes (LEDs) of different colors. In the preferred embodiment, the canister lamps 730, 732 may display a green color light when the volume of liquid in each respective canister 218, 224 is below a predetermined level and display a red color light when the volume of liquid is at or above the predetermined level. This allows users of the mobile collection unit 102 to easily see when one or both of the canisters 218, 224 are reaching a "full" point.

VIII. Smoke Evacuation

Figure 41:
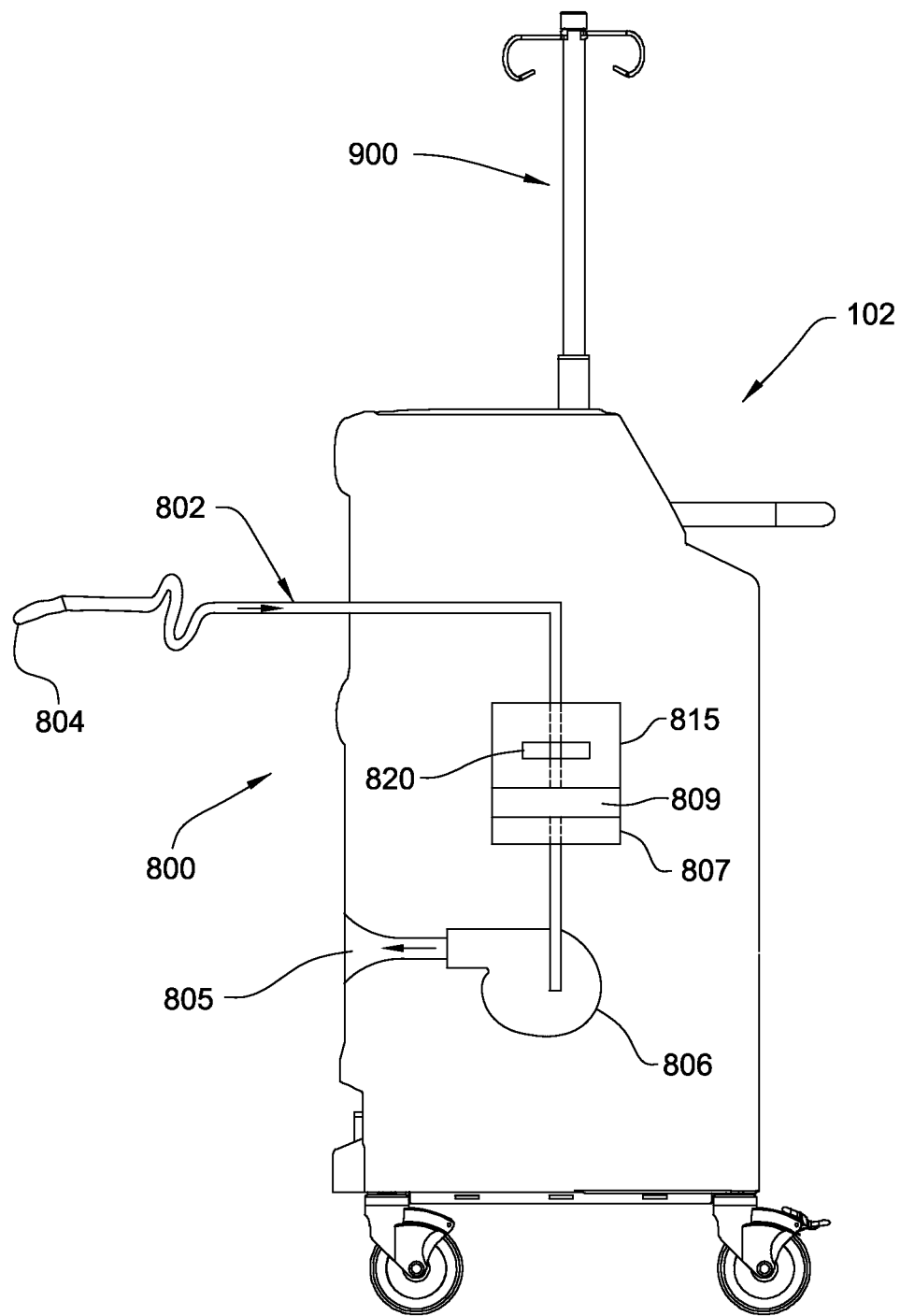
FIG. 41 is a schematic view of the waste collection unit illustrating the flow of fluid into the a smoke evacuation system.

Referring to FIG. 41, the waste collection unit 102 also includes a smoke evacuation system 800. The smoke evacuation system 800 is typically utilized for removing smoke from a fluid, such as air, during a surgical operation. However, other uses for the system 800 are evident to those skilled in the art.

The smoke evacuation system 800 includes a smoke conduit 802. The smoke conduit 802 includes an inlet 804, where the fluid is drawn into the conduit 802, and an outlet 805, where fluid is exhausted from the conduit 802. The fluid is preferably air, along with the smoke that is generated during the medical procedures, e.g., surgical operations. A blower 806 is in fluid communication with the smoke conduit 802 for drawing the fluid into the inlet 804 when the blower 806 is rotated. Those skilled in the art realize that the blower 806 may alternatively be referred to as a "fan" or a "pump". The blower 806 includes a blower motor 808 for operating the blower 806. In the preferred embodiment, the blower 806 may be a multi-stage centrifugal blower and the blower motor 808 may be a brush motor. However, those skilled in the art realize alternative embodiments utilizing different implementations of blower 806 and blower motor 808.

Figure 42:
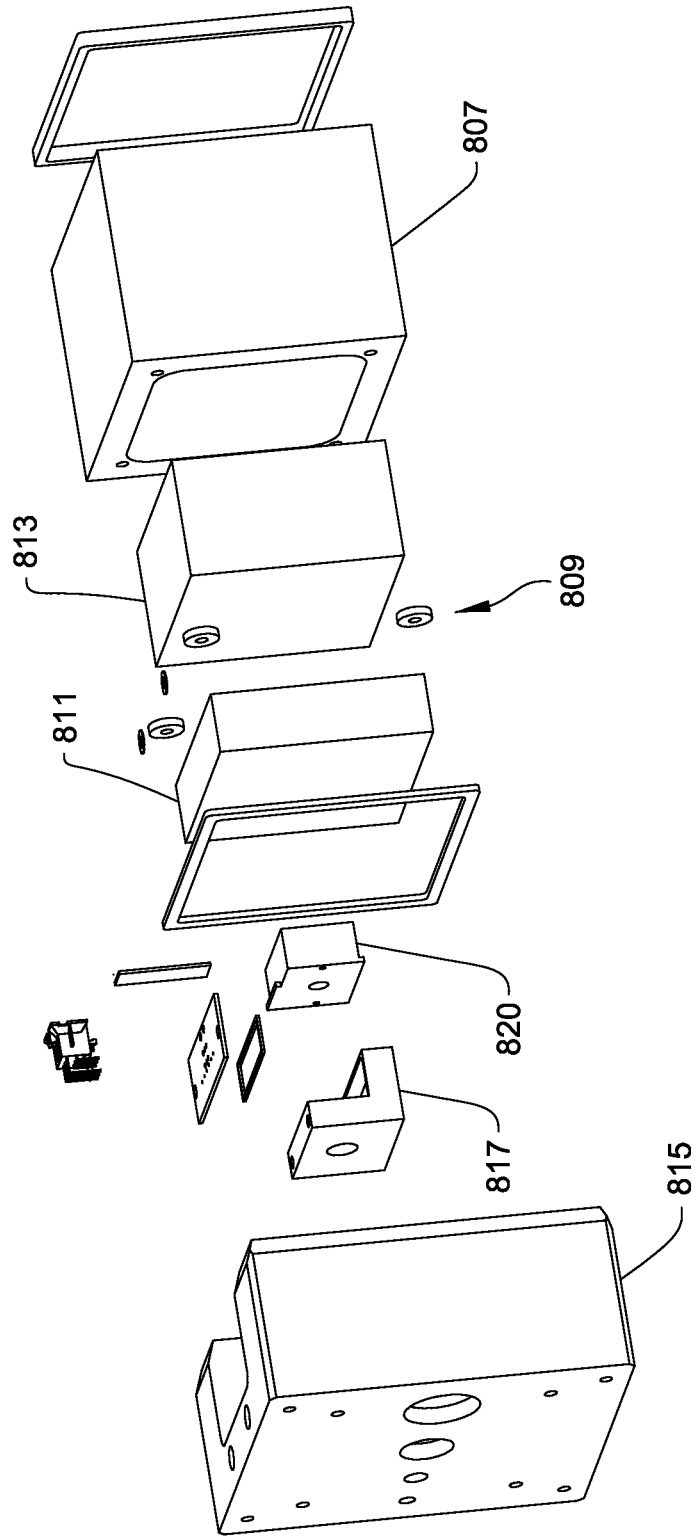
FIG. 42 is an exploded perspective view illustrating a filter, housing, and smoke sensor of the smoke evacuation system.

The smoke evacuation system 800 also includes a filter 809 in fluid communication with the smoke conduit. The filter 809 filters smoke from the smoke conduit, such that "clean" air is exhausted from the outlet 805. The filter 809 may be implemented as a plurality of filters and/or a plurality of filter elements 811, 813. In the preferred embodiment, as shown in FIG. 42, the filter 809 includes a pair of filter elements. One filter element 811 includes activated carbon and the other filter element 813 is a ULPA media. The filter 809 is preferably supported by a filter housing comprising a filter enclosure 807 connected to a filter cap 815 to form a replaceable unit.

Figure 43:
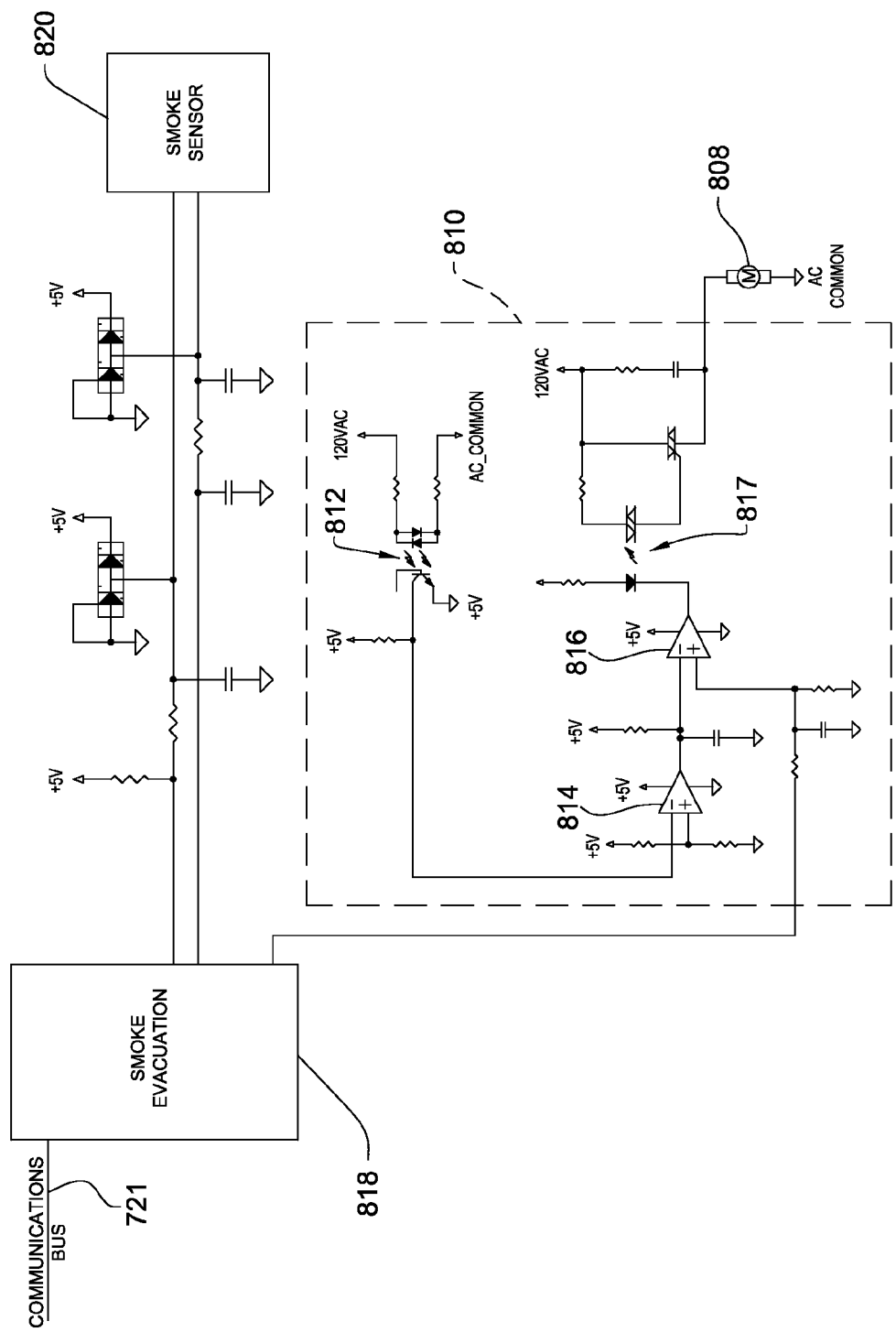
FIG. 43 is an electrical schematic showing a circuit for a smoke evacuation system.

Referring now to FIG. 43, a blower control circuit 810 is electrically connected to the blower motor 808 for providing electrical power to the blower motor 808 and controlling a speed of the blower 806. The blower control circuit 810 of the preferred embodiment performs alternating current (AC) phase control to control the speed of the blower 806. Furthermore, the blower control circuit 810 of the preferred embodiment electrically isolates, using optical isolation devices, the AC power utilized to drive the blower motor 808 from the DC power utilized in logic circuitry.

In the preferred embodiment, the blower control circuit 810 includes an AC input photocoupler 812. The AC input photocoupler 812 includes a pair of light emitting diodes (LEDs) (not numbered) connected inversely and in parallel. The LEDs drive a phototransistor (not numbered) having a base, a collector, and an emitter. One suitable AC input photocoupler 812 is the model number H11A11 manufactured by Fairchild Semiconductor, headquartered in South Portland, Me. A 120 VAC supply is electrically connected to the LEDs. The emitter of the phototransistor is grounded and the collector is pulled to DC power through a resistor. The collector the phototransistor generates a narrow pulse that is in phase with the AC power of the 120 VAC supply and represents the zero crossing of the AC power.

The blower control circuit 810 also includes a first comparator 814 and a second comparator 816. Each comparator 814, 816 includes an inverting input, a non-inverting input, and an output. The inverting input of the first comparator 814 is electrically connected to the collector of the phototransistor of the AC input photocoupler 812. The non-inverting input of the first comparator 814 is electrically connected to a reference voltages set to one-half the value of the DC power. The output of the first comparator 814 generates a 0 to 3 volt sawtooth waveform that is in phase with the AC power and whose frequency is twice that of the AC power. The output of the first comparator 814 is electrically connected to the inverting input of the second comparator 816. An analog signal (as described further below), is electrically connected to the non-inverting input of the second comparator 816. The output of the second comparator 816 generates a square wave that is in phase with the AC power and whose pulse width is directly proportional to the amplitude of the analog signal. The output of the second comparator 816 is applied to a solid state switch 817 that supplies power to the blower motor 808. The amount of power supplied to the blower motor 808, and thus the speed of the blower 806, is directly proportional to the amplitude of the analog signal.

The smoke evacuation system 800 also includes a smoke evacuation controller 818. The smoke evacuation controller 818 is preferably a microprocessor based device such as a microcontroller. However, those skilled in the art realize other techniques to implement the smoke evacuation controller 818. In the preferred embodiment, the smoke evacuation controller 818 produces a pulse-width modulated (PWM) signal. The PWM signal provides pulses, of varying width. The widths of the PWM signal vary based on the desired power to be applied to the blower motor 808. Alternatively, a separate PWM circuit (not shown) may be in communication with the smoke evacuation controller 818 to generate the PWM signal.

The smoke evacuation controller 818 is in communication with the blower control circuit 810. Specifically, in the preferred embodiment, the PWM signal is converted to the analog signal described above. The analog signal is proportional to the PWM signal, and thus, the amount of power supplied to the blower motor 808 is directly proportional to the PWM signal.

A smoke sensor 820 is in fluid communication with the smoke conduit 802 and is electrically connected to the controller 818. Preferably, the smoke sensor 820 is disposed inline with the smoke conduit 802 such that the fluid flowing through the conduit 802 may be sensed before passing through the filter 809. In the preferred embodiment, the smoke sensor 820 is disposed between the filter enclosure 807 and the filter cap 815 such that the smoke sensor 820 senses the fluid prior to filtering by the filter elements 811, 813. Said another way, the smoke sensor 820 is upstream from the filter elements 811, 813. Since the smoke sensor is disposed within the filter enclosure 807, the smoke sensor 820 is replaced along with the filter 809. As smoke sensors 820 may become dilapidated over time and use, periodic replacement of the smoke sensor 820, along with the filter 809, helps ensure accurate readings from the smoke sensor 820. Referring to FIG. 42, a cradle 817 supports the smoke sensor 820 inside the filter enclosure 807 and filter cap 815 of the replaceable unit such that replacement includes inserting a new replaceable unit complete with a new filter 809 and a new smoke sensor 820 disposed in a new filter enclosure 807 and a new cap 815.

The smoke sensor 820 senses an amount of smoke traveling through the smoke conduit 802 and produces a smoke sensor signal which corresponds to the amount of smoke in the smoke conduit 802. The smoke sensor signal is then communicated to the smoke evacuation controller 818. In the preferred embodiment, the smoke sensor 820 is further includes an infrared (IR) lamp (not shown) for generating IR light and an IR detector (not shown) for sensing the IR light generated by the IR lamp. The fluid in the smoke conduit 802 passes between the IR lamp and the IR detector. When smoke is present in the fluid, the particles of the smoke will reflect the IR light received by the IR detector. Thus, the smoke sensor 820 may determine the presence of smoke in the smoke conduit 802 and relay this determination to the controller 818.

The controller 818 varies the PWM signal in response to the smoke sensor signal. In the preferred embodiment, the controller 818 utilizes three discrete PWM signals in an automatic mode. In the automatic mode, a first PWM signal is provided to the blower control circuit 810, which in turn provides electrical power at a first level to the blower motor 808 such that the blower 806 rotates at a first speed. At this first speed, suction at the inlet 804 of the smoke conduit 802 is kept at a minimal level. That is, just enough suction is provided to draw fluid into the smoke conduit 802, such that smoke can be sensed by the smoke sensor 820.

As described above, the controller 818 receives a smoke sensor signal representing an amount of smoke sensed in the smoke conduit 802. When smoke is detected in the smoke conduit 802, i.e., when the amount of smoke exceeds a predetermined limit, the controller 812 will provide a second PWM signal to the blower control circuit 810. The circuit 810 then increases electrical power to the blower motor 808 to a second level greater than the first level. The second level is used to quickly accelerate the rotation of the blower. After operating the blower motor 808 at the second level, the controller 812 then provides a third PWM signal to decrease electrical power to the blower motor 808 to a third level. The third level is less than the second level, but greater than the first level. At the third level, the blower 806 will rotate at a second speed, which is faster than the first speed.

With the blower 806 operating at the second speed, the blower 806 will generate more suction at the inlet 804 than when the blower 806 is operating at the first speed. This allows smoke, which has been detected by the smoke sensor 820, to be quickly evacuated from the surgical operation and filtered by the filter 809. While the blower 806 is operating at the second speed, the smoke sensor 820 continues to evaluate the fluid for smoke. After the smoke in the smoke conduit 802 is less than a predetermined limit, the controller 820 will reestablish the first PWM signal to the blower control circuit 810 to return the blower motor 808 to the first level of operation, and the blower 806 will be reduced to the first speed.

By operating the blower 806 at the first (i.e., slow) speed, noise caused by the blower 806 is noticeably reduced. This helps maintain a more peaceful environment when delicate surgical operations are being performed. However, by quickly ramping up to the second and third (i.e., faster) speeds, the smoke evacuation system 800 retains the performance level needed to quickly evacuate smoke from the surgical area. In some embodiments, this "automatic" mode of smoke evacuation may be set by the user on the control panel 310 or can be continuously operating. In addition, the user may be able to vary the speed of the blower motor 808 manually.

The smoke evacuation system 800 may also include a differential pressure sensor (not shown) for sensing a differential pressure across the filter 809 or filter elements 811, 813. The differential pressure sensor is in communication with the main controller 342 and communicates the differential pressure to the main controller 342. When differential pressure reaches a predetermined level, such as when the filter 809 or filter elements 811, 813 begin to get clogged, the main controller 342 may then alert a user of the mobile waste collection unit 102 via the control panel display 380. The differential pressure sensor may be an analog-type, providing a number representing the differential pressure, or a switch, which provides a digital signal when the differential pressure reaches the predetermined level.

IX. Adjustable IV Pole with Auto-Down Feature

Figure 44:
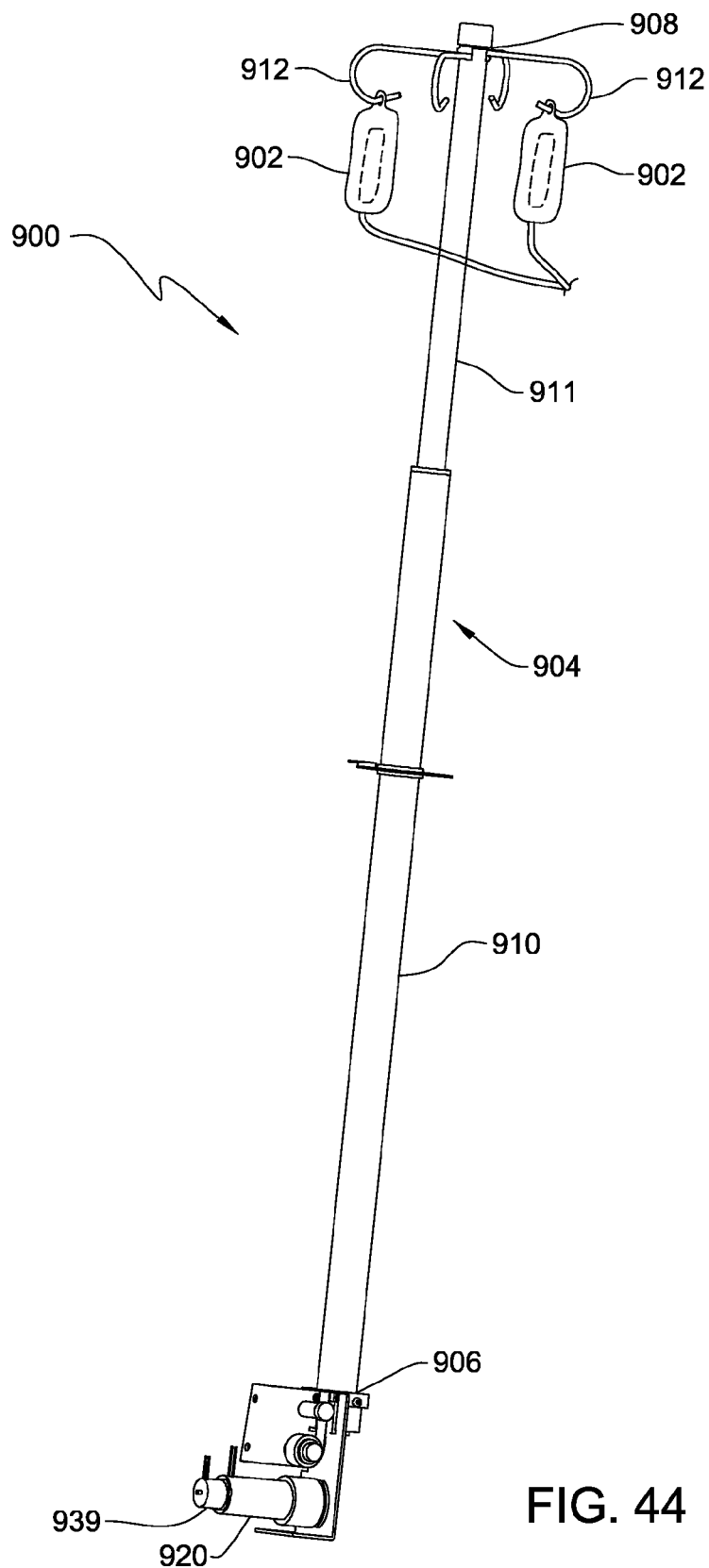
FIG. 44 is a perspective view of an IV bag support pole assembly.

The mobile waste collection unit 102 includes an intravenous (IV) bag support pole assembly 900. Referring now to FIG. 44, the assembly 900 is configured to support at least one IV bag 902. IV bags 902, when used in surgery, typically contain an irrigation fluid used by a surgeon. The assembly 900 includes an IV bag support pole 904 having a proximal end 906 and a distal end 908. The pole 904 includes a plurality of pole segments 910, 911 telescopingly interfaced together, such that the pole 904 is adjustable between a fully extended position and a fully retracted position. At least one IV bag hook 912 is coupled to the distal end 908 of the pole 904 for supporting the IV bag or bags 902. Preferably, four hooks 912 are provided, but the number of hooks 912 may vary.

There are several advantages to the telescopic IV bag support pole 904. First, the IV bag hooks 912 may be brought down to a conveniently low position, allowing medical personnel, especially those personnel having a smaller stature, to attach IV bags 902, which are often heavy. Second, the IV bag hooks 912 and attached IV bags 902 may be lifted to a high position, thus generating greater head pressure, which is often advantageous in surgical procedures. Also, the mobile waste collection unit 102 is more easily movable when the IV bag support pole 904 is in the fully retracted position.

Figure 45:
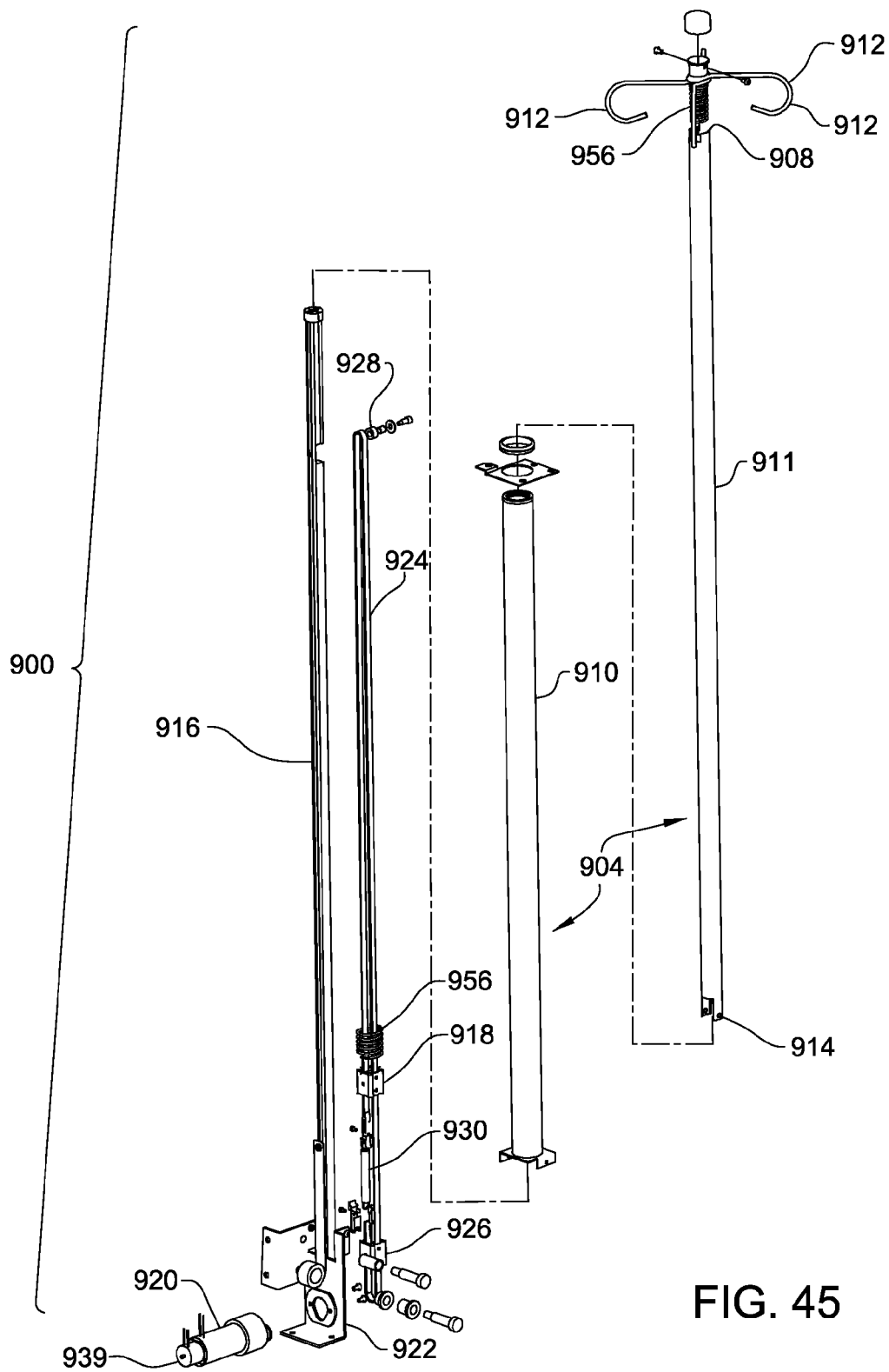
FIG. 45 is an exploded perspective view of the IV bag support pole assembly.

In the preferred embodiment, the pole segments 910, 911 include a fixed pole segment 910 and a movable pole segment 911. The movable pole segment 911 fits inside the fixed pole segment 910 when the pole is in the fully retracted position. Referring now to FIG. 45, the movable pole segment 911 has two ends: a lower end 914 and the distal end 908. A base shaft 916 is disposed in the fixed pole segment 910. The movable pole segment 911, when retracted, also surrounds base shaft 916. A first block 918 is slidable along the base shaft 916 and connected to the lower end of the movable pole segment 911, thus allowing the movable pole segment 911 to telescopingly extend and retract from the fixed pole segment 910.

The assembly 900 also includes a direct current (DC) motor 920 supported by a motor mount 922. The DC motor 920 has a rotatable shaft (not labeled) operable by an electrical portion (not labeled). The electrical portion of the DC motor 920 utilizes direct current to effectuate rotation of the rotatable shaft. The DC motor 920 is preferably bidirectional, such that the rotatable shaft may rotate in either direction. One suitable DC motor 920 is the Model GM9236, manufactured by Pittman, a PennEngineering Company, located in Harleysville, Pa. Of course those skilled in the art realize other suitable motors and also realize that mechanical linkages may provide the bidirectional rotation of the rotatable shaft without the need for the DC motor 920 to be bidirectional.

Figure 47:
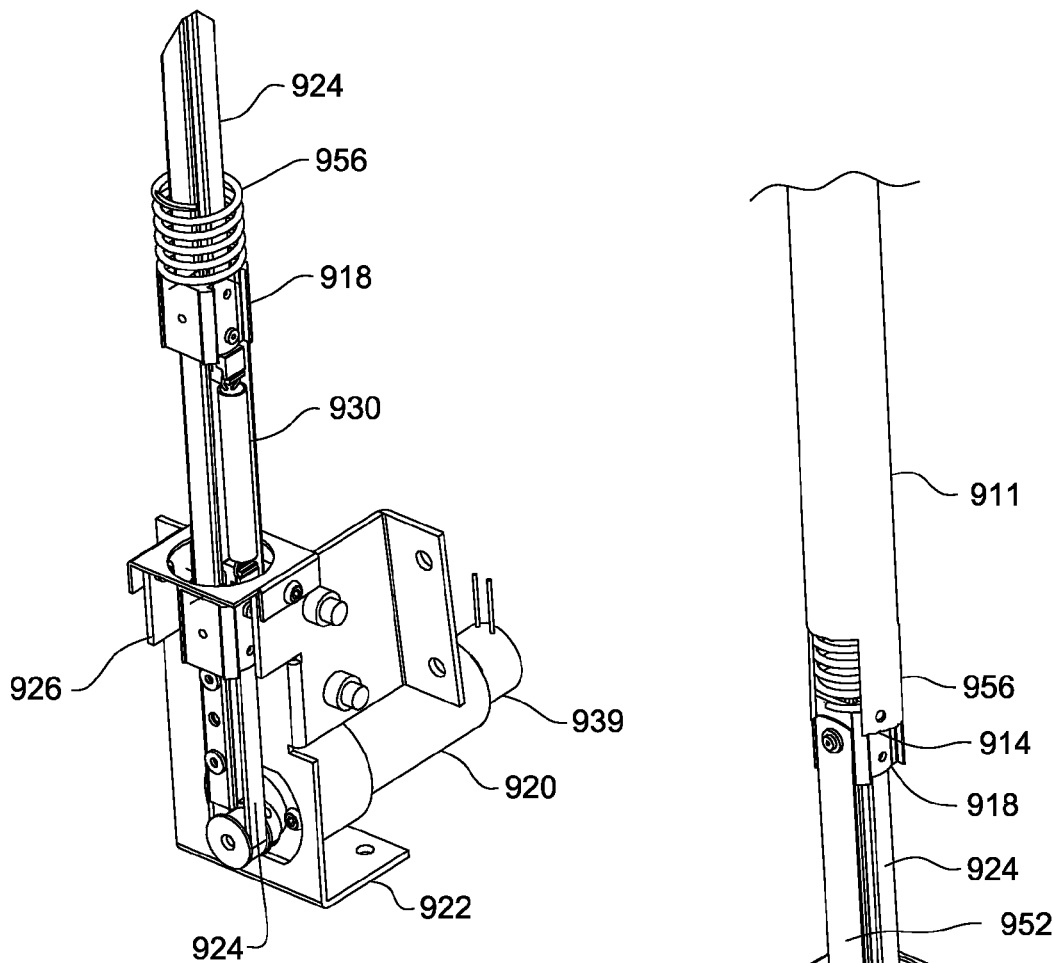
FIG. 47 is a perspective view of the lower portion of the IV bag support pole assembly showing a connecting spring providing tension on a belt.

The rotatable shaft of the DC motor 920 is operably connected to the movable pole segment 911. In the preferred embodiment, the rotatable shaft is operably connected to the first block 918 for slidably actuating the first block 918, and thus, actuating the movable pole segment 911. A belt 924 provides the connection between the first block 918 and the DC motor 920. The belt 924 preferably has a first end (not labeled) and a second end (not labeled). The first end is connected to the first block 918 while the second end is connected to a second block 926. The second block 926, like the first block 918, is slidable along the base shaft 916. A roller 928 is connected to the base shaft 916 near a top of the base shaft 916. The belt 924 wraps around both the roller 928 and the rotable shaft of the DC motor 920. As best seen in FIG. 47, a connecting spring 930 links the first block 918 to the second block 926, thus forming a complete loop of spring 930, blocks 918, 926, and belt 924. The spring 930 provides tension on the belt 924, such that the rotatable shaft of the DC motor 920 may actuate the belt 924. A pulley (not numbered) is disposed around the motor shaft. The belt 924 is partially looped around the pulley. The pulley holds the belt 924 to the motor shaft.

Figure 48A:
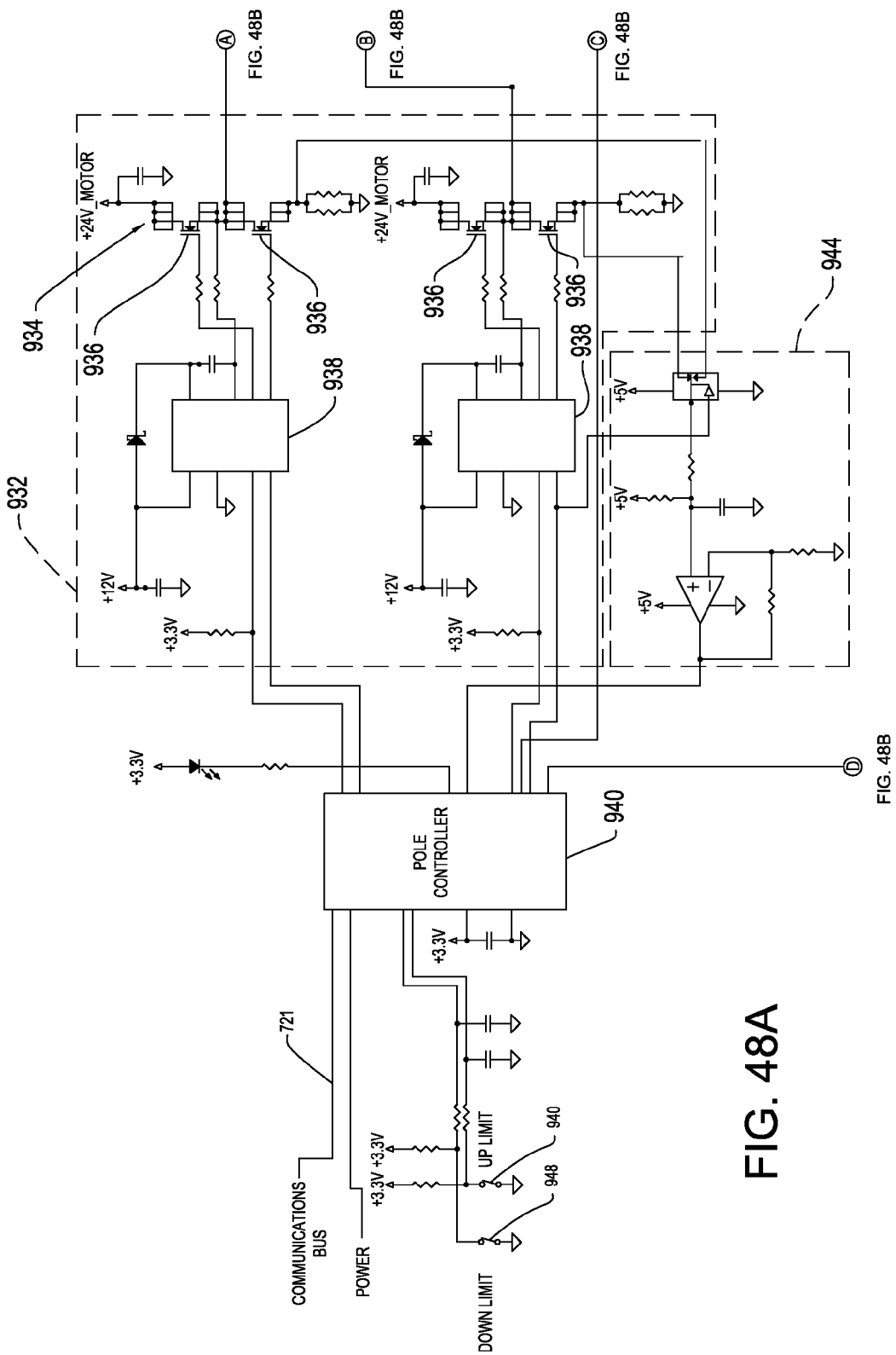
FIG. 48A is an electrical schematic showing a motor control circuit, a pole controller, and a power monitoring circuit.
Figure 48B:
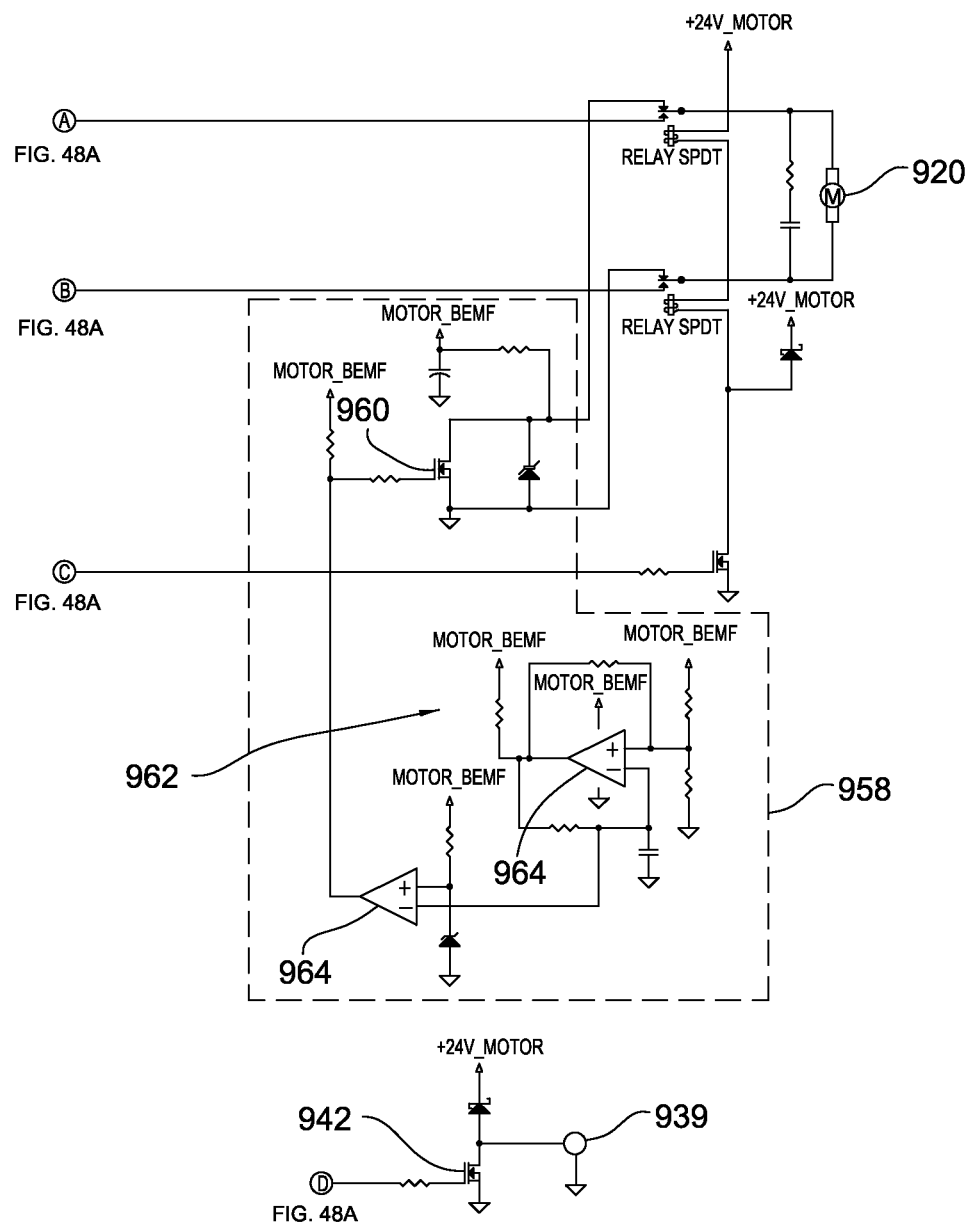
FIG. 48B is an electrical schematic showing a DC motor and a slowdown circuit.

The electrical portion of the DC motor 920 includes a pair of electrical leads (not labeled). Referring now to FIGS. 48A and 48B, a motor control circuit 932 is electrically connected to the electrical portion of the DC motor 920 at the electrical leads for selectively providing motor power to the DC motor 920. In the preferred embodiment, the motor control circuit 932 includes an H-bridge 934 utilizing four power MOSFETs 936, such as the model number IRF7484 manufactured by International Rectifier, of El Segundo, Calif. The H-bridge 934 allows for bidirectional operation of the DC motor 920 by changing the direction of the flow of current to the DC motor 920. The power MOSFETs 936 are driven by a pair of half-bridge driver chips 938, such as the model number IR2183, also manufactured by International Rectifier.

A brake 939 is utilized to maintain a current position of the pole, when the DC motor 920 is not operating. In the preferred embodiment, as shown in FIGS. 44 and 45, the brake 939 is electrically operated and connected to the DC motor 920 for locking the rotatable shaft in its current position. One suitable brake 939 is the model FB11, produced by Inertia Dynamics, LLC, located in Torrington, Conn.

Referring again to FIG. 48A, a pole controller 940 is utilized to control operation of the pole assembly 900. The pole controller 940 is electrically connected to the motor control circuit 932 for controlling operation of the motor control circuit. Specifically, in the preferred embodiment, the motor control circuit 932 is electrically connected to the bridge driver chips 938. The pole controller 940 is also electrically connected to the brake 939, via a MOSFET 942. The pole controller 940 will activate the brake 939 when the DC motor 920 is not active and deactivate the brake 939 when the DC motor 920 is active.

The pole controller 940 is also electrically connected to the communications bus 721, such that the pole controller 940 may communicate with the main controller 342. Referring to FIG. 80, the control panel 310 of the mobile waste collection unit 102, as described above, is in communication with the main controller 342. The control panel 310 includes a pair of pushbuttons 942, 943, preferably an "up" pushbutton 942 and a "down" pushbutton 943, for allowing a user to selectively control actuation of the pole 904. The pushbuttons 942, 943 are in communication with the pole controller 940, via the main controller 342 and the communications bus 721. The pole controller 940 sends control signals to the bridge driver chips 938 in response to receiving control signals from the pushbuttons 942, 943.

Referring again to FIG. 48A, a power monitoring circuit 944 is electrically connected to the motor control circuit 932 and the pole controller 940. The power monitoring circuit 944 monitors the motor power provided by the motor control circuit 932 to the DC motor 920. Specifically, the power monitoring circuit 944 of the preferred embodiment monitors an amount of current delivered by the motor control circuit 932. The power monitoring circuit 944 sends an overpower signal to the pole controller 940 in response to the motor power reaching a predetermined level. The pole controller 940 may then deactivate the power MOSFETs 936 of the motor control circuit 932 to avoid damaging the DC motor 920 or other electrical circuitry. Furthermore, the pole controller 940 may send a message to the control panel display 380, via the communications bus 721 and the main controller 342.

An up limit switch 946 and a down limit switch 948 may also be electrically connected to the pole controller 940. The limit switches 946, 948 are preferably coupled to the pole 904 to sense when the pole 904 is at the fully extended position and the fully retracted position. When reaching one of these positions, the associated switch 946 or 948 undergoes an open/closed state change. The open/closed state change of the switch 946 or 948 causes a change in the voltage across the switch. This voltage change is sensed by the pole controller. In response to the change in signal level, the pole controller deactivates the motor 920 to prevent damage to it or the components connected thereto.

Figure 46:
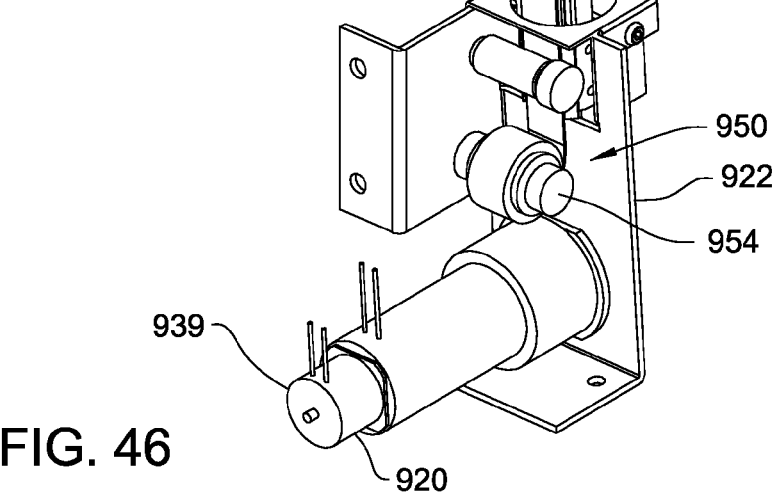
FIG. 46 is a perspective view of a lower portion of the IV bag support pole assembly showing a spring-loaded tape for retracting an IV bag support pole.

As best seen in FIG. 46, the assembly 900 further includes a spring mechanism 950 for telescopically retracting the pole 904 when power is unavailable to the DC motor 920 and/or brake 939. Typically, power becomes unavailable when the main electrical connection to the mobile waste collection unit 102 is unplugged. By retracting the pole 904, the mobile waste collection unit 102 is easier to move. Furthermore, when the pole 904 is retracted, it lessens the likelihood of collisions with door frames and other structures, which tend to bend the pole 904.

The spring mechanism 950 includes a spring-loaded tape 952 wrapped around a pin 954. The pin 954 is supported by the motor mount 922. An end of the tape 952 is connected to the first block 918. The spring mechanism 950 and tape 952 are sized to slowly retract the movable pole segment 911 at a rate of descent that doesn't cause damage to the various components of the assembly 900, provided that IV bags 902 or other items are not providing a downward force on the movable pole segment 911. Shock absorbing coils 956 are utilized to help create a "soft landing" for the movable pole segment 911.

However, should additional weight, such as IV bags 902, provide a downward force on the movable pole segment 911, the spring mechanism 950 and shock absorbing coils 956 may not be adequate to prevent damage to the assembly 900. Therefore, a slowdown circuit 958, as shown in FIG. 48B, is provided to slow retraction of the pole 904. The slowdown circuit 958 is electrically connected to the electrical portion of the DC motor 920. As described above, the rotatable shaft of the DC motor 920 is operably connected to the movable pole segment 911. The slowdown circuit 958 periodically resists rotation of the rotatable shaft of the DC motor 920 when the motor power is unavailable. Therefore, the slowdown circuit 958 slows retraction of the movable pole segment 911.

The rotatable shaft of the DC motor 920 will resist rotating when the electrical leads are shorted (i.e., electrically connected) together. Therefore, the slowdown circuit 958 includes a shorting switch 960 electrically connected between the pair of electrical leads. The shorting switch 960 shorts the pair of electrical leads together when the shorting switch 960 is activated. The shorting switch 960 is preferably implemented as a MOSFET, however, other suitable electrical components, such as a relay, may alternatively be utilized.

The slowdown circuit 958 also includes a shorting activation circuit 962. The shorting activation circuit 962 is electrically connected to the shorting switch 960 and produces a shorting signal to activate the shorting switch 960. The shorting activation circuit 962 is also electrically connected to the electrical portion of the DC motor 920. As the movable pole segment 911 drops (due to gravity and the spring mechanism 950), the rotable shaft of the DC motor 920 rotates and the DC motor 920 acts as a generator, creating an electromotive force (EMF). This EMF, commonly referred to as a "back EMF" or a "back torque" provides the electrical power for operation of the slowdown circuit 958 (including the shorting activation circuit 962 and the shorting switch 960).

The shorting activation circuit 962 primarily includes a pair of comparators 964 connected as shown in FIG. 48B. As the speed of the rotatable shaft of the DC motor 920 increases, the amplitude of the back EMF becomes high enough to supply power to the comparators 964. The comparators 964 are configured in such a way to generate a PWM signal whose duty cycle is proportional to the amplitude of the back EMF. The PWM signal is applied to the shorting switch 960. Once the back EMF voltage is high enough (i.e., past a predetermined level) to trigger the shorting switch 960, the leads of the DC motor 920 are shorted together and the rotatable shaft will resist rotation. Consequently, the speed of the DC motor 920 will be reduced and the back EMF will decrease. Thus, the PWM duty cycle will also decrease. The shorting switch 960 will then open the leads of the DC motor 920, allowing the rotatable shaft to rotate more freely and the movable pole segment 911 to continue to fall. This will repeat until the pole 904 comes slowly to rest in the fully retracted position.

At least one relay 966 is electrically connected to the electrical portion of the DC motor 920, the motor control circuit 932, and the slowdown circuit 958. In the preferred embodiment, a pair of relays 966 is utilized, but those skilled in the art realize other implementations, including a single relay 966 with multiple sets of contacts. The relays 966 electrically connect the electrical portion of the DC motor 920 to the motor control circuit 932 when the motor power is available and electrically connect the electrical portion to the slowdown circuit 958 when the motor power is unavailable. Thus, the motor control circuit 932 and the slowdown circuit 958 are electrically isolated from one another.

X. Docking

Figure 49:
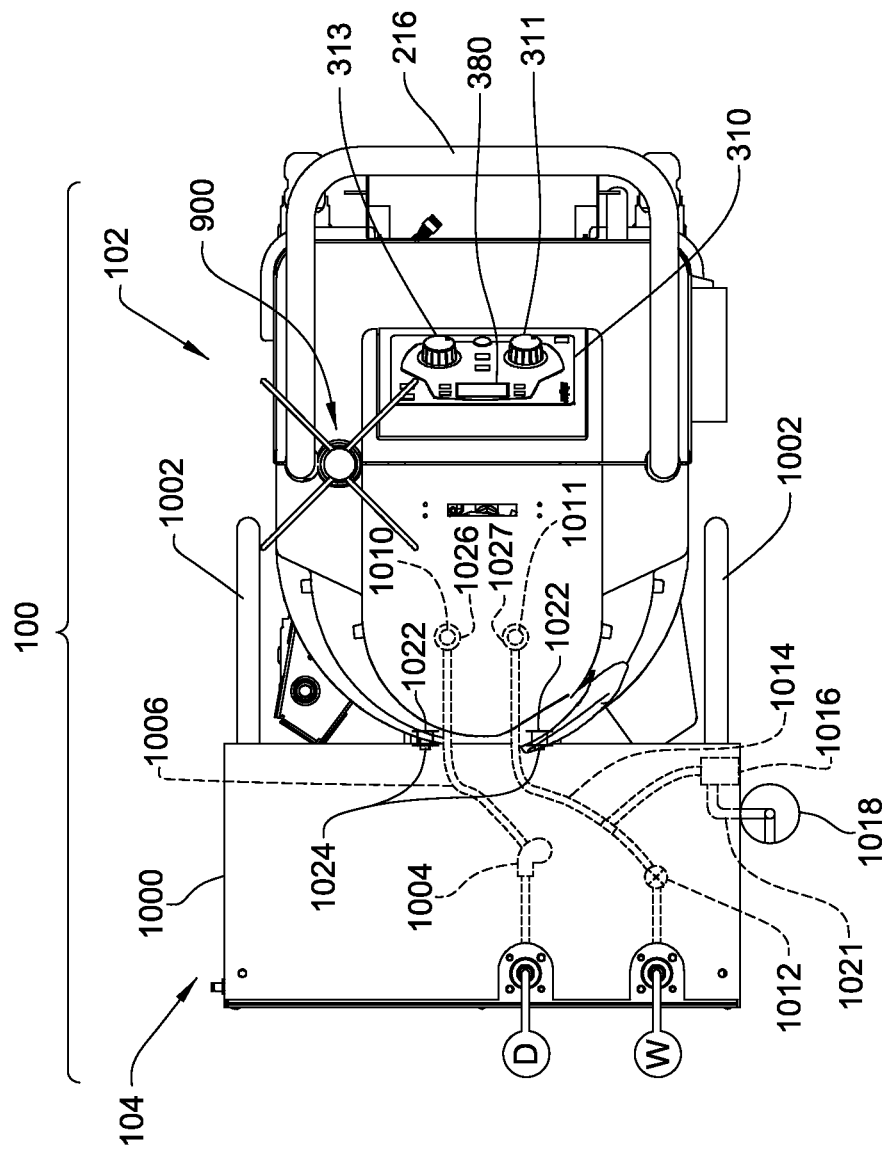
FIG. 49 is a top view of the waste collection unit docked to the docking station.
Figure 50:
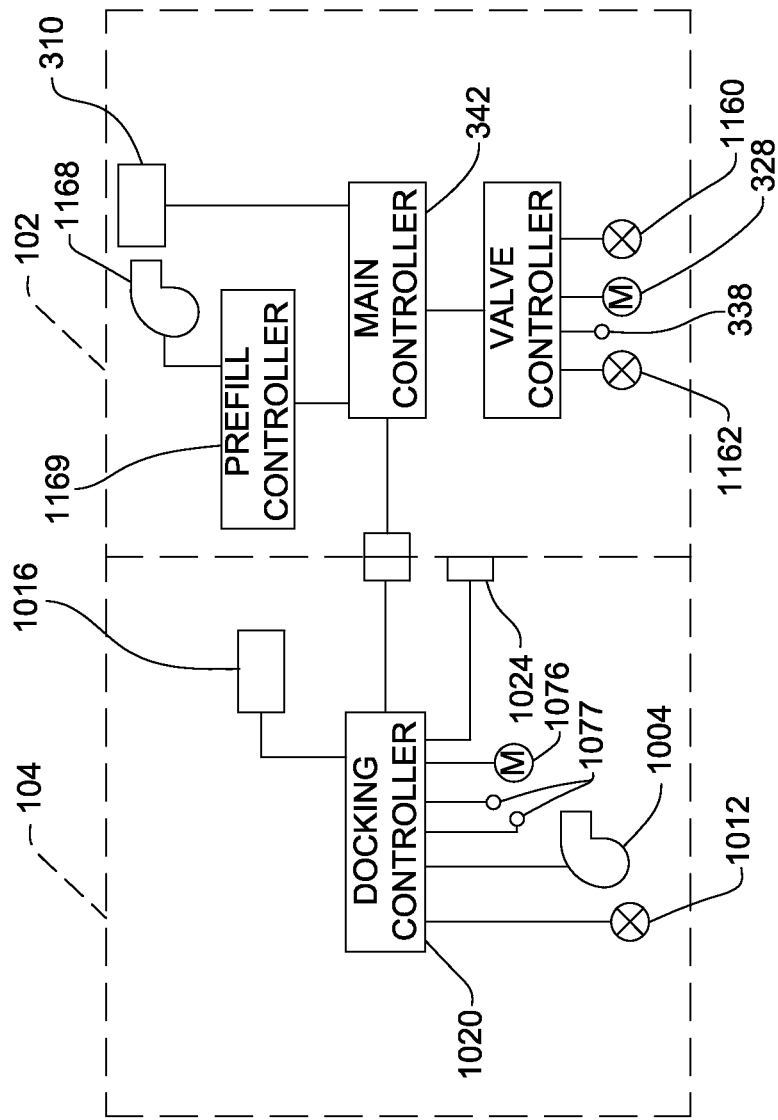
FIG. 50 is an electrical block diagram of the docking station and the waste collection unit.

Referring to FIGS. 1, 49, and 50, the docking station 104 includes a metal cabinet 1000 generally in the shape of a box having a front opening 1001 (see FIG. 1). Guide rails 1002 extend from a front of the cabinet 1000 to guide the waste collection unit 102 when docking to the docking station 104. An off-load pump 1004 is disposed inside the cabinet 1000. The off-load pump 1004 is connected to the waste drain D to pump the waste material from the waste collection unit 102 to the waste drain D when the waste collection unit 102 is docked to the docking station 104. A drain line 1006 extends from the off-load pump 1004 to a waste coupling 1010. The off-load pump 1004 may be a Jabsco® AC water pump, Part No. 18660-0133, manufactured by ITT Industries of White Plains, N.Y.

A water valve 1012 is also disposed inside the cabinet 1000. The water valve 1012 is connected to a water source W in the health care facility. The water valve 1012 may be connected to a hot water source, a cold water source, or any combination thereof. A water line 1014 extends from the water valve 1012 to a water coupling 1011. An injector 1016 is coupled to the water line 1014 to inject cleaner into the water line 1014. A container 1018 of cleaner may be disposed outside of the cabinet 1000 with an intake line 1021 of the injector 1016 feeding into the container 1018 such that as the container 1018 is depleted, a new container of cleaner can replace it by simply moving the intake line 1021 to the new container. The water valve 1012 and injector 1016 are used to convey water, with or without cleaner, into a cleaning system of the waste collection unit 102 when the waste collection unit 102 is docked to the docking station 104.

Referring back to FIG. 1, the docking station has a pair of docking receivers 1024 disposed on the front of the docking station. The waste collection unit 102 has a corresponding pair of metal strike plates 1022. The docking receivers 1024 are configured to receive the strike plates 1022 to mate the waste collection unit 102 with the docking station 104 during docking. It should be appreciated that the strike plates 1022 and the docking receivers 1024 could be reversed. In the disclosed embodiment, the docking receivers 1024 are electromagnetically operated to magnetically adhere to the strike plates 1022 under certain conditions.

Referring to FIG. 50, a docking controller 1020 operates the docking station 104 in accordance with instructions from the main controller 342 when the waste collection unit 102 successfully docks with the docking station 104. The off-load pump 1004, water valve 1012, and injector 1016 are all in communication with the docking controller 1020 and controlled by the docking controller 1020 through instructions from the main controller 342.

When the waste collection unit 102 is ready to be emptied, the waste collection unit 102 is wheeled to the docking station 104 to mate with the docking station 104, as shown in FIG. 49.

To mate together, the guide rails 1002 on the docking station 104 guide the waste collection unit 102 until the strike plates 1022 engage the docking receivers 1024. To facilitate dumping and cleaning of the waste collection unit 102, the waste 1010 and water 1011 couplings of the docking station 104 mate with a second set of waste 1026 and water 1027 couplings on board the waste collection unit 102 (see also FIG. 64B). The first set of couplings 1010, 1011 of the docking station 104 shall hereinafter be referred to as docker couplings 1010, 1011 and the second set of couplings 1026, 1027 shall hereinafter be referred to as rover couplings. When the couplings 1010, 1011, 1026, 1027 mate, fluid communication is opened between the waste collection unit 102 and the docking station 104.

Referring to FIGS. 1 and 51 through 57, a head 1030 is mounted to the cabinet 1000 for interfacing with the waste collection unit 102 to facilitate mating of the docker couplings 1010, 1011 to the rover couplings 1026, 1027. In the preferred embodiment, one of the docker couplings 1010 mates with one of the rover couplings 1026 to convey the waste material stored on the waste collection unit 102 to the waste drain D via the offload pump 1004 and another of the docker couplings 1011 mates with another of the rover couplings 1027 to convey water and cleaner to the waste containers 200, 202 of the waste collection unit 102 to clean the waste containers 200, 202.

Figure 51:
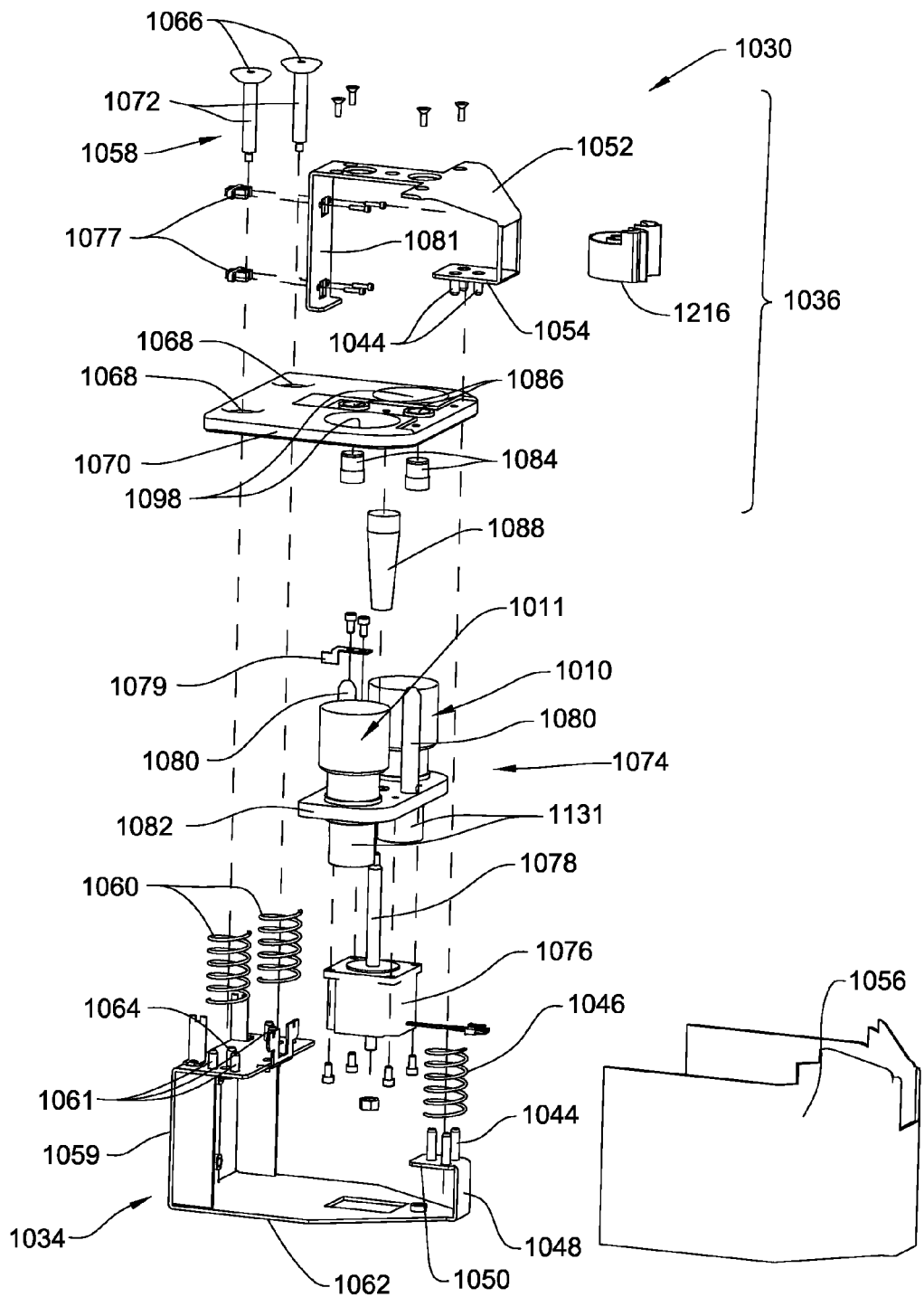
FIG. 51 is an exploded perspective view of a head of the docking station.

Referring to FIG. 51, the head 1030 comprises a base frame 1034 mounted to the cabinet 1000 for supporting the head 1030. The base frame 1034 is relatively sturdy and is fixed to the cabinet 1000 such that the base frame 1034 moves very little during use. Conversely, a floating frame 1036 is coupled to the base frame 1034 by spring-loaded supports 1038, 1040, 1042 (see FIGS. 54 and 55). These spring-loaded supports 1038, 1040, 1042 provides six degrees of freedom for the floating frame 1036 relative to the base frame 1034 to increase the ability of the head 1030 to mate the docker couplings 1010, 1011 with the rover couplings 1026, 1027. The base frame 1034 and floating frame 1036 are preferably formed of metallic materials such as stainless steel, brass, and the like.

Referring to FIGS. 51 and 55, a front spring-loaded support 1038 includes a plurality of front support posts 1044 and a front spring 1046. The base frame 1034 includes a front 1048 with a first bent flange 1050. The floating frame 1036 includes a front bracket 1052 having a complementary second bent flange 1054. The front support posts 1044 extend from the first bent flange 1050 and the second bent flange 1054. The front spring 1046 is centered over the front support posts 1044 and biases the second bent flange 1054 away from the first bent flange 1050. As a result, a front of the floating frame 1036 can tilt down against the bias of the front spring 1046 to facilitate mating with the waste collection unit 102. A skirt 1056 mounts to the front bracket 1052 to conceal an interior of the head 1030 and protect its interior components.

Referring to FIGS. 51 and 54, a pair of rear spring-loaded supports 1040, 1042 is also provided. Each of the rear spring-loaded supports 1040, 1042 includes a rear support member 1058, a plurality of rear support posts 1061, and a rear spring 1060. The base frame 1034 includes a rear 1059, a bottom 1062 extending from the front 1048 to the rear 1059, and a top 1064 extending from the rear 1059 toward the front 1048. Each of the rear support members 1058 include a tapered head 1066 that rest in correspondingly shaped tapered bores 1068 defined in a top plate 1070 of the floating frame 1036. Each of the rear support members 1058 also include shafts 1072 that extend from the tapered heads 1066 down through the top plate 1070 to the top 1064 of the base frame 1034. The shafts 1072 are fixed to the top 1064 of the base frame 1034. The rear springs 1060 surround the shafts 1072 and the rear support posts 1061 to bias the top plate 1070 of the floating frame 1036 away from the top 1064 of the base frame 1034. In a rest position, the tapered heads 1066 rest in the tapered bores 1068. When the waste collection unit 102 is mating with the docking station 104, the top plate 1070 may be pressed downwardly, in which case, the tapered bores 1068 will move down and away from the tapered heads 1066 against the bias of the rear springs 1060.

Figure 56:
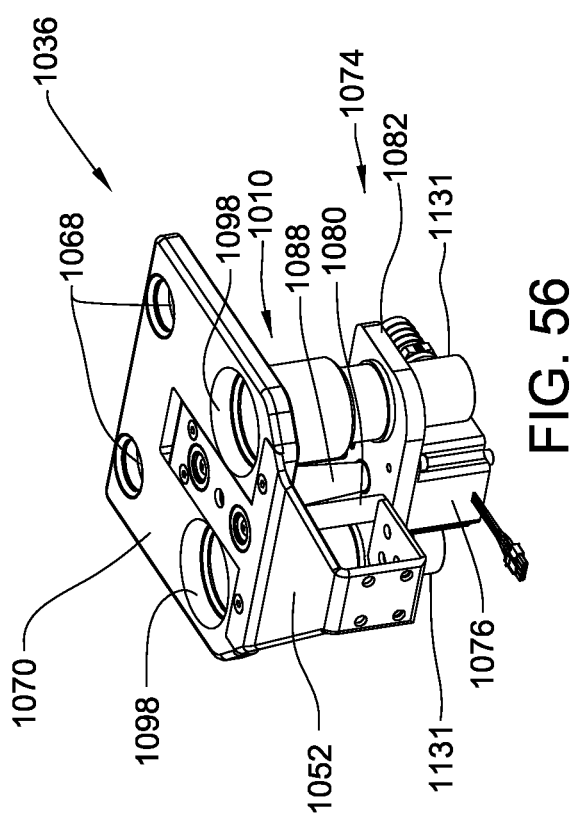
FIG. 56 is a front perspective view of a floating frame and mating interface of the head.
Figure 57:
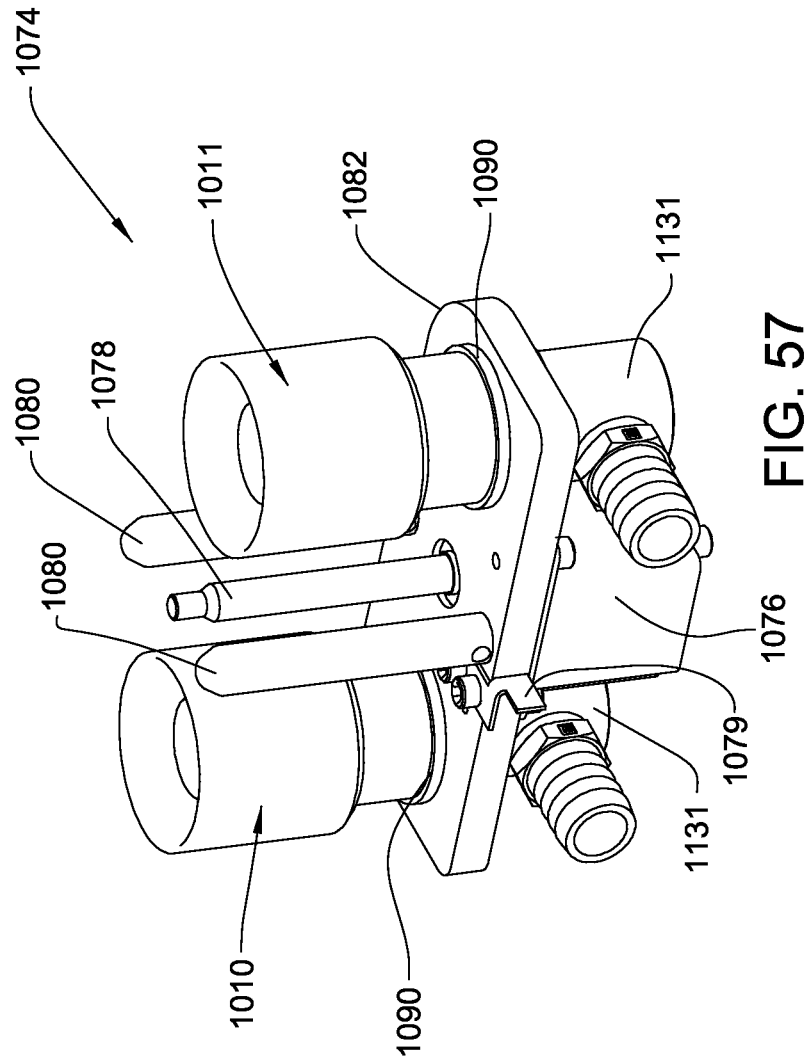
FIG. 57 is a rear perspective view of the mating interface.

Referring specifically to FIGS. 55 through 57, a mating interface 1074 is shown. The mating interface 1074 includes the docker couplings 1010, 1011. A coupling actuator, preferably a stepper motor 1076 with lead screw 1078 is operatively coupled to the docker couplings 1010, 1011 by a coupling plate 1082 to raise the docker couplings 1010, 1011 and mate the docker couplings 1010, 1011 with the rover couplings 1026, 1027. The docker couplings 1010, 1011 are seated in openings in the coupling plate 1082 and are held there between spacers 1090 (see FIG. 57) by retaining rings (not numbered). The coupling plate 1082 is preferably formed of a metallic material.

The stepper motor 1076 is electronically controlled by the docking controller 1020 through the main controller 342 and is used to raise and lower the coupling plate 1082. One end of the lead screw 1078 is rotatably mounted in the top plate 1070 such that the lead screw 1078 rotates relative to the top plate 1070 without moving up or down relative to the top plate 1070. The lead screw 1078 of the stepper motor 1076 threadably engages the coupling plate 1082 to raise and lower the coupling plate 1082 relative to the floating frame 1036. Guide rods 1080 are fixed to the coupling plate 1082 via threaded connections. Guide bushings 1084 are press fit into a pair of openings 1086 (see FIG. 51) in the top plate 1070 to slidably receive the guide rods 1080. As a result, when the lead screw 1078 rotates, the coupling plate 1082 rises. A sheath 1088 surrounds and protects the lead screw 1078. When the stepper motor 1076 raises the coupling plate 1082, the docker couplings 1010, 1011 also rise through a pair of openings 1098 in the top plate 1070 to insert into and mate with the rover couplings 1026, 1027. The stepper motor 1076 may be manufactured by Haydon Switch and Instrument, manufacturer part no. 57F4A-3.25-048.

Referring specifically to FIG. 51, a sensor assembly is used to monitor a position of the docker couplings 1010, 1011 to assist in interconnecting the couplings 1010, 1011, 1026, 1027 and to notify the main controller 342 when the couplings 1010, 1011, 1026, 1027 have successfully mated. The sensor assembly includes a pair of Hall-effect sensors 1077 fixed to a back leg 1081 of the front bracket 1052. Each Hall-effect sensor 1077 includes both a sensing element formed as a semiconductor component and a magnet spaced from the sensing element (semiconductor component and magnets not illustrated.) The sensor assembly also includes a corresponding tab 1079 formed from ferrous material fixed to the coupling plate 1082. The Hall-effect sensors 1077 are in electronic communication with the docking controller 1020. As the coupling plate 1082 and tab 1079 move towards/away from a particular Hall-effect sensor 1077, the tab 1079 changes the characteristics of the magnet field the magnet produces around the sensing element. The change in magnet field strength cause the Hall-effect sensor sensing element to output a variable position signal. These position signals are sent to the docking controller 1020. The docking controller 1020 determines whether or not the docker couplings 1010, 1011 have successfully mated to the rover couplings 1026, 1027 based on the characteristics of the received position signals. When they successfully mate, the docking controller 1020 operates the off-load pump 1004 to begin off-loading the waste material collected in the waste collection unit 102.

Figure 58:
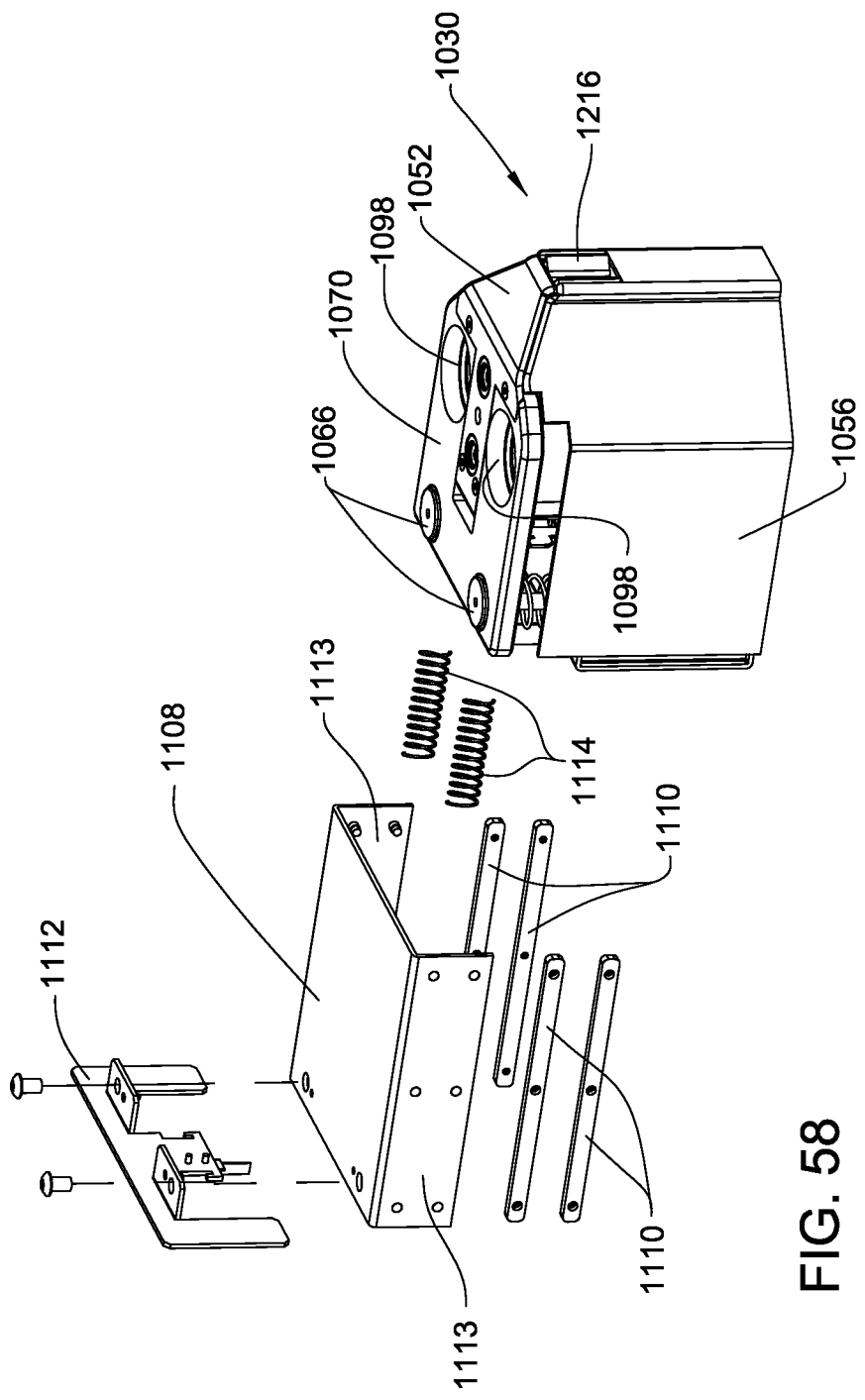
FIG. 58 is an exploded perspective view of a sliding cover plate to cover the head of the docking station when not engaged by the waste collection unit.
Figure 59:
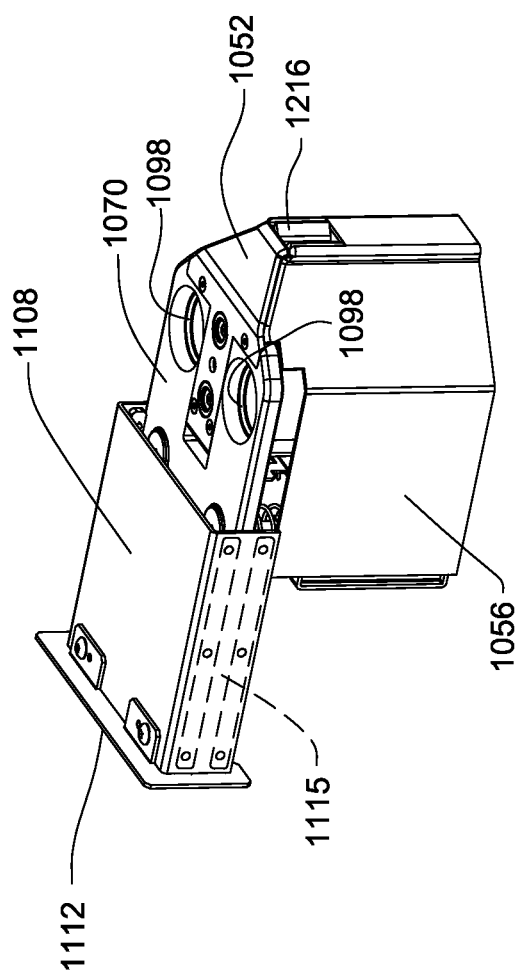
FIG. 59 is a perspective view of the sliding cover plate in a retracted position.

Referring to FIGS. 58 and 59, a sliding cover plate 1108 covers the head 1030 when the waste collection unit 102 is not docked to the docking station 104. A rear bracket 1112 is disposed inside the cabinet 1000. The rear bracket 1112 has a periphery greater than that of the front opening 1001 such that the rear bracket 1112 is restrained from popping out of the cabinet 1000 through the front opening 1001. Yet, the rear bracket 1112 can move rearwardly inside the cabinet 1000. A rear end of the cover plate 1108 is fixed to the rear bracket 1112. A plurality of rails 1110 are fixed to sides 1113 of the cover plate 1108. A pair of the rails 1110 is aligned longitudinally with the cover plate 1108 on each of the sides 1113. Each pair of the rails 1110 are spaced apart on the sides 1113 to define a track 1115 (see FIG. 59) on each side 1113 for receiving an outer hanging edge of the top plate 1070. As a result, the cover plate 1108 can slide along the outer hanging edges between open and closed positions. A pair of springs 1114 extend between the rear bracket 1112 and the base frame 1034 to bias the cover plate 1108 into the closed position, covering the head 1030. The cover plate 1108 is shown in the open position in FIG. 59.

Figure 61:
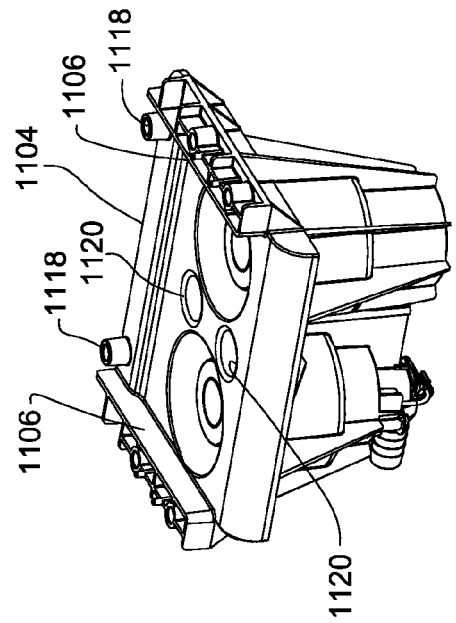
FIG. 61 is a bottom perspective view of the carrier.
Figure 60:
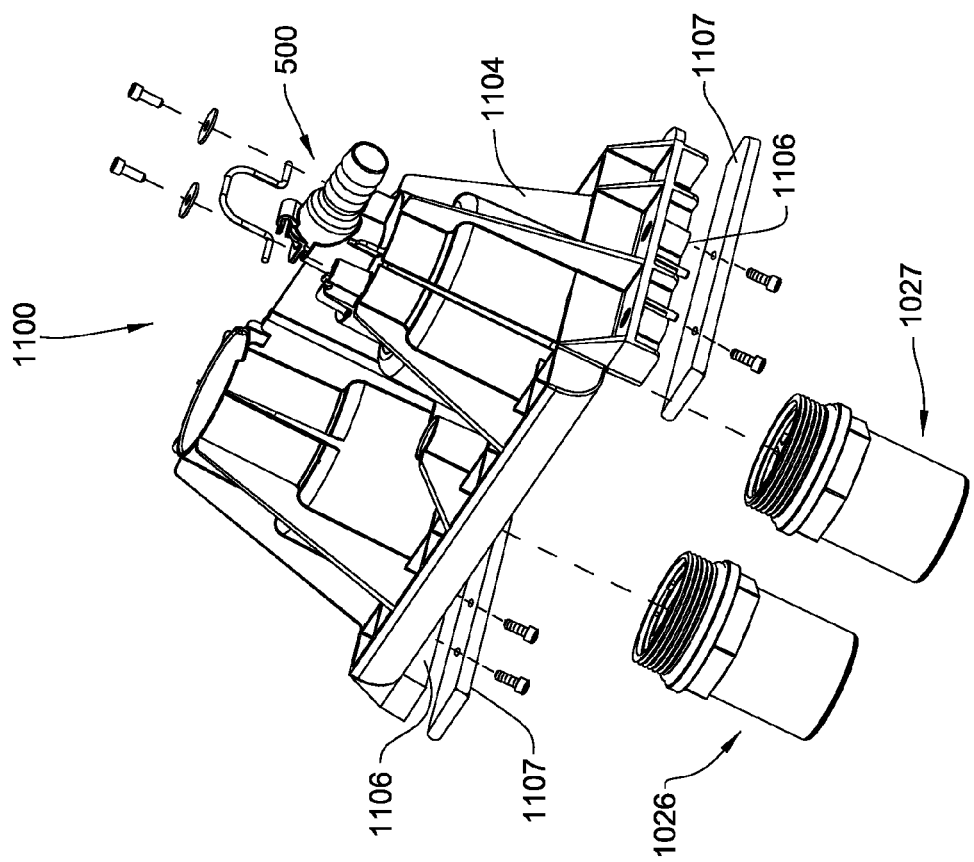
FIG. 60 is an exploded perspective view of a carrier and associated rover couplings.
Figure 62:
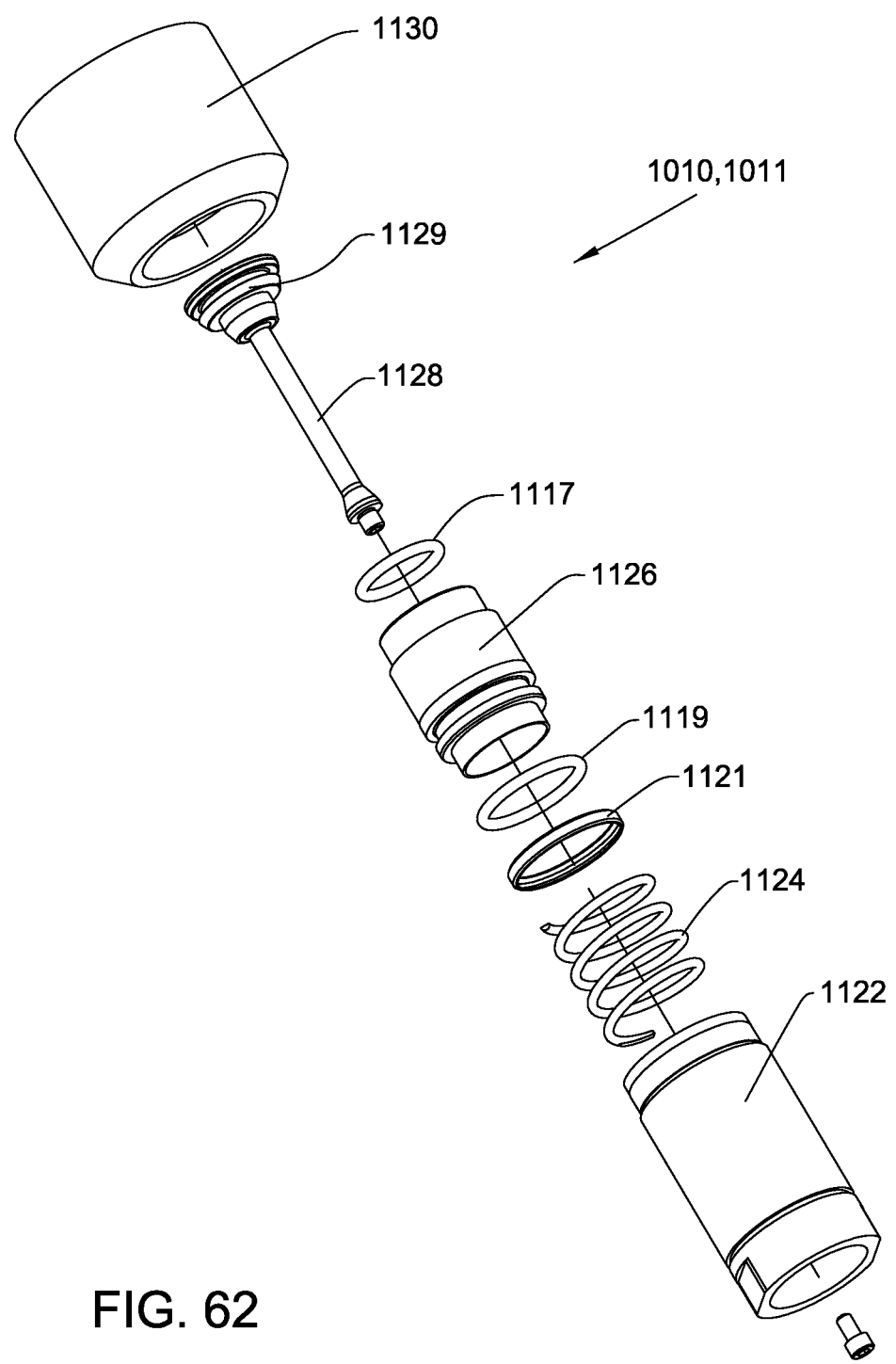
FIG. 62 is an exploded perspective view of a docker coupling.
Figure 63:
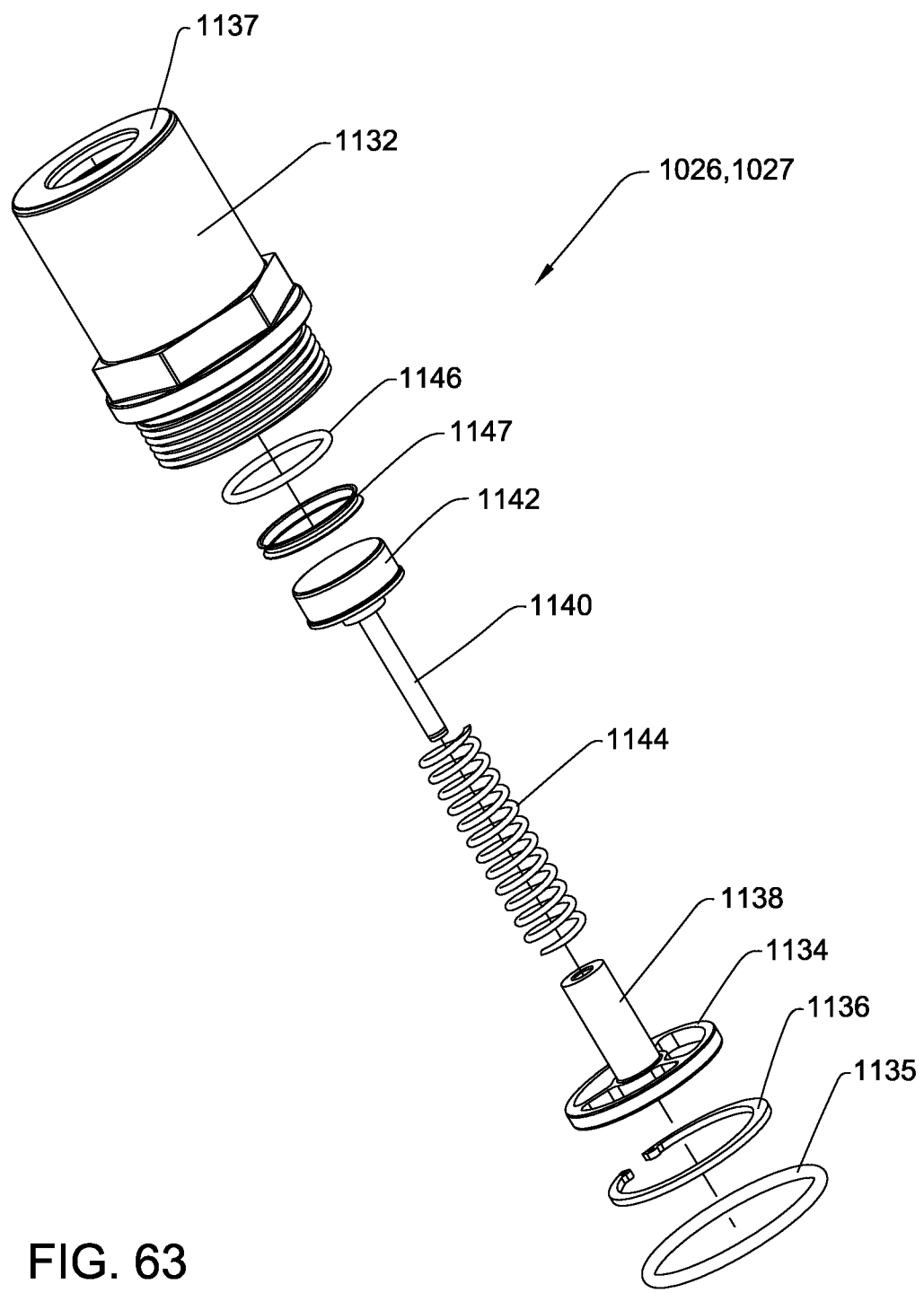
FIG. 63 is an exploded perspective view of a rover coupling.

Referring to FIGS. 2, 60, and 61, a carrier 1100 supports the rover couplings 1026, 1027 on the waste collection unit 102. The carrier 1100 is mounted to a top of the cart base 206 of the waste collection unit 102. A drain neck 1102 (see FIGS. 38 and 64A), integrally formed with the bottom 232 of the lower canister 224 extends from the bottom 232 of the lower canister 224 into the carrier 1100 and the other of the rover couplings 1027 extends to an on-board cleaning system described further below.

When the carrier 1100 of the waste collection unit 102 interfaces with the floating frame 1036 of the head 1030 of the docking station 104, the couplings 1010, 1011, 1026, 1027 become aligned to facilitate connection to one another, e.g., the waste couplings 1010, 1026 align with one another and the water couplings 1011, 1027 align with one another, such that the docking station 104 can drain the waste material from the waste containers 200, 202, and the docking station 104 can inject cleaner into the waste containers 200, 202 and rinse the waste containers 200, 202.

The carrier 1100 includes a block 1104 with guides, in the form of reinforced guide walls 1106, extending downwardly from the block 1104. The guide walls 1106 on the carrier 1100 act against the cover plate 1108 to slide the cover plate 1108 to expose the head 1030 and the pair of openings 1098 from which the docker couplings 1010, 1011 rise. A pair of stops 1118 protrudes from the block 1104 to engage the floating frame 1036 and prevent over-alignment of the couplings 1010, 1011, 1026, 1027. A pair of guide rails 1107 is attached to an underside of the block 1104. When rover 102 is positioned adjacent docker 104 so the cart base 206 is disposed over docker head 1030, the rover guide rails 1107 slide under the outer hanging edges of the top plate 1070 of the floating frame 1036 to further assist in vertically and horizontally aligning the docker couplings 1010, 1011 to the rover couplings 1026, 1027 (see FIG. 64A). The guide rails 1107 are removed in FIG. 61.

Figure 64A:
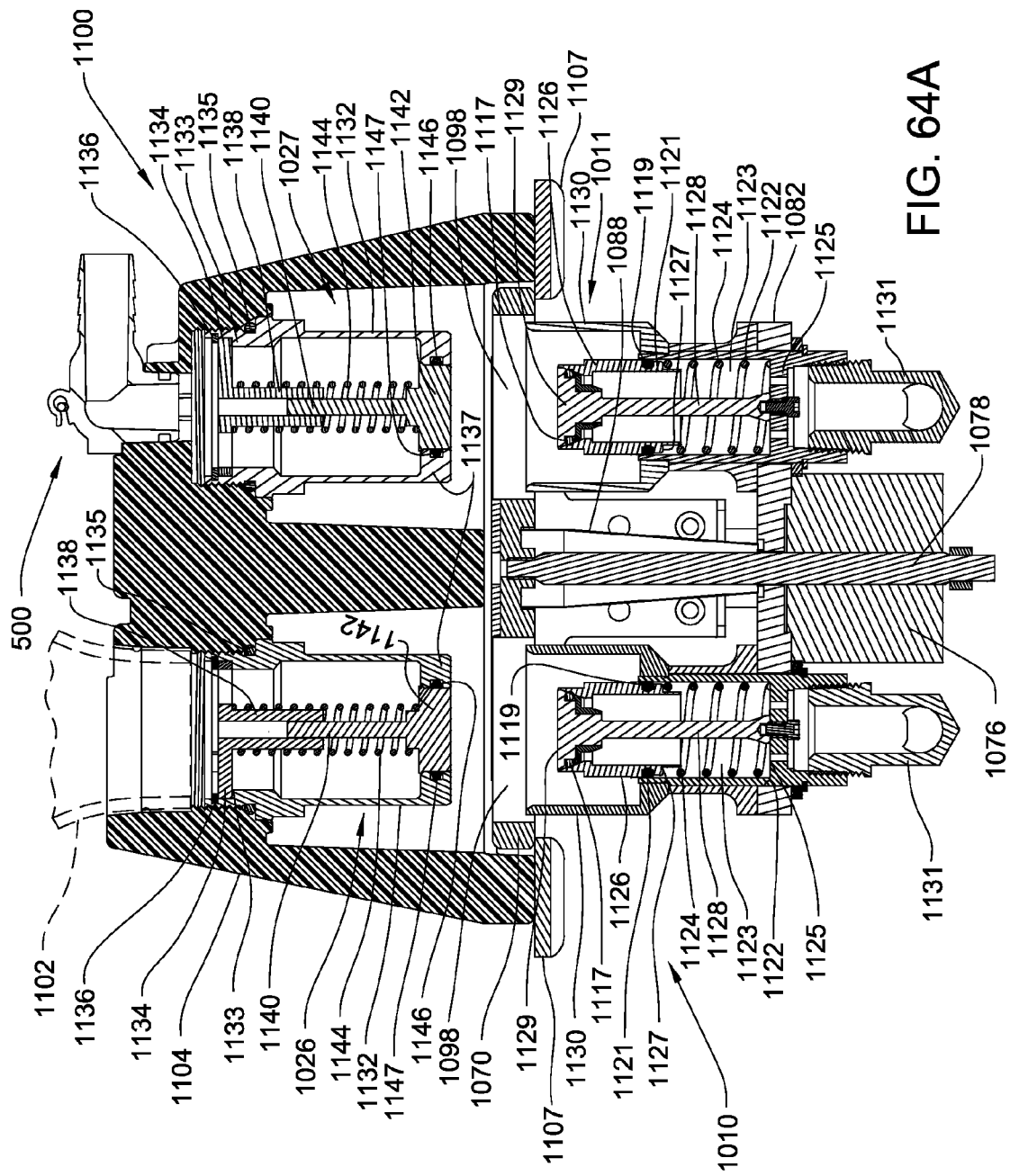
FIG. 64A is a cross-sectional view of the head of the docking station and carrier of the waste collection unit showing the docker and rover couplings prior to engagement.
Figure 64B:
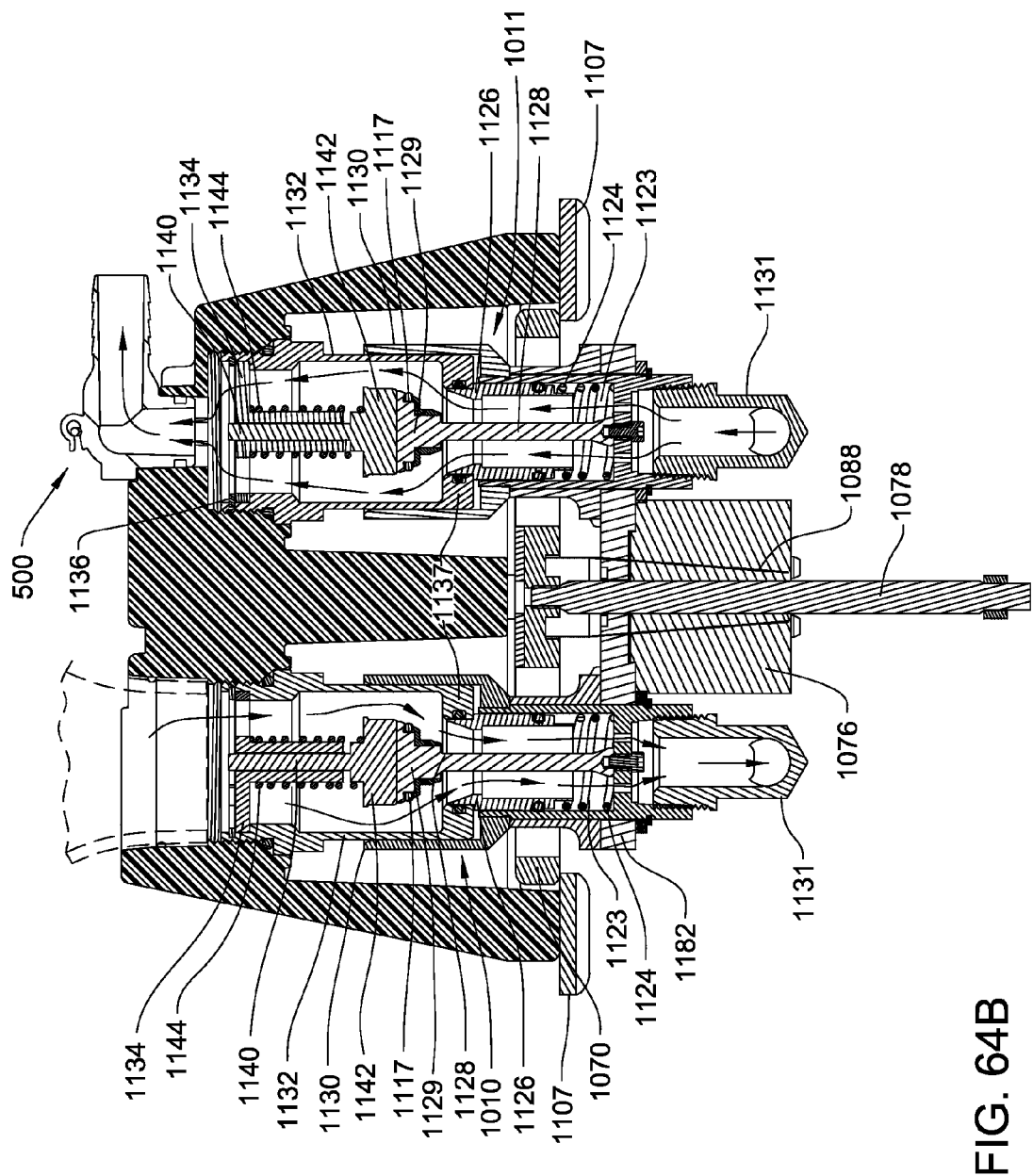
FIG. 64B is a cross-sectional view of the head of the docking station and carrier of the waste collection unit showing the docker and rover couplings engaged to permit fluid communication therebetween.

The couplings 1010, 1011, 1026, 1027 are best shown in FIGS. 62, 63, 64A, and 64B. Each of the docker couplings 1010, 1011 includes a coupling housing 1122 defining a spring chamber 1123 (see FIG. 64A). A spring 1124 is disposed in the spring chamber 1123. A coupling sleeve 1126 is slidably disposed in the spring chamber 1123. The spring 1124 extends between a center wall 1125 (see FIG. 64A) of the coupling housing 1122 and the coupling sleeve 1126. An o-ring 1119 and shaft seal 1121 (formed of PTFE in one embodiment) are disposed in the spring chamber 1123 about an outer groove of the coupling sleeve 1126 to slidably seal the coupling sleeve 1126 in the spring chamber 1123. The coupling sleeve 1126 has a first open end with a shoulder 1127 (see FIG. 64A) for receiving the spring 1124 and a second open end with a frusto-conical shape. A plunger 1128 is fixed to the center wall 1125 and includes a head 1129 having a frusto-conical shape matching that of the second open end of the coupling sleeve 1126. An o-ring 1117 fits in an annular groove defined about the head 1129 to seal the head 1129 to the coupling sleeve 1126. The head 1129 holds the coupling sleeve 1126 against the bias of the spring 1124. A sheath 1130 is fixed to the coupling housing 1122 to protect the coupling sleeve 1126. As shown in FIGS. 64A and 64B, connectors 1131 connect the docker couplings 1010, 1011 to their respective drain 1006 and water 1014 lines. The coupling housing 1122, coupling sleeve 1126, plunger 1128, and sheath 1130 may be formed of metal, and in one embodiment, stainless steel.

Each of the rover couplings 1026, 1027 includes a rover coupling housing 1132 that threads into threaded openings in the block 1104 of the carrier 1100. An o-ring 1135 seals the rover coupling housing 1132 in the threaded openings. The rover coupling housing 1132 has a first open end with an inner annular shoulder 1133 (see FIGS. 64A and 64B) and a second end 1137. A plunger base 1134 is retained against the inner annular shoulder 1133 by a retainer ring 1136. The retainer ring 1136 seats in an inner annular groove defined in the rover coupling housing 1132. The plunger base 1134 includes a sleeve portion 1138 extending toward the second end 1137. A piston 1140 slides in the sleeve portion 1138 between a closed position in which the second end 1137 is closed and an open position in which the second end 1137 is open to allow fluid to flow therethrough. Thus, the piston 1140 acts as a coupling valve. More specifically, the piston 1140 includes a head 1142 that fits into an opening in the second end 1137 to close the second end 1137 in the closed position. In the open position, the head 1142 is moved out from the opening. A spring 1144 biases the head 1142 of the piston 1140 into the opening in the second end 1137. An o-ring 1146 and piston seal 1147 (formed of PTFE in one embodiment) are disposed in a groove at the second end 1137 of the rover coupling housing 1132 about the opening to seal the head 1142 when in the opening. The rover coupling housing 1132, plunger base 1134, and piston 1140 may be formed of metal, and in one embodiment, stainless steel.

Referring to FIGS. 64A and 64B, the waste collection unit 102 is shown docked to the docking station 104. When this occurs, the docker 1010, 1011 and rover 1026, 1027 couplings mate and provide fluid communication between the docking station 104 and the waste collection unit 102. In FIG. 64A, the docker couplings 1010, 1011 are shown at their lowermost position prior to moving to engage the rover couplings 1026, 1027. When the waste collection unit 102 docks to the docking station 104, i.e., when the strike plates 1022 mate with the docking receivers 1024, the rover couplings 1026, 1027 are then engaged by the docker couplings 1010, 1011. More specifically, the docker couplings 1010, 1011 are automatically moved by the stepper motor 1076 to mate with the rover couplings 1026, 1027. The guide rods 1080 slide into a corresponding pair of bores 1120 (see FIG. 61) in the block 1104 to assist in aligning the couplings 1010, 1011, 1026, 1027 to facilitate a successful fluid connection between the waste collection unit 102 and the docking station 104. The electromagnets of the docking receivers 1024 are energized by the docking controller 1020 to hold their connection to the strike plates 1022 until at least the docker couplings 1010, 1011 are fully engaged to the rover couplings 1026, 1027. Thereafter, they may be de-energized until the connection is to be terminated at which point they will be reenergized until the docker couplings 1010, 1011 are fully retracted to their initial position.

In FIG. 64B, the docker couplings 1010, 1011 are shown successfully mated to the rover couplings 1026, 1027. Here, the second end of the coupling sleeve 1126 with the head 1129 of the plunger 1128 slides into the opening in the second end 1137 of the rover coupling housing 1132. As the stepper motor 1076 continues to raise the docker couplings 1010, 1011, the head 1129 of the plunger 1128 continues to press against the head 1142 of the piston 1140 thereby compressing the spring 1144. This opens the second end 1137 of the rover coupling housing 1132 and the second end of the coupling sleeve 1126 thereby opening fluid communication between the lower waste container 202 and the drain line 1006 and between the cleaning system of the waste collection unit 102 and the water line 1014. The flow of waste material (e.g., collected waste material, rinse water, spent water with cleaner, etc.) and water (with or without cleaner) is shown in FIG. 64B.

XI. Cleaning System of Waste Collection Unit

Figure 65:
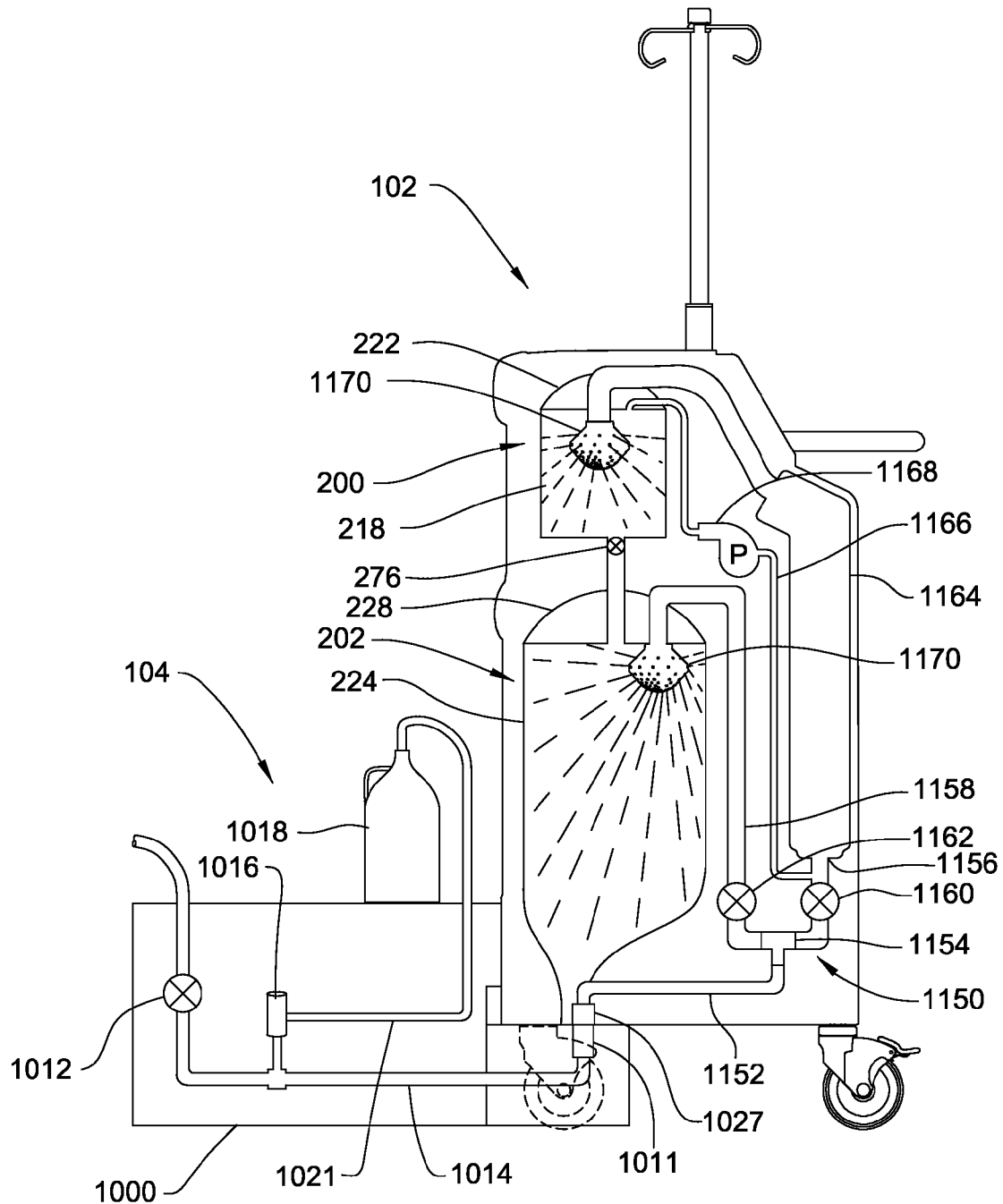
FIG. 65 is a schematic view of a cleaning system of the waste collection unit and the docking station.

Referring to FIG. 65, the cleaning system supported by the waste collection unit 102 for cleaning the waste collection unit 102 is shown. The cleaning system includes a cleaning circuit 1150 of water lines and associated flow components supported on the waste collection unit 102, as described below.

The cleaning circuit 1150 comprises a supply line 1152 that extends from the water coupling 1027 on the waste collection unit 102 to a tee 1154. From the tee 1154, the supply line 1152 is split into an upper supply line 1156 and a lower supply line 1158. The lower supply line 1158 includes an electronically operated lower solenoid valve 1162. The lower solenoid valve 1162 controls the flow of liquid into the lower waste container 202. The upper supply line 1156 includes a matching electronically operated upper solenoid valve 1160 to control the flow of liquid into the upper waste container 200.

The upper supply line 1156 opens into an on-board reservoir 1164 for storing water to provide the prefill discussed above with respect to the fluid measuring system. The upper supply line 1156 continues to the upper cap 222 of the upper waste container 200. A secondary supply line 1166 splits flow from the upper supply line 1156, just below the on-board reservoir 1164. A first end of the secondary supply line 1166 is located below the on-board reservoir 1164 with respect to gravity to be able to drain the on-board reservoir 1164 during use. A second end of the secondary supply line 1166 empties into the upper waste container 200. A prefill pump 1168 conveys the stored water from the on-board reservoir 1164 through the secondary supply line 1166 into the upper waste container 200 during use to provide the desired tare volume of liquid in the upper canister 218. The prefill pump 1168 automatically pumps a predetermined amount of liquid into the upper canister 218 after each time the upper waste container 200 is dumped into the lower waste container 202 and after each cleaning. The prefill pump 1168 is controlled by a prefill controller 1169 in communication with the main controller 342.

Figure 66:
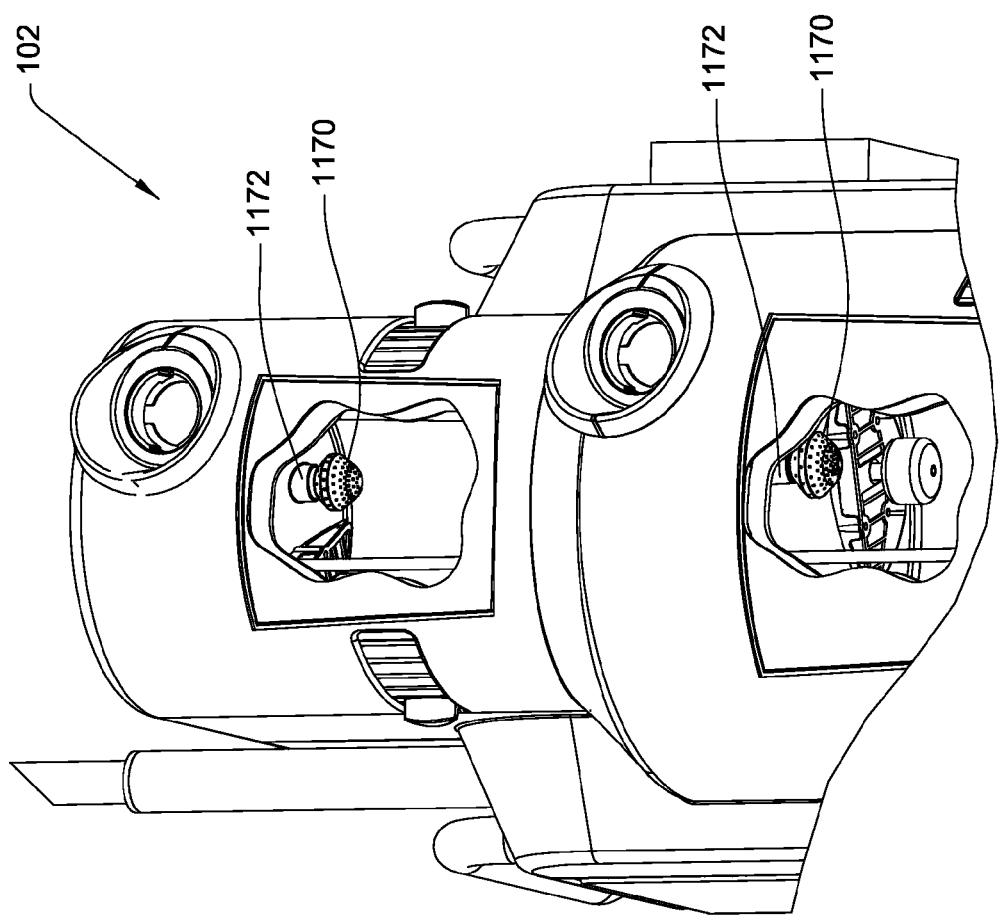
FIG. 66 is a cut-away view of the waste collection unit showing sprinklers disposed in the upper and lower waste containers.
Figure 67:
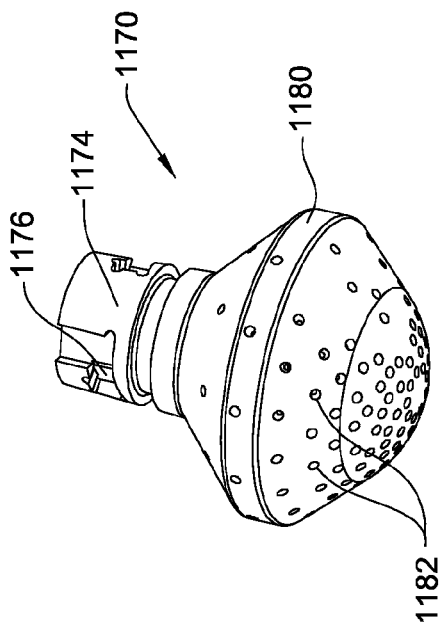
FIG. 67 is a bottom perspective view of the sprinkler.
Figure 68:
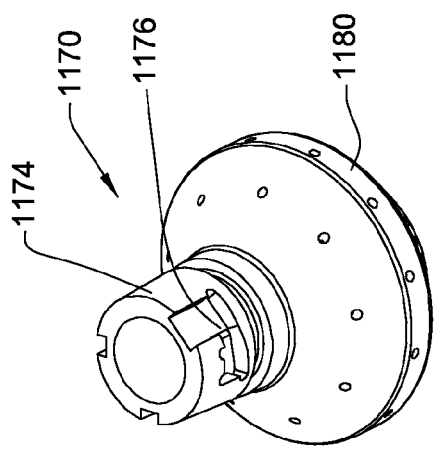
FIG. 68 is a top perspective view of the sprinkler.

Referring to FIGS. 65 and 66, sprinklers 1170 are provided in each canister 218, 224 to clean the canisters 218, 224 upon docking the waste collection unit 102 to the docking station 104. The sprinklers 1170 are described further below. The sprinklers 1170 are mounted in sprinkler ports 1172 (see also FIGS. 31 and 32) in the caps 222, 228 of the waste containers 200, 202. The distal end of the upper supply line 1156 is mounted to the upper cap 222 in fluid communication with the sprinkler 1170 located in the upper canister 218. The distal end of the lower supply line 1158 is mounted to the lower cap 228 in fluid communication with the sprinkler 1170 located in the lower canister 224. These distal ends are outfitted with the elbow connectors 500 previously described to fit in associated receptacles 670 in the caps 222, 228 that are in communication with the sprinkler ports 1172 and the sprinklers 1170.

Referring to FIGS. 67 through 72, the sprinklers 1170 are shown in more detail. It should be appreciated that the sprinklers 1170 located in the upper 218 and lower 224 canisters are identical. Each sprinkler 1170 includes a mounting neck 1174 with L-shaped slots 1176. The L-shaped slots 1176 slide over corresponding projections 1178 in the sprinkler port 1172 when the sprinkler 1172 is inserted therein. The sprinkler 1170 is then rotated to lock into place. A sprinkler head 1180 is positioned on the mounting neck 1174. In the preferred embodiment, the sprinkler head 1180 is integral with the mounting neck 1174. The sprinklers 1170 are fixed to the caps 222, 228 and stationary relative to the caps 222, 228. Furthermore, the sprinklers 1170 do not include any moving parts necessary for their operation.

Figure 72:
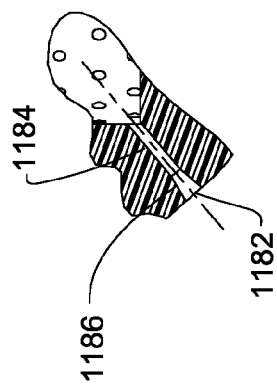
FIG. 72 is a close-up view of an injection port of the sprinkler from FIG. 71.
Figure 71:
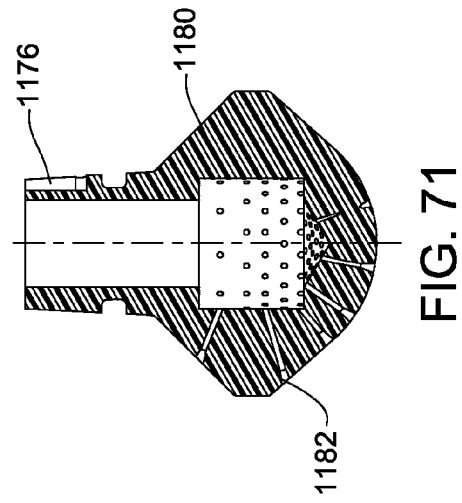
FIG. 71 is a cross-sectional view of the sprinkler.
Figure 70:
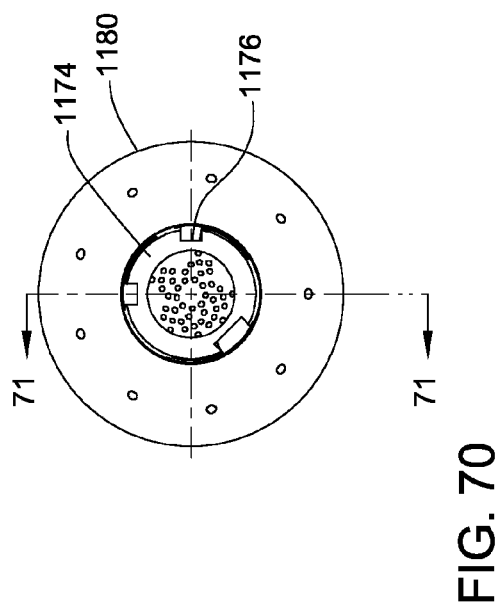
FIG. 70 is a top view of the sprinkler.
Figure 69:
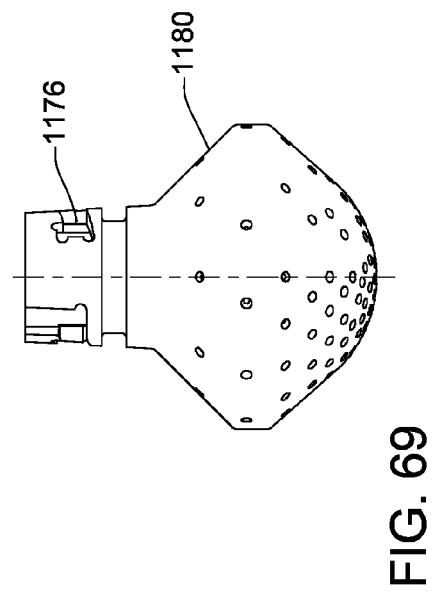
FIG. 69 is a side elevational view of the sprinkler.
Figure 73:
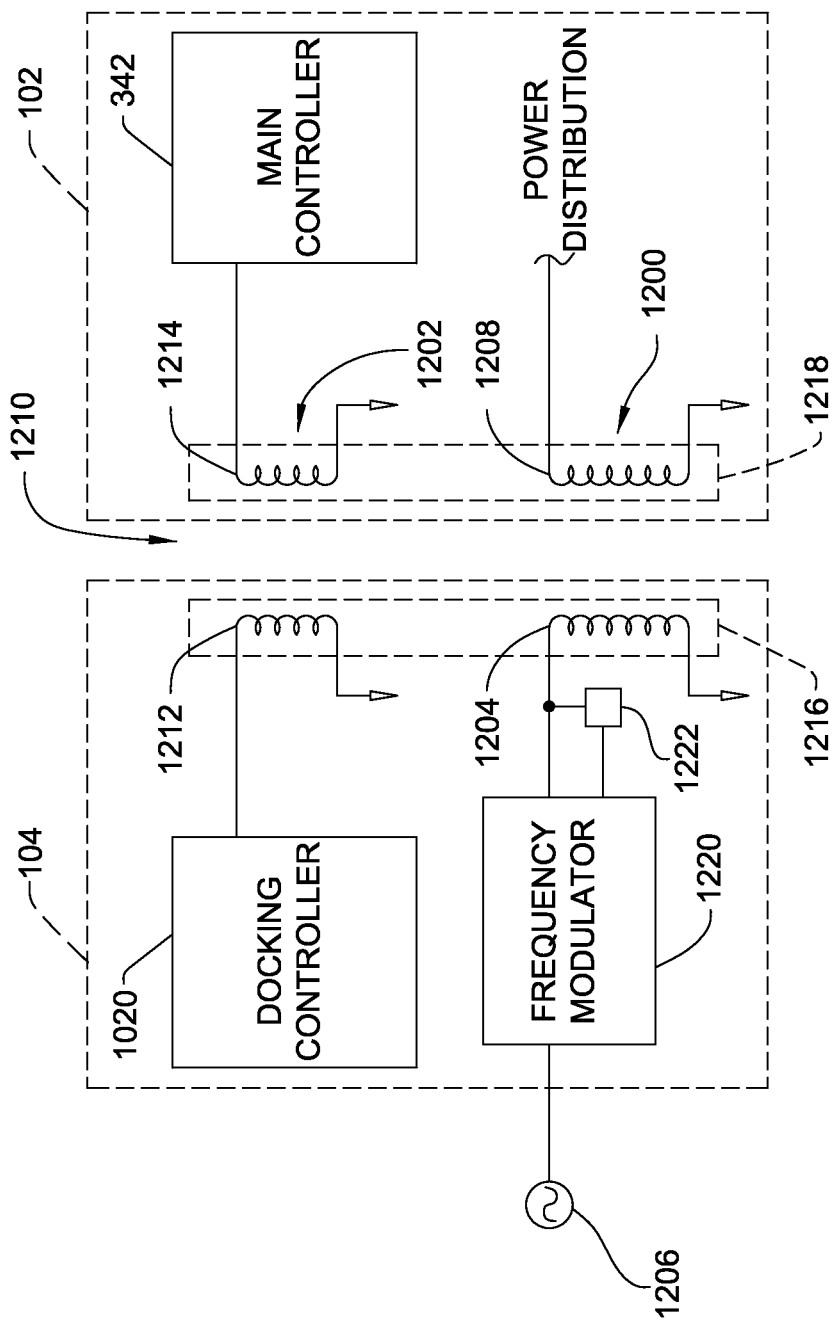
FIG. 73 is an electrical block schematic diagram of power and data couplers between the waste collection unit and the docking station.

A plurality of jet ports 1182 are defined in the sprinkler head 1180 for directing the water, with or without cleaner, from the docking station 104 to inside the waste containers 200, 202, to clean the waste containers 200, 202. Referring specifically to FIG. 72, each of the jet ports 1182 include a uniform bore 1184 having a uniform diameter formed in the sprinkler head 1180 and a cone-shaped exit 1186 extending from the uniform bore 1184 to an exterior of the sprinkler head 1180. As shown, the cone-shaped exit 1186 has an angle of 10 degrees between a central axis of the uniform bore 1184. The angle may vary between 1 degree and 20 degrees. The bore 1184 and cone-shaped exit 1186 may be laser drilled in the sprinkler head 1180, molded in the sprinkler head 1180, mechanically drilled in the sprinkler head 1180, or the like.

The jet ports 1182 are preferably formed in an asymmetric pattern (see FIG. 70) on the sprinkler head 1180 to ensure that all components inside the waste containers 200, 202 are adequately cleaned. More specifically, for each waste container 200, 202, the asymmetric jet ports 1182 are configured to direct a stream of cleaner onto an underside of the caps 222, 228, the mist traps 570, an interior of the walls 234, 246 of the canisters 218, 224, the bottoms 230, 232 of the canisters 218, 224, the sensor rod 702, and the float elements 708, 712 simultaneously. These sprinklers 1170 are specifically designed to focus the largest amount of water, with or without cleaner, at those areas that are most likely to build up with waste material during use and after the waste containers 200, 202 are emptied. The sprinklers 1170 are constructed of a unitary piece of polymeric material such as polyvinylchloride (PVC).

The cleaning system can be activated after the waste material has been off-loaded from the waste collection unit 102 to the waste drain D by the off-load pump 1004. Once this occurs, cleaning occurs based on the user desired level of cleaning. This can be accomplished by selecting a dial position or pressing a pushbutton 1190 on the control panel 310. The user may select between a "quick clean" option, a "normal clean" option, and an "extended clean" option. The user's selection is transmitting via a control signal to the main controller 342, which then instructs the docking controller 1020 on the docking station 104 to act accordingly. Cleaning of the waste containers 200, 202 may also occur automatically after the waste material has been drained from the waste containers 200, 202.

These cleaning options may simply be based on the amount of time that the waste containers 200, 202 are cleaned or may be based on the number of clean/rinse cycles performed. For instance, when the "quick clean" option is selected, the waste material is first dumped via the off-load pump 1004 to the waste drain D. Once the waste containers 200, 202 are emptied, the main controller 342 instructs the docking controller 1020 to open the water valve 1012 and inject cleaner from the container 1018 into the water line 1014 via the injector 1016. The water with cleaner then flows through the water coupling 1011 of the docking station 104 and the water coupling 1027 of the waste collection unit 102 to the upper 1156 and lower 1158 supply lines. The main controller 342 then opens the upper solenoid valve 1160 to allow the water with cleaner to flow through the upper 1156 supply line to the sprinkler 1170 in the upper waste container 200 to spray the water with cleaner, under pressure, into the upper waste container 200. The water with cleaner includes a ratio of cleaner to water of from 1:80 to 1:214, most preferably 1:128 or 1 ounce of cleaner per gallon of water. The transfer valve 276 remains open to allow the water with cleaner to flow from the upper waste container 200 to the lower waste container 202.

After the water with cleaner is sprayed in the upper waste container 200 for a predetermined period of time, the main controller 342 closes the upper solenoid valve 1160 and opens the lower solenoid valve 1162 to repeat the process for the lower waste container 202. In some instances, when there is enough water pressure present, both solenoid valves 1160, 1162 can be opened to clean both of the waste containers 200, 202 at the same time. While the lower waste container 202 is cleaned, the off-load pump 1004 can be continuously operating to dump the dirty water with cleaner into the waste drain D, or the off-load pump 1004 can be intermittently operated by the main controller 342 based on liquid levels measured in the lower waste container 202. After both the upper 200 and lower 202 waste containers have been cleaned, cleaner is no longer injected into the water line 1014 and water without cleaner flows through the cleaning system in a similar operation to rinse the upper 200 and lower 202 waste containers. When the "normal clean" option or "extended clean" options are selected, these clean/rinse cycles could be repeated two or more times. The "extended clean" option may also include soaking the canisters 218, 224 in detergent to remove more soil, grime, or waste material.

It should be appreciated that several different combinations of clean/rinse cycles, clean/rinse times, cleaner concentration, water flow, and the like could provide unlimited options. In any event, the cleaning cycle is dictated by the main controller 342, i.e., the main controller (including appropriate microprocessors) is programmed to instruct the docking controller 1020 as to when the water valve 1012 should be open/closed, when the cleaner should be injected into the water line 1014 by the injector 1016, how much cleaner should be injected into the water line 1014, and which solenoid valve 1160, 1162 should be opened to allow the flow of water with or without cleaner into the waste containers 200, 202.

XII. Power and Data Coupler

The mobile waste collection unit 102 requires both electrical power and data communications when docked with the docking station 104 to perform the various functions described above (e.g., offloading of waste material, cleaning, etc.). Therefore, the waste collection and disposal system 100 includes a power coupler 1200 and a data coupler 1202, as shown in FIG. 79. The power coupler 1200 transfers electric power from the fixed docking station 104 to the mobile waste collection unit 102. The data coupler 1202 transfers data between the fixed docking station 104 and the mobile waste collection unit 102.

In the preferred embodiment, the power coupler 1200 transfers electrical power via an inductive coupling. The power coupler 1200 includes a first winding 1204 supported by the fixed docking station 104. The first winding 1204 is electrically connected to a fixed power source 1206, such as a hospital's utility power. The power coupler 1200 further includes a second winding 1208 supported by the mobile waste collection unit 102. When the mobile waste collection unit 102 is docked with the fixed docking station 104, the first and second windings 1204, 1208 are brought in close proximity to one another and inductively coupled together. Therefore, electric power can be transferred across a dielectric gap 1210. This electric power can then be used by various systems of the mobile waste collection unit 102. Those skilled in the art realize that when the first and second windings 1204, 1208 have a substantially similar number of coils, the voltage of the electric power transferred across the power coupler 1200 will also be substantially similar. This voltage may be altered by modifying the ratio of coils between the first and second windings 1204, 1208.

A frequency modulator 1220 is preferably electrically connected between the power source 1206 and the first winding 1204. The frequency modulator 1220 alters the frequency of the signal from the power source 1206 to match the resonant frequency of the load provided by the various systems of the mobile waste collection unit 102. A phase sensor 1222 is electrically connected between the frequency modulator 1220 and the first winding 1204 to sense the phase difference between the current and voltage being provided to the first winding 1204. This phase difference is communicated to the frequency modulator 1220 such that the frequency modulator 1220 may vary the frequency to match the resonant frequency.

The data coupler 1202 of the preferred embodiment transfers data via an inductive coupling. The data coupler 1202 includes a third winding 1212 supported by the fixed docking station 104. The docking controller 1020 is electrically connected to the third winding 1212. The data coupler 1202 also includes a fourth winding 1214 supported by the mobile waste collection unit 102. When the mobile waste collection unit 102 is docked with the fixed docking station 104, the third and fourth windings 1212, 1214 are brought in close proximity to one another and inductively coupled together. The fourth winding is electrically connected to the main controller 342. Thus, the docking controller 1020 and the main controller 342 are able to communicate data back and forth, when the mobile waste collection unit 102 is docked with the fixed docking station 104.

The first and third windings 1204, 1212 are preferably packaged together in a docker coupler module 1216. The docker coupler module 1216, as shown in the head 1030 of the docking station 104 in FIG. 51, is preferably formed of plastic and isolates the first and third windings 1204, 1214 from one another. FIGS. 52 through 56 show an alternative head 1030 without the docker coupler module 1216. The second and fourth windings 1208, 1214 are preferably packaged together in a mobile unit coupler module 1218, also preferably formed of plastic and isolating the second and fourth windings 1208, 1214 from each other. Of course, those skilled in the art realize other suitable techniques for packaging the windings 1204, 1208, 1212, 1214.

As described above, the mobile waste collection unit 102 and the docking station 104 transfer fluids (e.g., waste material, water, etc.) back-and-forth. Therefore, use of an inductive coupling for the power and data couplers 1200, 1202 prevents accidental short circuits between the mobile waste collection unite 102 and the docking station 104 due to these fluids, in the case of a leak. Therefore, the electrical connections provided by the power and data couplers 1200, 1202 are essentially waterproof and provide a higher degree of safety to medical center personnel.

XIII. Operation

In use, the waste collection unit 102 is wheeled to a use area, e.g., an operating room, to be used in a medical procedure such as a knee surgery. At least one new disposable manifold 260 is inserted into one of the manifold receivers 258 mounted to the caps 222, 228 of the canisters 218, 224, and one or more suction lines 262 are connected to one or more inlets (or ports) on the disposable manifold 260. When a pushbutton 1301 on the control panel 310 is used to activate the vacuum pump 402, the vacuum pump 402 draws a selectively variable vacuum within one or more of the waste containers 200, 202, which causes a vacuum to be pulled through the suction lines 262 drawing in the waste material through the connected suction lines 262. The control dials or knobs 311, 313 on the control panel 310 are used to set the desired vacuum levels in the waste containers 200, 202.

Once the medical procedure is completed, or even during the medical procedure, the suction lines 262 may be disconnected and a new disposable manifold 260 inserted into the manifold receiver 258. Eventually, if the upper waste container 200 is being used, the upper canister 218 will become full and need to be emptied, or the operator may select to empty the upper canister 218, before being filled. At this point, the user selects the pushbutton 348 that sends the control signal to the valve controller 344 to open the transfer valve 276 and dump the waste material from the upper canister 218 to the lower canister 224. Then, collection of waste material can continue. When dumping the waste material from the upper canister 218 to the lower canister 224, the vacuum present in the upper waste container 200 is vented to atmospheric pressure A via its vacuum regulator 408. The vacuum in the lower waste container 202 is set to a pressure such as the lower desired vacuum level of the two waste containers 200, 202. As a result, the vacuum present in the lower waste container 202 helps pull the waste material into the lower waste container 202. Once both the upper 218 and lower 224 canisters are filled, or if the user desires to empty and clean the waste containers 200, 202 prior to being filled, the user wheels the waste collection unit 102 to the docking station 104 to off-load the waste material to the waste drain D and clean the waste containers 200, 202.

The main controller 342 of the waste collection unit 102 acts as a master controller to the docking controller 1020 of the docking station 104 to control the sequence of actuating the stepper motor 1076 to drive the docker couplings 1010, 1011 into the rover couplings 1026, 1027, draining the waste material from the canisters 218, 224, via the off-load pump 1004, cleaning the waste containers 200, 202 with the water and cleaner, and further draining the water with cleaner and rinsing the waste containers 200, 202.

XIV. Alternative Variations

The above is directed to one specific version of the invention. Other variations of the invention are possible. Thus, there is no requirement that each of the above features be in each of the described versions of the invention. Also, there is no requirement that this invention be limited to waste collection systems with a portable cart. In an alternative version of the invention, the system may be a static unit. In these versions of the invention, a valve similar to transfer valve 276 is provided to directly connect the lower waste container 202 to the hospital plumbing. A second transfer valve 276 may also be provided to directly connect the upper waste container 200 to the hospital plumbing.

Similarly, there is no requirement in all versions of the invention that gravity be employed as the force to transfer the waste in the upper waste container 200 to the lower waste container 202. Thus, in an alternative version of the invention, containers 200 and 202 may be located side by side. In these versions of the invention, there is a conduit that extends between the base of the container 202 to the top of container 204. Transfer valve 276 is in series with this conduit. When it is desirable to empty the contents of the small container 202 into the large container, the small container is vented to atmosphere and the transfer valve is opened. Then, the suction pump is actuated to draw the contents of container 202 into container 204.

Alternative suction regulator assemblies for independently regulating the level of the suction draw into each container 200 and 202 may also be provided. For example, one alternative suction regulator assembly connected between the vacuum source 402 and each waste container 200 and 202 consists of two (2) regulator assemblies each of which consists of two (2) valve members. Each of these suction regulator assemblies is located in series between the vacuum source 402 and a separate one of the waste containers 200 or 202. Each regulator assembly includes a first valve member that is adjustable to regulate the suction draw from the vacuum source 402. Between this first valve member and the associated waste container 200 or 202 there is the second valve member. This second valve member selectively opens/closes a connection between the vacuum line 496 or 510 upstream of the first valve member and a vent to atmosphere. By adjusting both valve members, the actual vacuum drawn on the associated container 200 or 202 is selectively set.

Similarly, suction regulators that include a single valve member associated with each container 200 or 202 are within the scope of this invention. One such valve member has a ball shaped valve head with either plural intersecting bores or a non-circular bore. This valve head is disposed in a housing with three ports; one to the vacuum source 402; one to the associated container 202 or 202; and one to atmosphere. By selectively rotating the valve head connections similar to those discussed above with the disc shaped valve members 412 are established.

Likewise, other versions of the invention may have fluid plumbing assemblies that are different from the primary illustrated version. For example, it may be desirable to construct collection unit 102 so that the upper supply line 1156 that extends from valve 1160 opens into the top of on-board reservoir 1164. During the cleaning process it is often desirable to first only discharge water through the spray head and, only after the water is sprayed, a water-detergent mixture. Therefore, in this version of the invention one can through the docker 104, first load a water-detergent mixture into reservoir 1164 through the top of the reservoir. Once the reservoir is filled with this mixture, the process of cleaning the upper waste container by sequentially introducing water and detergent into the container is initiated. In this process the fluid streams comprising the water or detergent are introduced into the unit 102 and more particularly into the upper supply line 1156. Since supply line 1156 opens into the already filled reservoir 1164 little of the fluid forming these streams is held in the reservoir. Instead, this fluid stream flows out of the top of the reservoir and is discharged from the spray head.

In one method of cleaning container 200 initially a detergent-free water stream is introduced into unit 102 and discharged from the spray head. This water stream removes waste that may have accumulated on the surfaces of the container 200. Then a water-detergent mixed fluid stream is introduced into the container to remove the waste that may be more congealed. Following the detergent-water cleaning cycle there is a detergent-free water rinse. At this point in the process, the container 200 is for most intents and purposes considered clean. Once so cleaned, container 200 is subject to a prefill from the docker 104. In this prefill process, a mixture of dilute detergent and water is flowed from the docker 104 through supply line 1156. Again since reservoir 1164 is already full, this fluid stream is discharged from the spray head into the base of the container 202.

Then, each time waste is transferred from container 200 to container 204, after the transfer process, the detergent water mixture in the reservoir 1164 is drawn on to prefill container 200.

Further, the actual structure of the display may vary from what is illustrated. It should be appreciated that regardless of the type of the display, the digits displaying the level fill data be at least 1.3 cm if not 2.6 cm tall or taller. This increases the likelihood that this data can be viewed across the area of an operating room.

Other techniques may be used to determine when the pole segment 911 is completely retracted or fully extended. The mechanical limit switches mat be replaced by Hall sensors. Each Hall sensor undergoes a state transition in response to the movement of a magnet integral with pole segment 911 toward or away from the magnet. In still another version of the invention, the extended/retracted state of pole segment 911 is determined by monitoring the voltage across and current drawn by motor 920. The determination from this monitoring that the motor is in a stall state is interpreted as indicating the pole segment 911 is fully extended or completely retracted. Thus, when motor is in this state, controller 940 deactivates the motor.

Obviously many modifications and variations of the present invention are possible in light of the above description. While this description is directed to particular embodiments, it is understood that those skilled in the art may conceive of modifications and/or variations to the specific embodiments shown and described herein. Any such modifications or variations, which fall within the purview of this description, are intended to be included herein as well. It is understood that the description herein is intended to be illustrative only and is not intended to be limited

What is claimed is:

1. A waste collection and disposal system for collecting and disposing of waste material collected through a suction line during a medical procedure, said system comprising:
   a rover including:
      a portable cart;
      at least one waste container supported by said cart, the container having a connecting member for receiving a suction line through which waste from a surgical site is able to flow into the container;
      a first rover coupling attached to said cart and configured to convey waste from the at least one waste container;
      a second rover coupling attached to said cart through which fluid is flowed into the at least one waste container; and
      a guide assembly mounted to said cart;
   a vacuum source that provides a vacuum to said at least one waste container to draw the waste through the suction line into said at least one waste container; and
   a docker, said docker comprising:
      a fixed frame;
      a floating frame that is attached to and able to move relative to said fixed frame;
      a first docker coupling configured to mate with said first rover coupling and that is connected to a drain line;
      a second docker coupling configured to mate with said second rover coupling and that is connected to a water line; and
      a mating interface that holds said first and second docker couplings to said floating frame so that said docker couplings can move relative to said floating frame between a disengaged position in which the docker couplings are spaced from said rover couplings and an engaged position in which the docker couplings are mated to said rover couplings
   wherein, said docker floating frame is positioned so that, when said rover is positioned adjacent said docker, said rover guide assembly engages said floating frame so that the engagement of said floating frame with said guide assembly results in the positioning of said floating frame so that said docker couplings are at least partially aligned with said rover couplings.

2. The waste collection and disposal system of claim 1, wherein:
   one of said docker mating interface or said rover cart further includes a guide rod; and
   the other of said rover cart or said docker mating interface includes a bore for receiving the said guide rod so as to, upon movement of said docker couplings from the disengaged position to the engaged position, further align said docker couplings with said rover couplings.

3. The waste collection and disposal system of claim 1, wherein said mating interface includes a motor for moving said docker couplings between the disengaged and engaged positions.

4. The waste collection and disposal system of claim 1, wherein said docker floating frame is connected to the docker fixed frame and has six degrees of freedom relative to said fixed frame.

5. The waste collection and disposal system of claim 1, wherein at least one spring connects said docker floating frame to said docker fixed frame.

6. The waste collection and disposal system of claim 1, wherein said rover guide assembly consists of at least one rail that is positioned to engage said docker floating frame so as to position said floating frame so that said docker couplings are at least partially aligned with said rover couplings.

7. The waste collection and disposal system of claim 1, wherein said rover includes plural said waste containers mounted to said cart.

8. The waste collection and disposal system of claim 1, wherein the vacuum source is mounted to said rover cart.

9. The waste collection and disposal system of claim 1, wherein:
   said rover cart includes a base that is elevated relative to ground level and said rover couplings are mounted to said cart base so as to be directed to a bottom end of said cart base; and
   said docker floating frame and said docker couplings are positioned to extend from said docker fixed frame so that, when said rover is positioned adjacent said docker, said docker floating frame is located below said rover cart base.

10. The waste collection and disposal system of claim 1, wherein said rover includes at least one fitting to which said vacuum source is connected and through which said vacuum source draws a vacuum on said at least one waste container.

11. The waste collection and disposal system of claim 1, wherein said connecting member of said at least one waste container is a manifold that is removably attached to said cart, said manifold having a fitting to which the suction line is attached.

12. A waste collection and disposal system for collecting and disposing of waste material collected through a suction line during a medical procedure, said system comprising:
- a rover, said rover including:
  - a mobile cart having a base that is elevated above ground level;
  - at least one waste container supported by said cart, said container having a connecting member for receiving a suction line through which medical/surgical waste is drawn into the container from a surgical handpiece applied to a surgical site;
  - a first rover coupling attached to said cart base and configured to convey waste from said at least one waste container, said first rover coupling being mounted to said cart so as to open below said cart base;
  - a second rover coupling attached to said cart base through which fluid is flowed into the at least one waste container, said second rover coupling being mounted to said cart so as to open below said cart base; and
  - at least one guide member mounted to said cart so as to extend downwardly below the portion of said cart base to which said rover couplings are mounted;
- a vacuum source that provides a vacuum to said at least one waste container to draw the waste through the suction line into said waste container; and
- a docker, said docker comprising:
  - a fixed frame;
  - a floating frame that is moveably attached and able to move relative to said fixed frame, said floating frame being positioned so that said cart base can be positioned over said floating frame;
  - a first docker coupling configured to mate with the first rover coupling and that is connected to a drain line;
  - a second docker coupling configured to mate with the second rover coupling and that is connected to a water line; and
  - a mating interface that holds said first and second docker couplings to said floating frame so that said docker couplings can move relative to said floating frame between a disengaged position in which the docker couplings are spaced from said rover couplings and an engaged position in which the docker couplings are mated to said rover couplings wherein, said floating frame is positioned so that, when said rover cart base is positioned over said floating frame, said rover guide member engages said floating frame so that the engagement of said floating frame with said guide member results in the positioning of said floating frame so that said docker couplings are at least partially aligned with said rover couplings.

13. The waste collection system of claim 12, wherein:
said docker floating frame includes an outer surface oriented to face said rover cart base and an inner surface opposite the outer surface; and
said rover guide member is positioned to, when said rover cart is placed over said floating frame, abut the inner surface of said floating frame.

14. The waste collection system of claim 12, wherein:
said docker floating frame includes: an outer surface oriented to face said rover cart; an inner surface opposite the outer surface; and a side surface that extends between the outer surface and the inner surface; and
said rover guide member is positioned to, when said rover cart is placed over said floating frame, extend around the side surface of said floating frame and abut the inner surface of said floating frame.

15. The waste collection system of claim 12, wherein:
said docker floating frame has opposed sides; and
two said guide members extend downwardly from said rover cart base, said guide members being spaced apart from each other and positioned to, when said rover cart base is placed over said floating frame, engage the opposed sides of said floating frame.

16. The waste collection system of claim 12, wherein said docker floating frame has a plate, said plate being the portion of said floating frame that is engaged by said rover at least one guide member.

17. The waste collection and disposal system of claim 12, wherein:
one of said docker mating interface or said rover cart base includes at least one guide rod; and
the other of said rover base or said docker mating interface includes a bore for receiving the said guide rod so as to, upon movement of said docker couplings from the disengage position to the engaged position, further align said docker couplings with said rover couplings.

18. The waste collection and disposal system of claim 12, wherein said mating interface includes a motor for moving said docker couplings between the disengaged and engaged positions.

19. The waste collection and disposal system of claim 12, wherein said docker floating frame is connected to the docker fixed frame and has six degrees of freedom relative to the fixed frame.

20. The waste collection and disposal system of claim 12, wherein at least one spring connects said docker floating frame to said fixed frame.

21. The waste collection and disposal system of claim 12, wherein said rover includes plural said waste containers mounted to said cart.

22. The waste collection and disposal system of claim 12, wherein said vacuum source is mounted to said rover cart.

23. The waste collection and disposal system of claim 12, wherein said connecting member of said at least one waste container is a manifold that is removably attached to said cart, said manifold having a fitting to which the suction line is attached.

24. The waste collection and disposal system of claim 12, wherein:
said docker floating frame is able to move vertically relative to said docker fixed frame; and
said rover guide member is configured to engage said rover floating frame so that the engagement of said floating frame results in the vertical alignment of said first and second docker couplings with said first and second rover couplings.

* * * * *